United States Patent [19]

Hamley et al.

[11] Patent Number: 5,883,102
[45] Date of Patent: Mar. 16, 1999

[54] PHARMACEUTICALLY ACTIVE COMPOUNDS

[75] Inventors: Peter Hamley, Rothley; Austen Pimm; Alan Tinker, both of Loughborogh; Haydn Beaton, Quorn; Thomas McInally, Loughborogh, all of United Kingdom

[73] Assignee: Astra Pharmaceuticals Limited, Herts, United Kingdom

[21] Appl. No.: 793,713

[22] PCT Filed: Oct. 14, 1996

[86] PCT No.: PCT/GB96/02496

§ 371 Date: Mar. 3, 1997

§ 102(e) Date: Mar. 3, 1997

[87] PCT Pub. No.: WO97/14686

PCT Pub. Date: Apr. 24, 1997

[30] Foreign Application Priority Data

Oct. 17, 1995 [GB] United Kingdom .................... 9521231
Feb. 9, 1996 [GB] United Kingdom .................... 9602668
Jul. 9, 1996 [GB] United Kingdom .................... 9614386

[51] Int. Cl.[6] .................... A01N 43/54; C07D 237/00; C07D 239/72
[52] U.S. Cl. .................... 514/259; 544/231; 544/293
[58] Field of Search .................... 544/231, 293; 514/259

[56] References Cited

PUBLICATIONS

N. Finch et al. "Rearrangement of 3–amino–1–benzimidazole . . . " Journal of Organic Chemistry, vol. 36 No. 11, 1971, Easton US, pp. 1463–1465.

Carrington, H.C., "1:2–Dihydro–2:2–dimethylquinazolines. The Condensation of Acetone with . . . , " J. Chem. Soc. 1955, pp. 2527–2528.

Primary Examiner—Mukund J. Shah
Assistant Examiner—Tamthom T. Ngo
Attorney, Agent, or Firm—Nixon Vanderhye

[57] ABSTRACT

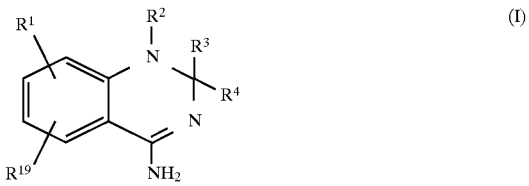

Compounds of formula (I) wherein:

$R^1$ and $R^{19}$ independently represent hydrogen, alkyl C1–6, alkoxy C1–6, alkylthio C1–6, halogen, hydroxyl or amino;

$R^2$ represents H or alkyl;

$R^3$ represents phenyl, a 6-membered heterocyclic aromatic ring containing one or two nitrogen atoms, or a 5-membered heterocyclic aromatic ring containing 1 to 3 heteroatoms selected from O,N, and S, which phenyl or heterocyclic aromatic ring may be optionally substituted by alkyl C1–6, alkoxy C1–6, haologen, hydroxyl, alkylthio C1–6, cyano, trifluoromethyl, nitro, hydroxymethyl, amino, a group $-(CH_2)_cNHCO_2R^{10}$, a group $-(CH_2)_cNR^5R^6$, or a group $-CO_2R^{11}$; or $R^3$ represents hydrogen or alkyl C1–8, which alkyl group may be optionally substituted by amino or a group $-NHCO_2R^{10}$;

$R^4$ represents hydrogen or alkyl C1–6; or $R^3$ and $R^4$ taken together represent a group $(CH_2)_aZ(CH_2)_b$;

c represents an integer 0 to 2;

and pharmaceutically acceptable salts thereof, have been found to be useful as a pharmaceuticals. The compounds may especially be used in the treatment of inflammatory disorders.

20 Claims, No Drawings

PHARMACEUTICALLY ACTIVE COMPOUNDS

This is a 371 application of PCT/GB96/02496, filed Oct. 14, 1996.

This invention relates to novel compounds, processes for their preparation, compositions containing them and their use as pharmaceuticals.

According to the invention, we provide a compound of formula I:

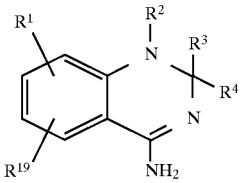

wherein $R^1$ and $R^{19}$ independently represent hydrogen, alkyl C1 to 6, alkoxy C1 to 6, alkylthio C1 to 6, halogen, hydroxyl or amino;

$R^3$ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic ring may be optionally substituted by alllyl C1 to 6, alkoxy C1 to 6, halogen, hydroxyl, alkylthio C1 to 6, cyano, trifluoromethyl, nitro, hydroxymethyl, amino, a group $-(CH_2)_c.NHCO_2R^{10}$, a group $-(CH_2)_c.NR^5R^6$, or a group $-CO_2R^{11}$, or $R^3$ represents hydrogen or alkyl C1 to 8, which alkyl group may be optionally substituted by amino or a group $-NHCO_2R^{10}$; and $R^4$ represents hydrogen or alkyl C1 to 6;

or $R^3$ and $R^4$ taken together represent a group $(CH_2)_a.Z.(CH_2)_b$;

c represents an integer 0 to 2;

a and b independently represent an integer 1 to 3;

Z represents $CH_2$, NH, a group $>N(CH_2)_nYR^{13}$, a group $>NCOX(CH_2)_nYR^{13}$, a group $>NCSX(CH_2)_nYR^{13}$, or a group $>NCNHX(CH_2)_nYR^{13}$;

X represents O, S or a bond;

Y represents O, S, SO, $SO_2$, $NR^9$ or a bond;

n represents an integer 0 to 6;

$R^{13}$ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or $R^{13}$ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trifluoromethoxy, methanesulphonyl, sulphamoyl, $-NR^{14}R^{15}$, $-COOR^{16}$ or $-CONR^7R^8$;

or $R^{13}$ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or $R^{13}$ may be as defined save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

$R^2$, $R^5$, $R^6$, $R^{11}$, $R^9$, $R^{14}$, $R^{15}$ and $R^{16}$ independently represent hydrogen or alkyl C1 to 6;

in addition, when Y represents $NR^9$, $-NR^9R^{13}$ may together represent a pyrrolidine or piperidine ring;

$R^{10}$ represents alkyl C1 to 6; and $R^7$ and $R^8$ independently represent hydrogen, alkyl C1 to 6 or phenyl optionally substituted by one or more groups selected from allyl C1 to 6, halogen, cyano, nitro, hydroxyl, alkoxy C1 to 6, trifluoromethyl and trifluoromethoxy;

provided that (a) when $R^3$ and $R^4$ taken together represent a group $(CH_2)_a.Z.(CH_2)_b$, in which Z represents a group $>NCOX(CH_2)_nYR^{13}$, a group $>NCSX(CH_2)_nYR^{13}$, or a group $>NCNHX(CH_2)_nYR^{13}$ in which neither X nor Y represents a bond then n represents an integer 2 to 4; and (b) when $R^3$ and $R^4$ taken together represent a group $(CH_2)_a.Z.(CH_2)_b$, in which Z represents a group $>NCOX(CH_2)_nYCN$, a group $>NCSX(CH_2)_nYCN$, or a group $>NCNHX(CH_2)_nYCN$, then Y represents a bond and either X also represents a bond or X does not represent a bond and n represents an integer 1 to 4;

or a pharmaceutically acceptable salt thereof, for use as a pharmaceutical.

Compounds of formula A:

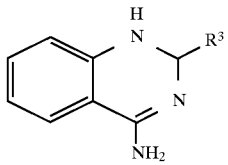

wherein $R^3$ represents phenyl or benzyl, have already been disclosed by Finch et al. (1971), *J Org. Chem.*, 36, 1463–1465.

Likewise compounds of formula B:

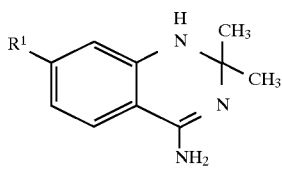

wherein $R^1$ represents hydrogen or chloro, have been disclosed by Carrington (1955), *J. Chem. Soc.*, 2527–2528. Neither paper gives any useful pharmaceutical properties of the compounds.

Thus in a further aspect of the invention we provide a compound of formula I:

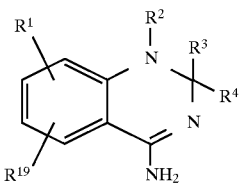

wherein
R¹ and R¹⁹ independently represent hydrogen, alkyl C1 to 6, alkoxy C1 to 6, alkylthio C1 to 6, halogen, hydroxyl or amino;

R³ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic nng may be optionally substituted by alkyl C1 to 6, alkoxy C1 to 6, halogen, hydroxyl, alkylthio C1 to 6, cyano, trifluoromethyl, nitro, hydroxymethyl, amino, a group —(CH₂)$_c$.NHCO₂R¹⁰, a group —(CH₂)$_c$.NR⁵R⁶, or a group —CO₂R¹¹, or R³ represents hydrogen or alkyl C1 to 8, which allyl group may be optionally substituted by amino or a group —NHCO₂R¹⁰; and R⁴ represents hydrogen or alkyl C1 to 6;

or R³ and R⁴ taken together represent a group (CH₂)$_a$.Z.(CH₂)$_b$;

c represents an integer 0 to 2;

a and b independently represent an integer 1 to 3;

Z represents CH₂, NH, a group >N(CH₂)$_n$YR¹³, a group >NCOX(CH₂)$_n$YR¹³, a group >NCSX(CH₂)$_n$YR¹³, or a group >NCNHX(CH₂)$_n$YR¹³;

X represents O, S or a bond;

Y represents O, S, SO, SO₂, NR⁹ or a bond;

n represents an integer 0 to 6;

R¹³ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or R¹³ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trirluoromethoxy, methanesulphonyl, sulphamoyl, —NR¹⁴R¹⁵, —COOR¹⁶ or —CONR⁷R⁸;

or R¹³ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or R¹³ may be as defmed save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

R², R⁵, R⁶, R¹¹, R⁹, R¹⁴, R¹⁵ and R¹⁶ independently represent hydrogen or alkyl C1 to 6;

in addition, when Y represents NR⁹, —NR⁹R¹³ may together represent a pyrrolidine or piperidine ring;

R¹⁰ represents alkyl C1 to 6; and

R⁷ and R⁸ independently represent hydrogen, alkyl C1 to 6 or phenyl optionally substituted by one or more groups selected from alkyl C1 to 6, halogen, cyano, nitro, hydroxyl, alkoxy C1 to 6, trifluoromethyl and trifluoromethqxy;

provided that (a) when R³ and R⁴ taken together represent a group (CH₂)$_a$.Z.(CH₂)$_b$, in which Z represents a group >NCOX(CH₂)$_n$YR¹³, a group >NCSX(CH₂)$_n$YR¹³, or a group >NCNHX(CH₂)$_n$YR¹³ in which neither X nor Y represents a bond then n represents an integer 2 to 4; and (b) when R³ and R⁴ taken together represent a group (CH₂)$_a$.Z.(CH₂)$_b$, in which Z represents a group >NCOX(CH₂)$_n$YCN, a group >NCSX(CH₂)$_n$YCN, or a group >NCNHX(CH₂)$_n$YCN, then Y represents a bond and either X also represents a bond or X does not represent a bond and n represents an integer 1 to 4;

(c) when R¹, R¹⁹, R² and R⁴ represent hydrogen, R³ does not represent phenyl; and (d) when R¹ represents hydrogen or chloro, and R¹⁹ and R² represent hydrogen, R³ and R⁴ do not both represent methyl;

or a pharmaceutically acceptable salt thereof.

We prefer R³ and R⁴ taken together to represent a group (CH₂)$_a$.Z.(CH₂)$_b$, in which Z represents a group >NCO(CH₂)$_n$R¹³, a group >NCS(CH₂)$_n$R¹³, or a group >NCNH(CH₂)$_n$R¹³ and R¹³ represents optionally substituted phenyl, furyl, thienyl, thiazolyl, isoxazolyl, isothiazolyl, thiadiazolyl, pyridyl or pyrazinyl. In such a case, we prefer n to represent zero, and R¹³ to represent substituted phenyl, wherein the substituent is in the para position.

We prefer R¹ and R¹⁹ independently to represent hydrogen or halogen, more preferably at least one of R¹ and R¹⁹ representing fluoro or chloro. R¹ may especially represent 5-fluoro or 5-chloro, and in particular R¹ may represent 5-fluoro and R¹⁹ 8-fluoro.

When R³ and R⁴ taken together represent a group (CH₂)$_a$.Z.(CH₂)$_b$, we prefer a and b each to represent 2.

We prefer R² to represent hydrogen.

When R⁴ represents hydrogen, we prefer R³ to represent ethyl, isopropyl, cyclopropyl or cyclobutyl; or fuiryl, thienyl or substituted phenyl wherein the substituent is fluoro or hydroxyl.

Alternatively, when R³ and R⁴ taken together may represent a group (CH₂)$_a$.Z.(CH₂)$_b$, in which Z represents a group >NCO₂(CH₂)$_n$YR¹³ or >NCSO(CH₂)$_n$YR¹³. In such a case, we prefer n to represent 0, Y to represent a bond and R¹³ to represent alkyl C1–6 or chloroalkyl C3–6; or n may represent 2, Y represent oxygen and R¹³ represent optionally substituted phenyl. In one particular aspect of the invention, we provide a compound of formula IA:

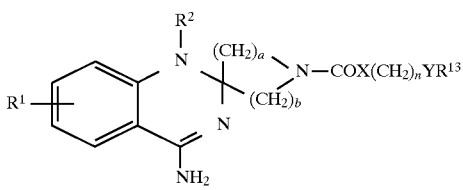

wherein
- $R^1$ represents hydrogen, alkyl C1 to 6, alkoxy C1 to 6 or halogen;
- a and b independently represent an integer 1 to 3;
- X represents O, S or a bond;
- Y represents O, S, $NR^9$ or a bond;
- n represents an integer 0 to 4;
- $R^{13}$ represents alkyl C1 to 6, cyano, trifluoromethyl, phthalimido, quinolyl, phenyl, a 6-membered heterocyclic aromatic ring containing one or two nitrogen atoms, a 5-membered heterocyclic aromatic ring containing 1 to 3 heteroatoms selected from O, N and S or a benzene ring fused with a 5-membered heterocyclic aromatic ring containing 1 to 3 heteroatoms selected from O, N and S;
- or $R^{13}$ may be as defined save that when it contains one or more aromatic rings, said rings may be optionally substituted by one or more groups selected from alkyl C1 to 6, halogen, cyano, nitro, hydroxy, alkoxy C1 to 6, trifluoromethyl, trifluoromethoxy, sulphonylmethyl, sulphonylamino, —$NR^{14}R^{15}$, —$COOR^{16}$ or —$CONR^7R^8$;
- or $R^{13}$ may represent a phenyl ring substituted by benzyloxy or optionally substituted phenyl or an optionally substituted 5-membered heterocyclic aromatic ring containing 1 to 3 heteroatoms selected from O, N and S, wherein the optional substituents are alkyl C1 to 6, halogen, cyano, nitro, hydroxy, alkoxy C1 to 6, trifluoromethyl and trifluoromethoxy;
- $R^2$, $R^{14}$, $R^{15}$, $R^{16}$ and $R^9$ independently represent hydrogen or alkyl C1 to 6;
- in addition, when Y represents $NR^9$, —$NR^9R^{13}$ may together represent a pyrrolidine or piperidine ring; and
- $R^7$ and $R^8$ independently represent hydrogen, alkyl C1 to 6 or phenyl optionally substituted by one or more groups selected from alkyl C1 to 6, halogen, cyano, nitro, hydroxy, alkoxy C1 to 6 and trifluoromethyl;

provided that
(a) when neither X nor Y represents a bond then n represents an integer 2 to 4;
(b) when $R^{13}$ represents cyano then Y represents a bond and either X also represents a bond or X does not represent a bond and n represents an integer 1 to 4;

and pharmaceutically acceptable salts thereof.

In a flrher aspect of the invention, we provide a compound of formula IB:

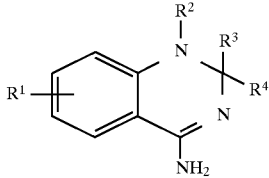

wherein
- $R^1$ represents hydrogen, alkyl C1 to 6, alkoxy C1 to 6, alkylthio C1 to 6 or halogen;

- $R^3$ represents phenyl or a six membered heterocyclic aromatic ring containing 1 to 3 nitrogen atoms, which phenyl or heterocyclic aromatic ring may be optionally substituted by alkyl C1 to 6, alkoxy C1 to 6, halogen, hydroxy, alkylthio C1 to 6, cyano, trifluoromethyl, nitro, hydroxymethyl or a group —$NR^5R^6$,
- or $R^3$ represents a five membered heterocyclic aromatic ring containing 1 to 3 heteroatoms selected from O, N or S optionally substituted by alkgl C1 to 6 or halogen,
- or $R^3$ represents hydrogen or alkyl C1 to 8; and
- $R^2$, $R^4$, $R^5$ and $R^6$ independently represent hydrogen or alkyl C1 to 6;

or a pharmaceutically acceptable salt thereof, for use as a pharmaceutical. According to the invention we also provide a process for the preparation of a compound of formula I, or a pharmaceutically acceptable salt thereof, which comprises:

(a) reaction of a compound of formula II:

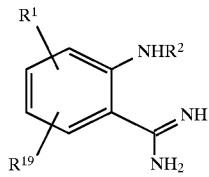

wherein $R^1$, $R^2$ and $R^{19}$ are as defined above, or an acid salt thereof, with a compound of formula III:

wherein $R^3$ and $R^4$ are as defined above, or a protected derivative thereof;

(b) preparation of a compound of formula I wherein $R^2$ represents alkyl C1 to 6 by alkylation of a corresponding compound of formula I wherein $R^2$ is hydrogen;

(c) preparation of a compound of formula I in which one or more of the substituents contains an amino group by reduction of the corresponding nitro or azido compound;

(d) preparation of a compound of formula I wherein $R^{13}$ contains a substituent —$CONR^7R^8$ by reaction of a compound of formula I wherein $R^{13}$ contains a substituent —COOH with an amine $R^7R^8NH$;

(e) preparation of a compound of formula I where $R^3$ and $R^4$ together represent $(CH_2)_aZ(CH_2)_b$ and Z represents >$NCOX(CH_2)_nYR^{13}$ by reaction of a compound of formula I where $R^3$ and $R^4$ together represent $(CH_2)_aZ(CH_2)_b$ and Z represents >NH is with a compound of formula IV:

$$R^{13}Y(CH_2)_nXCOL \qquad IV$$

wherein $R^{13}$, X, Y and n are as defined above and L is a leaving group;

(f) preparation of a compound of formula I where $R^3$ and $R^4$ together represent $(CH_2)_aZ(CH_2)_b$ and Z represents >$NSO_2R^{13}$ by reaction of a compound of formula I where $R^3$ and $R^4$ together represent $(CH_2)_aZ(CH_2)_b$ and Z represents >NH with a compound of formula V:

$$R^{13}SO_2L \qquad V$$

wherein $R^{13}$ is as defined above and L is a leaving group;

(g) preparation of a compound of formula I wherein $R^3$ or $R^{13}$ represents a ring substituted by a group —$COOR^{11}$ or —COOR$^{16}$ respectively and R$^{11}$ or R$^{16}$ represents alkyl C1 to 6 by esterification of the compound where R$^{11}$ or R$^{16}$ represents hydrogen;

(h) deprotection of a compound of formula I wherein one or more atoms is protected;

(i) reaction of a compound of formula XXII:

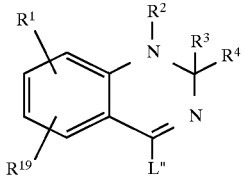

XXII wherein R$^1$, R$^2$, R$^3$, R$^4$ and R$^{19}$ are as defined above, and L" is a leaving group, or a protected derivative thereof, with ammonia or a deprotonated derivative thereof;

(j) deoxygenation of the tautomeric compounds of formula XXVIII(a) or XXVIII(b):

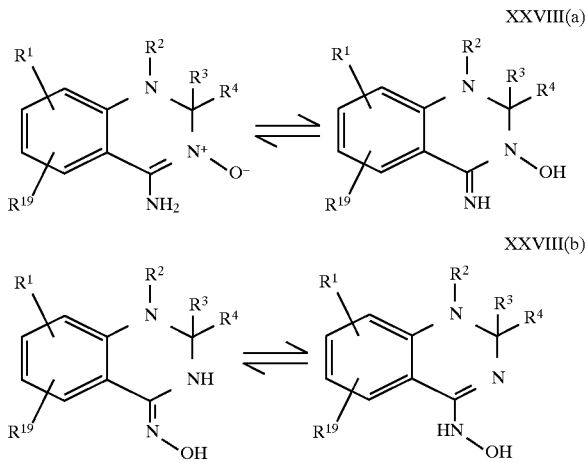

XXVIII(a)

XXVIII(b)

wherein R$^1$, R$^2$, R$^3$, R$^4$ and R$^{19}$ are as defined above, or a protected derivative thereof; or (k) preparation of a compound of formula I in which R$^2$ and R$^4$ both represent hydrogen by reduction of a compound of formula XXIX:

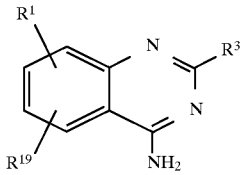

XXIX wherein R$^1$, R$^3$ and R$^{19}$ are as defined above, or a protected derivative thereof;

and where desired or necessary converting the resultant compound of formula I, or another salt thereof, to a pharmaceutically acceptable salt thereof, or vice versa.

In process (a) the reaction of compounds of formulae II and III may be carried out by stirring the reactants in an inert solvent at a temperature between room temperature and the boiling point of the solvent, or without solvent at a temperature between room temperature and 200° C. for a period of 1 to 72 hours, or until reaction is complete. We have found that it is frequently desirable to use the carbonyl compound III in protected form as an acetal or ketal; we find the ethylene ketal to be particularly suitable for ketones. Ethylene ketals may be formed readily by condensing a ketone with ethylene glycol under conditions well known in the art.

In process (b) the alkylation reaction may be performed by processes well known in the art. For example, the amine can be reacted with an alkyl halide, especially the bromide or iodide.

In process (c) the reduction may be carried out catalytically by stirring the reactant in an inert solvent under an atmosphere of hydrogen in the presence of a metal catalyst, or for example by the action of a metal or metal halide (e.g. iron, tin or tin(II) chloride) in an acid, e.g. hydrochloric acid.

In process (d) the reaction of the acid and amine may be carried out in an inert solvent in the presence of a condensing agent, for example N,N'-carbonyldiimidazole or dicyclohexylcarbodiimide, or the acid may be first activated by conversion to e.g. and acyl chloride before reaction with the amine.

In processes (e) and (f) the reaction may be performed by combining the reactants in an inert solvent at ambient temperature in the presence of a base e.g. pyridine or triethylamine. Although a number of leaving groups L might be suitable we prefer that L represent a halogen, especially chlorine or bromine.

In process (g) the esterification reaction may be performed under conditions well known to a person skilled in the art. For example, the acid, which may be optionally activated (e.g. as the acyl chloride), may be reacted with an appropriate alcohol under conditions of acid or basic catalysis.

In process (h), protecting groups for amines and hydroxyl groups include, alky, aralkyl, acyl, alkoxyacyl, alkylsuiphonyl, arylsulphonyl and triallylsilyl. When the group is alkyl, acyl, or alkoxyacyl this group may be removed by hydrolysis. Aralkyl groups may be remove by hydrogenolysis. Alkylsulphonyl or arylsulphonyl groups may be removed by reduction with, for example, zinc and acetic acid or sodium and ammonia. Trialkylsilyl groups may be removed by reaction with tetra-n-butylammonium fluoride. Other protecting groups and firter details of processes for their removal may be found by reference to the standard text "Protecting Groups in Organic Synthesis", 2nd. Edition (1991) by Greene and Wuts.

In process (i), suitable leaving groups L" include chlorine, alkoxy, alkylthio and trifluoromethanesulphonyloxy. The reaction may be carried out with ammonia in a solvent, or with a metal amide salt.

In processes (j) and (k), any suitable means of reduction may be used, such as catalytic hydrogenation or reaction with a hydride reagent.

Salts of compounds of formula I may be formed by reacting the free base or a salt thereof, with one or more equivalents of the appropriate acid. The reaction may be carried out in a solvent or medium in which the salt is insoluble e.g. diethyl ether or in a solvent in which the salt is soluble e.g. dioxane, ethanol, tetrahydrofuran or water, or a mixture of solvents which may be removed in vacuo or by freeze drying. The reaction may be a metathetical process or it may be carried out on an ion exchange resin.

Compounds of formula II may be prepared by reduction of compounds of formula VI:

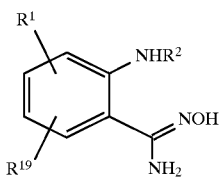

wherein $R^1$, $R^2$ and $R^{19}$ are as defined above.

This reaction process may be performed by treating the compound with Raney nickel and hydrogen gas in a polar solvent e.g. ethanol at elevated temperature and pressure, typically 65° C. and 3 atmospheres pressure. Alternative reaction procedures which are considered suitable include treatment of the compound of formula VI under a hydrogen atmosphere with palladium on charcoal or rhodium on alumina.

Compounds of formula VI may be prepared by reaction of a compound of formula VII:

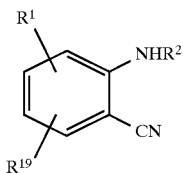

wherein $R^1$, $R^2$ and $R^{19}$ are as defined above, with hydroxylamine hydrochloride.

In this reaction the two reactants may be heated in the presence of a base, such as sodium methoxide in a solvent e.g. methanol.

Alternative preparation methods for compounds of formula II include, reaction of a compound of formula VII with ammonium chloride in the presence of a trialkylaluminium reagent, or reaction of a compound formula VII with a primary alcohol e.g. ethanol in the presence of acid and subsequent treatment with ammonium chloride.

Compounds of formula II in which $R^{19}$ is 5-hydroxy may be prepared by reduction of a benzisoxazole derivative of formula VIII:

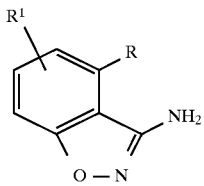

in which R represents —$NO_2$, to give the compound in which $R^2$ represents hydrogen, or —$NHR^2$ and $R^1$ and $R^2$ are as previously defined.

In this reaction the reduction may be carried out by stirring the compound of formula VIII with Raney nickel under hydrogen in a polar solvent e.g. ethanol at elevated temperatures and pressures typically 65° C. and 3 atmospheres pressure.

Compounds of formula VIII may be prepared by reaction of a compound of formula

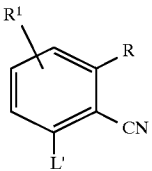

wherein R and $R^1$ are as defined above and L' is a leaving group, particularly halogen or nitro, with an alkyl ester of N-hydroxycarbamic acid. This process is preferably carried out in an aprotic, polar solvent e.g. DMF with a basic catalyst e.g. an alkali metal hydroxide. We have found the tert-butyl ester of N-hydroxycarbamic acid to be particularly favourable for this process.

Compounds of formula VII where $R^2$ represents alkyl C1 to 6 may be prepared by alkylation of the corresponding compounds where $R^2$ represents hydrogen. Alternatively a compound of formula VII where $R^2$ represents alkyl C1 to 6 may be prepared by alkylation of an amide of formula VII':

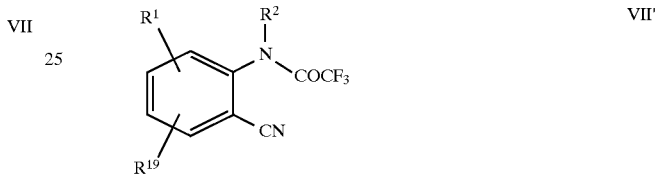

wherein $R^1$ and $R^{19}$ are as defined above and $R^2$ represents hydrogen, followed by hydrolysis of the amide.

The alkylation reaction may be performed by treating the compound of formula VII or VII' where $R^2$ represents hydrogen with an alkyl halide in a polar solvent e.g. DMF optionally in the presence of a basic catalyst e.g. an alkali metal carbonate, hydroxide, alkoxide or hydride. The hydrolysis reaction may performed under conditions well known to those sldlled in the art.

The compounds of formula VII and VII' where $R^2$ represents hydrogen, and IX are either known or may be made by methods known per se.

Compounds of formula III where $R^3$ and $R^4$ together represent $(CH_2)_a Z(CH_2)_b$ and Z represents >$NCOX(CH_2)_n YR^{13}$ or >$NSO_2 R^{13}$ can be prepared by reaction of a compound of formula X:

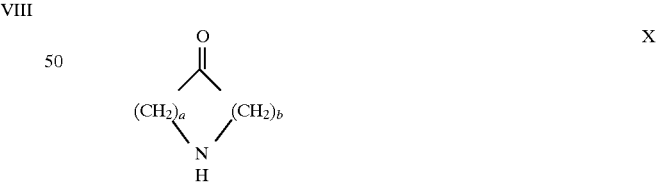

wherein a and b are as defined above, or a protected derivative thereof, with a reagent of formula IV or V respectively.

This process is carried out in an inert solvent, e.g. ethyl acetate, dichloromethane or DMF in the presence of a base, e.g. pyridine.

Compounds of formula III where $R^3$ and $R^4$ together represent $(CH_2)_a Z(CH_2)_b$ and Z represents >$NCOX(CH_2)_n YR^{13}$ can be prepared by reaction of a compound of formula X with an imidazole derivative of formula XI:

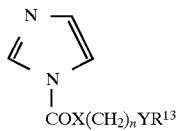

wherein $R^{13}$, X, Y and n are as defined above.

This process can be carried out by combining the reactants in an inert solvent such as dichloromethane or acetonitrile.

Compounds of formula III where $R^3$ and $R^4$ together represent $(CH_2)_aZ(CH_2)_b$ and Z represents >NCONR$^9$R$^{13}$ can be prepared by reaction of a compound of formula X with an imidazole derivative of formula XII':

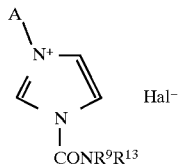

XII' wherein $R^9$ and $R^{13}$ are as defined above, A represents an alkyl group and Hal represents a halogen atom.

This process can be carried out by combining the reactants in an inert solvent such as dichloromethane or acetonitrile. The quaternary salt compound of formula XII' can be prepared by reacting a compound of formula XII:

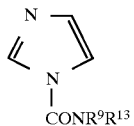

XII wherein $R^9$ and $R^{13}$ are as defined above, with an alkyl or aralkyl halide e.g. methyl iodide or benzyl bromide in an inert solvent.

Compounds of formula XI in which X represents a bond may be formed by reacting an acid of formula XIII:

$R^{13}Y(CH_2)_nCO_2H$      XIII wherein $R^{13}$, Y and n are as defined above, with N,N'-carbonyldiimidazole in an inert solvent.

Compounds of formula XI in which X represents oxygen may be formed by reacting an alcohol of formula XIV:

$R^{13}Y(CH_2)_nOH$      XIV wherein $R^{13}$, Y and n are as defined above, with N,N'-Ncarbonyldiimidazole in an inert solvent.

Compounds of formula XII may be prepared by reacting a primary or secondary amine of formula XV:

$R^{13}R^9NH$      XV wherein $R^9$ and $R^{13}$ are as defined above, with N,N'-carbonyldiimidazole in an inert solvent.

Alternatively compounds of formula XII can be prepared by reacting a compound of formula XVI:

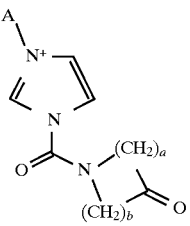

XVI wherein a and b are as defined above, A is an alkyl or arylawkyl group and Hal is a halogen atom, or a protected derivative thereof, with a compound of formula XV.

This process can be carried out by combining the reactants in an inert solvent such as dichloromethane or acetonitrile.

Compounds of formula XVI may be prepared by reacting an alkyl or arylalkyl halide (e.g. methyl iodide or benzyl bromide) with a compound of formula XVI':

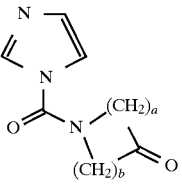

XVI' wherein a and b are as defined above.

Compounds of formula XVI' may be prepared by reaction of a compound of formula X or a protected derivative thereof with N,N'-carbonyldiimidazole in an inert solvent.

Compounds of formula III where $R^3$ and $R^4$ together represent $(CH_2)_aZ(CH_2)_b$ and Z represents >NCNHX(CH$_2$)$_n$YR$^{13}$ may be prepared by reacting a compound of formula X with a compound of formula XVII:

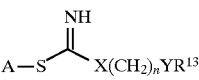

XVII wherein $R^{13}$, X, Y and n are as defined above and A represents an alkyl group.

or a salt thereof.

Compounds of formula III where $R^3$ and $R^4$ together represent $(CH_2)_aZ(CH_2)_b$ and Z represents >NCSX(CH$_2$)$_n$YR$^{13}$ may be prepared by reacting a compound of formula X with a compound of formula XVIII:

$R^{13}Y(CH_2)_nXCSL$      XVIII wherein $R^{13}$, X, Y and n are as defined above and L is a leaving group.

This process may be carried out in a protic solvent e.g. water. The compound of formula XVI can be conveniently generated in situ by the action of a chlorinating agent e.g. sodium hypochlorite on an alkyl xanthate salt, XIX:

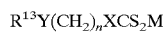

$R^{13}Y(CH_2)_nXCS_2M$      XIX wherein $R^{13}$, X, Y and n are as defined above and M is an alkali metal, e.g. sodium or potassium.

Compounds of formula III where $R^3$ and $R^4$ together represent $(CH_2)_aZ(CH_2)_b$ and Z represents >NCONHR$^{13}$ or >NCSNHR$^{13}$ may be prepared by reacting a compound of formula X with a compound of formula XX or XXI respectively:

R$^{13}$NCO            XX

R$^{13}$NCS            XXI wherein R$^{13}$ is as defined above.

This process may be carried out in an inert solvent e.g. benzene or toluene at a temperature between room temperature and the reflux temperature of the solvent.

Alternatively, compounds of formula III where R$^3$ and R$^4$ together represent $(CH_2)_aZ(CH_2)^b$ and Z represents >NCSX $(CH_2)_n YR^{13}$ may be prepared by reacting a compound of formula III where R$^3$ and R$^4$ together represent $(CH_2)_aZ$ $(CH_2)_b$ and Z represents >NCOX$(CH_2)_n YR^{13}$ with a thiation reagent such as phosphorus pentasulphide or Lawesson's reagent.

Compounds of formula XXII in which L" represents alkoxy may be prepared by reaction of a compound of formula XXIII:

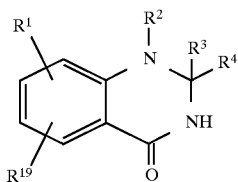

XXIII wherein R$^1$, R$^2$, R$^3$, R$^4$ and R$^{19}$ are as defined above,
or a protected derivative thereof,
by treatment with a suitable alkylating agent such as Meerwein's salt (trimethyloxonium tetrafluoroborate) giving the compound where L" is methoxy.

Compounds of formula XXII in which L" represents trifluoromethanesulphonyloxy may be prepared from a compound of formula XXIII, wherein R$^1$, R$^2$, R$^3$, R$^4$ and R$^{19}$ are as defined above, or a protected derivative thereof, by treatment with triflic anhydride in the presence of a suitable catalyst.

Compounds of formula XXIII may be prepared from a compound of formula VII, wherein R$^1$, R$^2$ and R$^{19}$ are as defined above, or a protected derivative thereof, by reaction with a compound of formula III, wherein R$^3$ and R$^4$ are as defined above, or a protected derivative thereof, by using a base such as sodium methoxide in a suitable solvent. Alternatively, the compound of formula II may first be hydrolysed to the corresponding amide of formula XXIV:

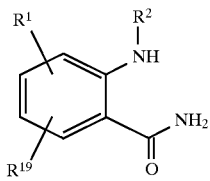

XXIV wherein R$^1$, R$^2$ and R$^{19}$ are as defined above,
or a protected derivative thereof,
and the ring-closing step to give the compound of formula XXIII is performed using a compound of formula III, wherein R$^3$ and R$^4$ are as defined above, or a protected derivative thereof, optionally in the presence of an acid catalyst, in a suitable solvent.

Compounds of formula XXII in which L" represents alkylthio may be prepared by reaction of a compound of formula XXV:

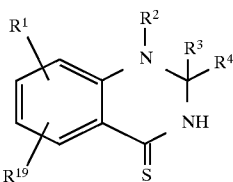

XXV wherein R$^1$, R$^2$, R$^3$, R$^4$ and R$^{19}$ are as defined above,
or a protected derivative thereof,
by treatment with a suitable alkylating agent such as an alkyl halide, optionally in the presence of a base, in a suitable solvent.

Compounds of formula XXV may be prepared from a compound of formula XXIII, wherein R$^1$, R$^2$, R$^3$, R$^4$ and R$^{19}$ are as defined above, or a protected derivative thereof, using Lawesson's reagent or phosphorus pentasulphide in a solvent. Alternatively, compounds of formula XXV may be prepared from a compound of formula XXVI:

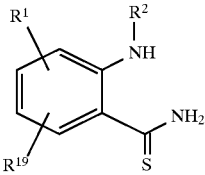

XXVI wherein R$^1$, R$^2$, and R$^{19}$ are as defined above,
or a protected derivative thereof,
using conditions analogous to those used in converting compounds of formula XXIV to compound of formula XXIII.

Compounds of formula XXVI may be prepared from a compound of formula XXIV, wherein R$^1$, R$^2$, and R$^{19}$ are as defined above, or a protected derivative thereof, using Lawesson's reagent or phosphorus pentasulphide in a solvent.

Compounds of formula XXII in which L" represents an alkylthio group of formula R'S may also be prepared by reaction of a compound of formula XXVII:

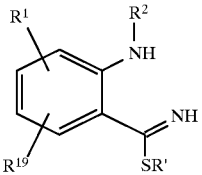

XXVII wherein R$^1$, R$^2$, and R$^{19}$ are as defined above,
or a protected derivative thereof,
with a compound of formula III, wherein R$^3$ and R$^4$ are as defined above, or a protected derivative thereof. The reaction may be performed by heating in a suitable solvent, optionally in the presence of an acid catalyst.

Compounds of formula XXVII may be prepared from a compound of formula XXVI, wherein R$^1$, R$^2$, and R$^{19}$ are as defined above, or a protected derivative thereof, by treatment with a suitable alkylating agent such as an alkyl halide, optionally in the presence of a base, in a suitable solvent.

The tautomeric compounds of formula XXVIII(a) and XXVIII(b) may be prepared by reaction of a compound of formula VI, wherein R$^1$, R$^2$, and R$^{19}$ are as defined above, or a protected derivative thereof, with a compound of formula III, wherein R$^3$ and R$^4$ are as defined above, or a protected derivative thereof The reaction may be performed by heating in a suitable solvent, optionally in the presence of an acid catalyst. The exact proportions of the two pairs of tautomeric species XXVIII(a) and XXVIII(b) that are produced depends on solvent and temperature.

Compounds of formula XXIX may be prepared according to the method used by D. Korbonits et al. in *Chem. Ber.* 117, 1984, page 3183, where the compound in which $R^1$ and $R^{19}$ represent hydrogen and $R^3$ represents phenyl is prepared.

Compounds of formula X, XIII to XV, XVII and XIX to XXI are either known compounds or may be made by methods known per se.

Intermediate compounds may be used in protected form. For example, ketones may be used as ketals as mentioned above. Other protecting groups and details of processes for their removal may be found by reference to the standard text "Protectinrg groups in Organic Synthesis", 2nd Edition (1991) by Greene and Wuts.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, e.g. fractional crystallisation, or HPLC.

Intermediate compounds may also exist in enantiomeric forms and may be used as purified enantiomers, diastereomers, racemates or mixtures.

The compounds of formula I may exist in the alternative tautomeric form IT:

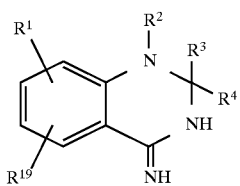

wherein $R^1$, $R^2$, $R^3$, $R^4$ and $R^{19}$ are as defined above. Compounds of formula I are provided in either tautomeric form or as a mixture thereof.

"Alkyl C1 to 6" and "alkyl C1 to 8" include straight chain, branched, cyclic, saturated or unsaturated alkyl containing 1 to 6 carbon atoms. The term "alkoxy C1 to 6" may be interpreted similarly.

The compounds of formula I, and pharmaceutically acceptable salts thereof, are useful because they possess pharmacological activity in animals. In particular, the compounds are active as inhibitors of the inducible isoform of the enzyme nitric oxide synthase and as such are expected to be useful as anti-flamnmatory agents.

The activity of compounds according to the invention was tested in the following screen:

The activity of compounds of formula I, or a pharmaceutically acceptable salt thereof, may be screened for nitric oxide synthase inhibiting activity by a procedure based on that of Förstermarm et al. (1992), *Eur. J Pharm.* 225, 161–165. Nitric oxide synthase converts [$^3$H]-L-arginine to [$^3$H]-L-citrdlline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/ml penicillin G, 100 µg/ml streptomycin & 0.25 µg/ml amphotericin B). Cells are routinely grown in 225 cm³ flasks containing 35 ml medium kept at 37° C. and in a humidified atmosphere containing 5% $CO_2$.

Nitric oxide synthase is produced by J774A-1 cells in response to interferon-y (IFNγ) and lipopolysaccharide (LPS). The medium from confluent culture flasks is removed and is replaced with 25 ml (per flask) of fresh medium containing 1 µg/ml LPS and 10 units/ml IFNγ. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 µg/ml), soya bean trypsin inhibitor (10 µg/ml), aprotinin (5 µg/ml) and phenylmethylsulphonyl fluoride (50 µg/ml).

For the assay, 25 µl substrate cocktail (50 mM Tris-HCl (pH 7.5 at 20° C.), 400 µM NADPH, 20 µM flavin adenine dinucleotide, 20 µM flavin mononucleotide, 4 µM tetrahydrobiopterin, 12 µM L-arginine and 0.025 mCi L-[$^3$H] arginine) is added to wells of a 96 well filter plate (0.45 µm pore size) containing 25 µl of a solution of test compound in 50 mM Tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA.

Labelled Lcitrulline is separated from labelled L-arginine using Dowex AG-50W. 150 µl of a 25% aqueous slurry of Dowex 50W (Na$^+$form) is added to the assay after which the whole is filtered into 96 well plates. 75 µl of filtrate is sampled and added to wells of 96 well plates containing solid scintillant. After allowing the samples to dry the L-citrulline is quantified by scintillation counting.

In a typical experiment basal activity is 300 dpm per 75 µl sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 µM, is tested as a standard to verify the procedure. Compounds are tested at a range of concentrations and from the inhibitions obtained $IC_{50}$ values are calculated. Compounds that inhibit the enzyme by at least 25% at 100 µM are classed as being active and are subjected to at least one retest.

In the above screen, the compounds were tested and most gave $IC_{50}$ values of less than 25 µM indicating that they are expected to show useful therapeutic activity.

Compounds also show activity against the human form of induced nitric oxide synthase as can be demonstrated in the following assay.

Enzyme is prepared, after induction, from the cultured human colon adenocarcinoma cell line DLD1 (obtained from the European Collection of Animal Cell Culture—cell line number 90102540). DLD1 cells are cultured in RPMI 1640 medium supplemented with 10% foetal bovine serum, 4 mM L-glutamine and antibiotics (100 units/ml penicillin G, 100 µg/ml streptomycin and 0.25 µg/ml amphotericin B). Cells are routinely grown in 225 cm³ flasks containing 35 ml kept at 37° C. and in a humified atmosphere containing 5% $CO_2$.

Nitric oxide synthase is produced by cells in response to interferon-γ (IFN-γ) and inter-leukin-1β (IL-1β). The medium from confluent flasks is removed and replaced with 25 ml (per flask) of fresh medium containing 250 units/ml IL-1β and 1000 units/ml IFN-γ. After a period of 17–20 hours in culture, harvesting of cells is accomplished by scraping the cell monolayer from the flask surface into the culture medium. Cells are collected by centrifuigation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X100, 0.1 mM dithiothreitol and a cocktail of protease inhibitors including leupeptin (2 μg/ml), soya been trypsin inhibitor (10 μg/ml), aprotonin (5 μg/ml) and phenylmethylsulphonyl fluoride (50 μg/ml).

For the assay, 25 μl of substrate cocktail (50 mM Tris-HCl (pH 7.5), 400 μM NADPH, 20 μM flavin adenine dinucleotide, 20 μM flavin mononucleotide and 4 μM tetrahydrobiopterin) is added to the wells of a 96-well plate. Test compounds are preincubated with enzyme by adding together with 40 μl of cell lysate (prepared as above) and incubating for 1 hour at 37° C. at the end of which period 10 μl of 30 μM L-arginine and 0.025 μCi of L-[$^3$H]-arginine in 50 mM Tris-HCl is added to start the enzymic reaction. Incubation is continued for a further 1 hour at 37° C. The reaction is terminated by addition of 50 μl of an aqueous solution of 3 mM nitroarginine and 21 mM EDTA.

Labelled L-citrulline is separated from labelled L-arginine using Dowex AG-50W. 120 μl of a 25% aqueous slurry of Dowex 50W is added to 96 well filter plates (0.45 μm pore size). To this is added 120 μl of terminated assay mix. 75 μl of filtrate is sampled and added to the wells of 96 well plates containing solid scintillant. After allowing the samples to dry the L-citrulline is quantified by scintillation counting.

In a typical experiment basal activity is 300 dpm per 75 μl sample of reagent controls, which is increased to 3000 dpm in the presence of enzyme. Compound activity is expressed as $IC_{50}$ (the concentration of drug substance which gives 50% enzyme inhibition in the assay) and L-NMMA, which gives an $IC_{50}$ of about 0.4 μM is tested as a standard to verify the procedure. Compounds are tested at a range of concentrations and from the inhibitions obtained $IC_{50}$ values are calculated.

In the above screen the compounds of Examples 1, 3 to 7, 10 to 18, 20 to 23, 27 to 49, 52, 54 to 62, 64 to 67, 69 to 72, 74 to 82, 84 to 88, 90 to 93, 98 to 170, 173 to 180, 182 to 242, 245 to 251 and 253 to 257 were tested and gave $IC_{50}$ values less than 25 μM, indicating that they are expected to show useful therapeutic activity.

The compounds are indicated for use in the treatment or prophylaxis of diseases or conditions in which synthesis or oversynthesis of nitric oxide synthase forms a contributory part. In particular, the compounds are indicated for use in the treatment of inflammatory conditions in mammals including man.

Conditions that may be specifically mentioned are:

osteoarthritis, rheumatoid arthritis, rheumatoid spondylitis, gouty arthritis and other arthritic conditions, inflamed joints;

eczema, psoriasis, dermatitis or other inflammatory skin conditions such as sunburn;

inflammatory eye conditions including uveitis and conjunctivitis;

lung disorders in which inflammation is involved, e.g. asthma, bronchitis, pigeon fancier's disease, farmer's lung, acute respiratory distress syndrome, bacteraemia, endotoxaemia (septic shock) and pancreatitis;

conditions of the gastrointestinal tract including aphthous ulcers, gingivitis, Crohn's disease (a condition of the small and sometimes also of the large intestine), atrophic gastritis and gastritis varialoforme (conditions of the stomach), ulcerative colitis (a condition of the large and sometimes of the small intestine), coeliac disease (a condition of the small intestine), regional ileitis (a regional inflammatory condition of the terminal ileum), peptic ulceration (a condition of the stomach and duodenum) and irritable bowel syndrome; pain; damage to the gastrointestinal tract resulting from infections by, for example, *Helicobacter pylori,* or treatments with non-steroidal anti-inflammatory drugs; and other conditions associated with inflammation.

The compounds of formula I may also be useful in the treatment of diseases or conditions besides those mentioned above. For example, the compounds of formula I may be useful in the treatment of hypotension associated with septic and/or toxic shock, in the treatment of dysfunction of the immune system, as an adjuvant to short-term immunosuppression in organ transplant therapy, in the treatment of vascular complications associated with diabetes and in cotherapy with cytokines, e.g. TMF or interleukins.

Thus, according to one aspect of the invention, there is provided a miethod of treatment or prophylaxis of one of the above mentioned diseases which comprises administering a therapeutically effective amount of a compound of formula I, or a pharmaceutically acceptable salt thereof, to a patient.

In particular, there is provided a method of treatment or prophylaxis of inflammation, which method comprises administering a therapeutically effective quantity of a compound of formula I, or a pharmaceutically acceptable salt thereof, to a patient suffering from or susceptible to an infammatory condition.

According to a flrter aspect of the invention we provide a compound of formula I or a pharmaceutically acceptable salt thereof for use as a pharmaceutical in the treatment or prophylaxis of the aforementioned diseases or conditions.

According to another feature of the invention we provide the use of a compound of formula I or a pharmaceutically acceptable salt thereof in the manufacture of a medicament for the treatment or prophylaxis of the aforementioned diseases or conditions.

For the above mentioned therapeutic indications, the dosage administered will, of course, vary with the compound employed, the mode of administration and the treatment desired.

The compounds of formula I, and pharmaceutically acceptable salts thereof, may be used on their own, or in the form of appropriate pharmaceutical compositions.

According to the invention, there is also provided a pharmaceutical composition comprising preferably less than 80% and more preferably less than 50% of a compound of formula I, or a pharmaceutically acceptable salt thereof, in admixture with a pharmaceutically acceptable diluent or carrier.

Examples of such diluents and carriers will be well known to a person skilled in the art.

There is also provided a process for the preparation of such a pharmaceutical composition which comprises mixing the ingredients.

The compounds of formula I have the advantage that they are less toxic, are more efficacious, are longer acting, have a broader range of activity, are more potent, are more selective, produce fewer side effects, or are more easily absorbed than compounds of similar structure, or have other useful pharmacological properties.

The invention is illustrated but in no way limited by the following examples:

Preparation of intermediates

EXAMPLE A

2-Aminobenzamidine dihydrochloride (a) 2-Aminobenzamidoxime

A suspension of 2-aminobenzonitrile (10 g, 0.084 mol), sodium methoxide (4.65 g, 0.084 mol) and hydroxylamine hydrochloride (5.88 g, 0.048 mol) in methanol was heated under reflux for 18 hours. The mixture was concentrated to an oil which was partitioned between ethyl acetate and 10% sodium hydroxide solution. The basic phase was separated and extracted three times with ethyl acetate. The combined organic solution was washed three times with saturated brine and dried over magnesium sulphate. Evaporation of the solvent gave the product as an oil which was purified by flash column chromatography on silica gel, eluting with dichloromethane/ethanol as eluant to afford the product as an oil (7.3 g), MS (+FAB) 152 ([M+H]+), 1H NMR (CDCl$_3$) 7.3–6.7 (4H, m), 5.1–4.7 (4H, br, s).

(b) 2-Aminobenzamidine dihydrochloride

A suspension of 2-aminobenzamidoxime (4.0 g, 0.026 mol) and wet Raney nickel (ca. 2 g) in ethanol was stirred under 3 atmospheres of hydrogen at 60° C. for 16 hours. The catalyst was removed by filtration and the solvent evaporated to give the product as an oil which was dissolved in a small amount of ethanol. 1N HCl in ether (60 ml) was added with stirring and the solid produced was collected by filtration to give an off-white powder (4.5 g), m.p. 222°–225° C.

EXAMPLE B

2-Amino-6-chlorobenzamidine dihydrochloride (a) 2-Amino-6-chlorobenzamidoxime is This compound was prepared following the method of Example A, step (a) to give a yellow solid, MS (+CI) 188/186 ([M+H]+), 1H NMR (d$_6$-DMSO) 9.33 (1H, br, s), 7.02 (1H, t, J 8.1 Hz), 6.62 (1H, d, J 10.7 Hz), 6.59 (1H, d, J 8.4 Hz), 5.76 (2H, s), 512 (2H, s).

(b) 2-Amino-6-chlorobenzamidine dihydrochloride

This compound was prepared following the method of Example A, step (b) to give an off-white powder, m.p. 287°–289° C. (dec.).

EXAMPLE C

2-Amino-6-fluorobenzamidine dihydrochloride (a) 2-Amino-6-fluorobenzamidoxime This compound was prepared following the method of Example A, step (a) to give a white solid, m.p. 166°–167° C.

(h) 2-Amino-6-fluorobenzamidine dihydrochloride

This compound was prepared following the method of Example A, step (b) to give pale yellow crystals, m.p. 215°–217° C. (dec.).

EXAMPLE D

2-Amino-6-hydroxybenzamidine dihydrochloride (a) 3-Amino-4-nitrobenz[d]isoxazole To potassium hydroxide (0.58 g, 10.3 mmol) and tert-butyl N-hydroxycarbamate (1.38 g, 10.3 mmol) in DMF (30 iml) was added 2,6-dinitrobenzonitrile (2.0 g, 10.3 nmmol) and the mixture was stirred for 20 h. Water was added. The whole was extracted with ether, the ether was dried (sodium sulphate) and evaporated. Flash column chromatography on silica gel, eluting with ethyl acetate/dichloromethane, gave the product (0.4 g), MS (+CI) 180 ([M+H]+), 1H NMR (CDCl$_3$) 8.13 (1H, d), 7.78 (1H, d), 7.68 (1H, dd), 5.43 (2H, s).

(b) 2-Amino-6-hydroxybenzamidine dihydrochloride

This compound was prepared following the method of Example A, step (b) to give a solid (0.82 g), MS (+ESI) 152 ([M+H]+), 1H NMR (CDCl$_3$) 10.2 (1H, s), 9.13 (1H, s), 8.99 (1H, s), 7.30 (1H, dd), 6.35 (2H, 2d), 6.3 (1H, s).

EXAMPLE E

2-Amino-6-methoxybenzamidine dihydrochloride (a) 2-Amino-6-methoxybenzamidoxime This compound was prepared following the method of example A, step (a) to give a white solid (0.4 g), MS (+EI) 182 ([M+H]+), 1H NMR (d$_6$-DMSO) 9.23 (1H, s), 6.97 (1H, dd), 6.29 (1H, d), 6.20 (1H, d), 5.55 (2H, s), 5.18 (2H, s), 3.67 (3H, s).

(b) 2-Amino-6-methoxybenzamidine dihydrochloride

This compound was prepared following the method of Example A, step (b) to give a solid (0.2 g), MS (+CI) 166 ([M+H]+), 1H NMR (d$_6$-DMSO) 9.15 (2H, s), 8.92 (2H, s), 7.16 (1H, dd), 6.40 (1H, d), 6.31 (1H, d), 5.86 (3H, s), 3.73 (3H, s).

EXAMPLE F

2-Amino-6-(methlthio)benzamnidine dihydrochloride

Trimethylaluminium (2.0M in toluene, 9 ml) was added to ammonium chloride (0.98 g, 18 mmol) in toluene (20 ml) at 5° C. The solution was stirred for 2 h, by which time bubbling had ceased. 2-Amino-6-(methylthio)-benzonitrile (1.0 g, 6.1 mmol) was added and stirred at 80° C. for 20 h. The mixture was cooled, added to alumina (30 g) in chloroform (30 ml) and stirred for 30 min., filtered through celite, evaporated and triturated with ether to give the title intermediate, MS (+FAB) 182 ([M+H]+), 1H NMR (d$_6$-DMSO) 9.33 (1H, s), 9.26 (1H, s), 7.18 (1H, t), 6.63 (1H, d), 6.62 (1H, d), 5.48 (2H, s), 2.43 (3H, s).

EXAMPLE G

2-Amino-3,6-difluorobenzamidine dihydrochloride (a) 2-Amino-3,6-difluorobenzonitrile 2,3,6-Trifluorobenzonitrile (1.76 ml, 15.2 mmol) in aqueous ammonia (20 ml) and acetonitrile (10 ml) was stirred for 7 days. Water was added. The whole was extracted with ether, the ether was dried (sodium sulphate) and evaporated. Flash column chromatography on silica gel, eluting with dichloromethane, gave the product (1.2 g), MS (+EI) 154 (M+), 1H NMR (CDCl$_3$) 7.07–7.16 (1H, m), 6.36–6.43 (1H, m), 4.62 (2H, s).

(b) 2-Amino-3,6-difluorobenzamidoxime

This compound was prepared following the method of Example A, step (a) to give a solid (1.15 g), MS (+EI) 187 (M+), 1H NMR (CDCl$_3$) 6.9 (1H, s), 6.9 (1H, ddd), 6.36 (1H, ddd), 5.15 (4H, s).

(c) 2-Amino-3,6-difluorobenzamidine hydrochloride

This compound was prepared following the method of Example A, step (b) to give a solid (1.12 g), MS (+CI) 172 ([M+H]+), 1H NMR (d$_6$-DMSO) 9.48 (2H, s), 9.16 (2H, s), 7.25 (1H, ddd), 6.46 (1H, dt), 6.00 (2H, s).

EXAMPLE H

2-Amino-4,6-difluorobenzamidine dihydrochloride (a) 2-Amino-4,6-difluorobenzonitrile This compound was prepared following the method of Example G, step (a) to give an orange solid (1.5 g), MS (APCI-) 153 (M–H), 1H NMR (CDCl$_3$) 6.18–6.29 (2H, m), 4.70 (1H, s), 4.48 (1H, s).

(b) 2-Amino-4.6-difluorobenzamidoxime

This compound was prepared following the method of Example A, step (a) to give a solid, MS (+CI) 188 ([M+H]+), 1H NMR (CDCl$_3$) 6.33 (1H, s), 6.10–6.22 (2H, m), 517 (2H, s), 5.07 (2H, s).

(c) 2-Amino-4,6-difluorobenzamidine dihydrochloride

This compound was prepared following the method of Example A, step (b) to give a white solid (0.64 g), MS (+CI) 172 ([M+H]+), 1H NMR (d$_6$-DMSO) 9.40 (2H, s), 9.11 (2H, s), 6.49 (1H, dt), 6.36 (1H, d), 5.01 (2H, s).

EXAMPLE I

2-Amino-3-chloro-6-fluorobenzamidine dihydrochloride (a) 3-Chloro-2,6-difluorobenzaldehyde n-Butyllithium (1.43M in hexane, 20.2 mmol, 14.1 ml) was added dropwise at 0° C. to a solution of diisopropylamine (2.91 ml, 22.2 mmol) in THF (80 ml). After 30 min. at 0° C., the solution was cooled to –78° C. and 1-chloro-2,4-difluorobenzene (3 g, 20.2 mmol) in THF (10 ml) added dropwise. After 30 min., 4-formylmorpholine (4.1 ml) was added and the mixture warmed to room temperature over 1 h, diluted with 1N HCl, extracted twice with ethyl acetate, the extracts washed with brine, dried over sodium sulphate and evaporated to give a mobile yellow oil (2.2 g), MS (+EI) 178/177/176/175 (M+), 1H NMR (CDCl$_3$) 10.34 (1H, s), 7.66–7.60 (1H, m), 7.00 (1H, dt, J6.9 Hz, 1.2 Hz).

(b) 3-Chloro-2,6-difluorobenzonitrile

A suspension of 3-chloro-2,6-difluorobenzaldehyde (2.10 g, 11.9 mmol) and hydroxylamine-O-sulphonic (1.9 g, 17 mmol) in water (60 ml) was heated at 80° C. for 16 h, cooled, extracted twice with ethyl acetate, extracts washed with brine dried over sodium sulphate and evaporated to afford the product as a yellow solid (2.1 g), MS (+EI) 175/173 (M+); 1H NMR (CDCl$_3$) 7.39 (1H, dd, J5.7, 9.0 Hz), 6.46 (1H, dd, J8.4, 9.0 Hz), 4.95 (2H, br. s).

(c) 2-Amino-3-chloro-6-fluorobenzonitrile

Aqueous ammonia (d 0.880, 2 ml) was added to a solution of 3-chloro-2,6-difluorobenzonitrile (1.93 g, 11.1 mmol) in acetonitrile (10 ml), and the mixture heated to 60° C. for 16 h. The resulting brown solution was evaporated and purified by flash chromatography eluting with 5% ethyl acetate/hexane, increasing the gradient to 20% ethyl acetate/hexane, to furnish a white solid (410 mg), MS (+EI) 173/171 (M+); 1H NMR (CDCl$_3$) 7.39 (1H, dd, J5.7, 9.0 Hz), 6.46 (1H, t, J8.7 Hz), 4.95 (2H, br. s).

(d) 2-Amino-3-chloro-6-fluorobenzamidoxime

This was prepared from 2-amino-3-chloro-6-fluorobenzonitrile by the method of Example A, step (a) to give a white solid, MS (+CI) 206/204 ([M+H]+), 1H NMR (d$_6$-DMSO) 9.61 (1H, s), 7.27 (1H, dd, J5.4, 8.7 Hz), 6.45 (1H, dd, J9.0, 9.6 Hz), 5.93 (2H, s), 5.57 (2H, s).

(e) 2-Amino-3-chloro-6-fluorobenzamidine dihydrochloride

This was prepared from 2-amino-3-chloro-6-fluorobenzamidoxime by the method of Example A step (b) to give an off-white solid, MS (+CI) 190/188 ([M+H]+); 1H NMR (d$_6$-DMSO) 9.52 (2H, s), 9.26 (2H, s), 7.47 (1H, dd, J6.0, 9.0 Hz), 6.57 (1H, t, J9.0 Hz), 6.07 (1H, br. s), 3.56 (2H, br. s).

EXAMPLE J 2-(Methylamino)benzamidine dihydrochloride (a) N-(2-Cyanophenyl)-2,2,2-trifluoroacetamide Trifluoroacetic anhydride (5.9 ml, 0.04 mol) was added to 2-aminobenzonitrile (5 g, 0.04 mol) in dichloromethane (200 ml) and stirred for 16 h. Dichloromethane (200 ml) was added and the solution washed with brine, dried (sodium sulphate) and evaporated to give the product as a white solid (8 g), MS (EI) 214 (M+), 1H NMR (CDCl$_3$) 8.35 (2H, d), 7.71 (1H, s), 7.71 (1H, dd), 7.36 (1H, dd).

(b) N-(2-Cyanophenyl)-2,2,2-trifluoro-N-methylacetamide

N-(2-Cyanophenyl)-2,2,2-trifluoroacetamide (3 g, 0.014 mol) was added to sodium hydride (60% in oil, 0.62 g, 0.026 mol) in THF (40 ml) under nitrogen and stirred for 4 h. Methyl iodide (8.7 ml, 0.14 mol) was added and stirring continued overnight. The mixture was poured onto brine and extracted with ethyl acetate, dried over sodium sulphate and evaporated to give the product (3 g), MS (+EI) 228 (M+). 1H NMR (CDCl$_3$) 7.8 (1H, d), 7.7 (1H, dd), 7.4 (1H, dd), 7.4 (1H, d), 3.43 (3H, s).

(c) 2-(Methylamino)benzonitrile

N-(2-Cyanophenyl)-2,2,2-trifluoro-N-methylacetamide (3 g, 0.01 mol) was dissolved in a sodium bicarbonate/water/ethanol mixture, refluxed for 5 h and evaporated. Water was added and the mixture extracted with ethyl acetate, dried over sodium sulphate and evaporated to give the product (2.5 g). MS (+EI) 132 (M+), 1H NMR (CDCl$_3$) 7.45 (2H, t), 6.69 (1H, d), 6.62 (1H, t), 6.19 (1H, s), 2.76 (3H, d).

(d) 2-(Methylamino)benzamidoxime

This compound was prepared following the method of Example A, step (a) to give a brown oil (1.4 g), MS (+EI) 166 ([M+H]+), 1H NMR (CDCl$_3$) 9.66 (1H, s), 7.44 (2H, t), 7.16 (1H, t), 6.6 (2H, t), 5.78 (1H, d), 2.78 (3H,d)

(e) 2-(Methylamino)benzamidine dihydrochloride

This compound was prepared following the method of Example A, step (b) to give a solid (1.14 g), MS (+EI) 149 (M+).

EXAMPLE K

2-Fluoro-6-(methylamino)benzamidine dihydrochloride (a) N-(2-Cyano-3-fluorophenyl)-2,2,2-trifluoroacetamide This compound was prepared following the method of Example J, step (a) to give a white solid (10.6 g), m.p. 134°–136° C.

(b) N-(2-Cyano-3-fluorophenyl)-2,2,2-trifluoro-N-methylacetamide

This compound was prepared following the method of Example J, step (b) to give an impure brown solid (3.7 g) which was used crude, MS (+EI) contains 246 (M+).

(c) 2-Fluoro-6-(methylamino)benzonitrile

This compound was prepared following the method of Example J, step (c) to give is colourless platelets (2.0 g), MS (+EI) 150 (M+), 1H NMR (CDCl$_3$) 7.35 (1H, q), 6.42 (2H, m), 4.74 (1H, s), 2.94 (3H, d).

(d) 2-Fluoro-6(methylamino)benzamidoxime

This compound was prepared following the method of Example A, step (a) to give a waxy solid (1.0 g), MS (+EI) 183 (M+), 1H NMR (CDCl$_3$) 7.18 (1H, q), 6.39 (2H, m), 5.07 (1H, d), 5.07 (1H, s), 2.82 (3H, s).

(e) 2-Fluoro-6-(methylamino)benzamidine dihydrochloride

This compound was prepared following the method of Example A, step (b) to give colourless platelets (1.1 g), MS (+CI) 168 ([M+H]+), 1H NMR (d$_6$-DMSO) 9.48 (2H, s), 9.38 (2H, s), 7.36 (1H, q), 6.51 (2H, m), 2.73 (3H, s).

EXAMPLE L 2-(2-Azidoethyl)benzaldehyde ethylene acetal (a) 2-Vinylbenzaldehyde ethylene acetal A mixture of 2-vinylbenzaldehyde (2.9 g, 22 mmol) and trimethylsilyl chloride (11 ml) in ethylene glycol (95 ml) was stirred for 16 h, diluted with saturated sodium bicarbonate solution, extracted with ether, dried over sodium sulphate and evaporated to afford a colourless oil (2.7 g), MS (+EI) 176 (M+), 1H NMR (CDCl$_3$) 7.57 (1H, m), 7.53 (1H, dd, J1.5, 7.5 Hz), 7.36–7.30 (2H, m), 7.14 (1H, dd, J11, 17.4 Hz), 6.04 (1H, s) 5.69 (1H, dd, J1.3, 17.4 Hz), 5.34 (1H, dd, J1.3, 11.0 Hz), 4.18–4.04 (2H, m), 3.77–3.65 (2H, m).

(b) 2-(2-Hydroxyethyl)benzaldehyde ethylene acetal

Borane-dimethyl sulphide complex (2.0M in THF, 7.67 ml, 15.3 mmol) was added dropwise to 2-vinylbenzaldehyde ethylene acetal (2.7 g, 15.3 mmol) in THF (80 ml) at 0° C. Stirring was continued at room temperature for 4 h, cooled to 0° C. and 10% aqueous sodium hydroxide (3 ml) added dropwise, followed by hydrogen peroxide (30% by volume, 1.8 ml). After 1 h at room temperature, the mixture was diluted with water, extracted with ethyl acetate, dried over sodium sulphate and evaporated to give a colourless viscous gum (2.2 g), MS (+EI) 194 (M+), 1H NMR (CDCl$_3$) 7.48 (1H, d, J6 Hz), 7.3–7.1 (3H, m), 5.91 (1H, s), 4.1–3.9 (4H, m), 3.78 (2H, t, J6.5 Hz), 2.93 (2H, t, J6.5 Hz).

(c) 2-(2-(4-Methylphenylsulphonyloxy)ethyl)benzaldehyde ethylene acetal p-Toluenesulphonyl chloride (4.4 g, 23 mmol) was added portionwise to a solution of 2-(2-hydroxy)ethylbenzaldehyde ethylene acetal (4.47g., 23 mmol) in pyridine (50 ml) and the mixture stood at 0° C. for 16 h, diluted with water, extracted twice with ether, the extracts washed twice with ice-cold 4N aqueous HCl, followed by saturated sodium bicarbonate, dried over sodium sulphate and evaporated to give the product as a colourless gum (2.4 g), MS (+FAB) 349 ([M+H]+), 1H NMR (CDCl$_3$) 7.72 (2H, d, J7 Hz), 7.53–7.23 (5H, m), 7.14–7.12 (1H, m), 5.82 (1H, s), 4.29–4.16 (2H, m), 4.1–3.95 (4H, m), 3.11 (2H, d, J6.3 Hz), 2.56 (3H, s).

(d) 2-(2-Azidoethyl)benzaldehyde ethylene acetal

A solution of 2-(2-(4-methylphenylsulphonyloxy)ethyl)benzaldehyde ethylene acetal (1.43 g, 4.10 mmol) and sodium azide (0.53 g, 8.2 mmol) in DMSO (20 ml) was stirred for 16 h, diluted with water, extracted three times with ether, washed with brine, dried over sodium sulphate and evaporated to afford the product as a yellow oil (0.86 g), MS (+EI) 190 [(M–NH$_2$)+], 1H NMR (d$_6$-DMSO) 7.53–7.25 (4H, m), 5.92 (1H, s), 4.19–3.95 (4H, m), 3.53 (2H, t, J7.2 Hz), 2.98 (2H, t, J7.2 Hz).

EXAMPLE M

Ethyl N-(4,4-diethoxybutyl)carbamate

Ethyl chloroformate (0.3 ml, 3.1 mmol) was added dropwise to a solution of 4-aminobutanal diethyl acetal (0.5 ml, 2.9 mmol) and pyridine (0.28 ml, 3.5 mmol) in dichloromethane (10 ml) at 5° C. The mixture was stirred for 30 min. Water was added and the mixture was extracted with ether. The ether was dried (sodium sulphate) and evaporated to give the product as a yellow oil, MS (+EI) 232 ([M–H]+), 1H NMR (CDCl$_3$) 4.69 (1H, s), 4.4 (1H, t), 4.00 (2H, q), 3.5–3.65 (2H, m), 3.35–3.5 (2H, m), 3.05–3.15 (2H, m), 1.5–1.6 (4H, m), 1.1–1.2 (9H, m).

EXAMPLE N

Ethyl N-(3,3-diethoxypropyl)carbamate

This was prepared following the method of Example M, MS (+EI) 174 ([M–OEt]+), 1H NMR (CDCl$_3$) 5.05 (1H, s), 4.55 (1H, t), 4.05–4.15 (2H, m), 3.6–3.72 (2H, m), 3.45–3.57 (2H, m), 3.2–3.32 (2H, m), 1.28–1.38 (2H, m), 1.2–1.3 (9H, m).

EXAMPLE O

Ethyl N-(2,2-dimethoxyethyl)carbamate

This was prepared following the method of Example M, MS (+EI) 146 ([M–OMe]+), 1H NMR (CDCl$_3$) 4.84 (1H, s), 4.38 (1H, t), 4.11 (2H, q), 3.6 (6H, s), 3.32 (2H, t), 125 (3H, t).

EXAMPLE P

Ethyl 2-formyl-1H-pyrrole-1-arboxylate

2-Pyrrolecarboxaldehyde (1.0 g, 10.5 mmol) was added to sodium hydride (50% in oil, 0.5 g, 10.5 mmol) in DMF at 0° C. Stirred at room temp. for 1 h, ethyl chloroformate (1.0 ml, 10.5 mmol) added and stirred for 20 h. Water was added and the mixture was extracted with ether. The ether was dried (sodium sulphate) and evaporated to give the product as a solid, m.p. 218°–220° C.

EXAMPLE Q

Ethyl 3-formyl-1H-pyrrole-1-carboxylate 2,5-Dimethoxy-3-tetrahydrofiirancarboxaldehyde (2.0 g, 12 mnmol) and urethane (1.1 g, 12 mmol) were refluxed in acetic acid (20 ml) for 1 h. The solution was cooled, diluted with water, extracted three times with ether, dried over magnesium sulphate and evaporated. Purification by flash chromatography on silica eluting with 20% ethyl acetate/hexane gave the product as an oil (0.25 g), MS (+EI) 167 (M+).

EXAMPLE R

Ethyl 3-oxopyrrolidine-1-carboxylate (a) Ethyl 3-hydroxypyrrolidine-1-carboxylate This was prepared following the method of Example M (using DMAP not pyridine), MS (+EI) 159 (M+), 1H NMR (d$_6$-DMSO) 4.92 (1H, t), 4.23 (1H, s), 4.00 (2H, q), 3.25–3.4 (3H, m), 3.15 (1H, d), 1.70–1.95 (2H, m), 1.17 (3H, t).

(b) Ethyl 3-oxopyrrolidine-1-crboxylate

To the above alcohol (0.43 img, 2.7 mmol) in ether (12 ml) at 0° C. was added Jones reagent portionwise until no alcohol remained. Water was added and the mixture was extracted with ether. The ether extract was dried (sodium sulphate) and evaporated to give the product, MS (+EI) 157 (M+), 1H NMR (CDCl$_3$, rotamers) 4.39 (1H, q), 4.1–4.25 (3H, m), 3.96 (1H, t), 3.7–3.9 (5H, m), 3.3–3.6 (2H, m), 2.5–2.7 (4H, m), 1.2–1.4 (6H, m).

EXAMPLE S 1-(1-Oxobutyl)-4-piperidone ethylene ketal

Butyryl chloride (0.53 g, 5 mmol) in dry dichloromethane (5 ml) was added dropwise with stirring to 4-piperidone ethylene ketal (0.72g, 5 mmol) and pyridine (0.5 ml) in dry dichloromethane (10 ml). The solution was stirred at 20° C. overnight then washed successively with dilute HCl, saturated sodium bicarbonate solution and water and dried (sodium sulphate). Evaporation of the solvent gave the product as a clear syrup (0.66 g). MS (+EI) 213 (M+), 1H NMR (CDCl$_3$) 3.98 (4H, s), 3.70 (2H, t), 3.53 (2H, t), 2.33 (2H, t), 1.61–1.83 (6H, m), 0.97 (3H, t).

EXAMPLE T 1-(4-Methylbenzoyl)-4-piperidone ethylene ketal

To a solution of 4-piperidone ethylene ketal (1.43 g, 10 mimol) and triethylamine (10 mmol, 1.4 ml) was added dropwise a solution of 4-methylbenzoyl chloride (1.55 g, 10 mmol) in ethyl acetate (20 ml) and the mixture stirred for 2 h. The mixture was washed twice with water followed by brine, dried over sodium sulphate and evaporated to give an off-white solid, m.p. 59°–61° C.

EXAMPLE U

The following compounds were prepared from 4-piperidone ethylene ketal and the appropriate acyl chloride by the method of Example T (a) 1-(4-Methoxybenzoyl)4-piperidone ethylene ketal, colourless solid; m.p. 58°–59° C.

(b) 1-(4-Cyanobenzoyl)-4-piperidone ethylene ketal, off-white solid; m.p. 122°–123° C.

(c) 1-(4-Nitrobenzoyl)-4-piperidone ethylene ketal, pale yellow solid; m.p. 120°– 121° C.

(d) 1-(2-Furylcarbonyl)-4-piperidone ethylene ketal, colourless solid; m.p. 78°–79° C.

(e) 1-(4-Ethylbenzoyl)-4-piperidone ethylene ketal, pale yellow oil; MS (+EI) 275 (M+).

(f) 1-(4-Chlorobenzoyl)-4-piperidone ethylene ketal, off-white solid; m.p. 106°–107° C.

(g) 1-(2-Nitrobenzoyl)-4-piperidone ethylene ketal, pale yellow solid; m.p. 78°–79° C.

(h) 1-(3-Nitrobenzoy)-4piperidone ethylene ketal, pale yellow solid; m.p. 129°–130° C.

(i) 1-(2-Methylbenzoyl)-4-piperidone ethylene ketal, colourless oil; MS (+EI) 261 (M+).

(j) 1-(3-Methylbenzoyl)4-piperidone ethylene ketal, orange oil; MS (+EI) 261 (M+).

(k) 1-(2-Thienylcarbonyl)-4-piperidone ethylene ketal, yellow solid; m.p. 97°–99° C.

(l) 1-(4-Acetoxybenzoyl)-4=piperidone ethylene ketal, beige solid; MS (+EI) 305 (M+).

(m) 1-(3-Acetoxybenzoyl)-4-piperidone ethylene ketal, beige solid; MS (+EI) 305 (M+).

(n) 1-(5-Isoxazolylcarbonyl)-4-piperidone ethylene ketal, yellow solid; MS (+EI) 238 (M+).

EXAMPLE V 1-(5-Bromo-2-furylcarbonyl)-4-piperidone ethylene ketal 1,1'-Carbonyldiimidazole (356 mg, 2.2 mmol) was added to 5-bromofuiroic acid (383 mg, 2 mmol) in DMF (6 ml) and the solution stirred at room temperature for 30 min. 4-Piperidone ethylene ketal (0.26 ml, 2 mmol) was added dropwise and stirring was continued for 30 min. The solution was diluted with water and extracted with ethyl acetate. The organic extracts were washed with brine, dried over sodium sulphate and evaporated to give a white solid (614 mg), MS (+EI) 317/315 (M+).

EXAMPLE W

The following compounds were prepared from 4-piperidone ethylene ketal and the appropriate carboxylic acid by the method of Example V (a) 1-(4-(1,2,3-Thiadiazol-4-yl)benzoyl)-4-piperidone ethylene ketal, white solid; MS (+EI) 331.

(b) 1-(4-(Bromobenzoyl)-4-piperidone ethylene ketal, colourless oil; MS (+EI) 327/325.

(c) 1-(4-(Iodobenzoyl)-4-piperidone ethylene ketal, off-white solid; m.p. 109°–111° C.

(d) 1-(4-(Trifluoromethyl)benzoyl)-4-piperidone ethylene ketal, off-white solid; m.p. 93°–94° C.

(e) 1-(4-(Methanesulphonyl)benzoyl)-4-piperidone ethylene ketal, off-white solid; MS (+EI) 325 (M+).

(f) 1-(4-Fluorobenzoyl)-4-piperidone ethylene ketal, off-white solid; m.p. 74°–75° C.

(g) 1-([1,1'-Biphenyl]-4-ylcarbonyl)-4-piperidone ethylene ketal, off-white solid; m.p. 138°–139° C.

(h) 1-(4-(Aminosulphonyl)benzoyl)-4-piperidone ethylene ketal, off-white solid; m.p. 228°–230° C.

(i) 1-(3-Pyridylcarbonyl)-4-piperidone ethylene ketal, off-white solid; m.p. 93°–94° C.

(j) 1-(5-Chloro-2-thienylcarbonyl)-4-piperidone ethylene ketal, yellow oil; MS (+EI) 287/289 (M+).

(k) 1-(3-Amino-4-chlorobenzoyl)-4-piperidone ethylene ketal, off-white solid; m.p. 139°–140° C.

(l) Methyl 4-(4-oxopiperidinocarbonyl)benzoate ethylene ketal, white solid; MS (+EI) 305 (M+).

(m) 1-(4-(1H-pyrrol-1-yl)benzoyl)-4-piperidone ethylene ketal, beige solid; MS (+EI) 312 (M+).

(n) 1-(6-Chloro-3-pyridylcarbonyl)-4-piperidone ethylene ketal, pale yellow solid; MS (+EI) 282 (M+).

(o) 1-(5-Bromo-3-thienylcarbonyl)-4-piperidone ethylene ketal, colourless oil; MS (+EI) 353 (M+).

(p) 1-(4-(Phenylmethoxy)benzoyl)-4-piperidone ethylene ketal, colourless oil; MS (+EI) 353 (M+).

(q) 1-(4-(4,4-Dimetbyloxazolin-2-yl)benzoyl)-4-piperidone ethylene ketal, yellow solid; MS (+FAB) 345 ([M+H]+).

(r) 1-(2-Pyridylcarbonyl)-4-piperidone ethylene ketal, pale green oil, MS (+EI) 248 (M+).

(s) 1-(4-Pyridylcarbonyl)-4-piperidone ethylene ketal, pale green oil, MS (+EI) 248 (M+).

(t) 1-(3-Pyrdazinylcarbonyl)-4-piperidone ethylene ketal, off-white powder, MS (+EI) 249 (M+).

(u) 1-(3,5-Dimethylbenzoyl)-4-pipenidone ethylene ketal, colourless oil, MS (+EI) 275 (M+).

(v) 1-(3-Fluoro-4-methylbenzoyl)-4-piperidone ethylene ketal, white powder, m.p. 85.5°–88° C.

(w) 1-(3,5-Difluorobenzoyl)-4piperidone ethylene ketal, white powder, m.p 95°–97° C.

(x) 1-(3,4Dichlorobenzoyl)-4-piperidone ethylene ketal, colourless solid, MS (+EI) 315 (M+).

(y) 1-(4Bromo-2-thienylcarbonyl)-4-piperidone ethylene ketal, colourless oil, MS (+EI) 333/331 (M+).

(z) 1-(5-Benzofuroxanylcarbonyl)-4-piperidone ethylene ketal, yellow gum, MS (+EI) 305 (M+).

(aa) 1-(2-Pyrazinylcarbonyl)-4-piperidone ethylene ketal, colourless solid, MS (+EI) 249 (M+).

(bb) 1-(4-(Trifluoromethoxy)benzoyl)-4-piperidone ethylene ketal, colourless viscous oil, MS (+EI) 331 (M+).

(cc) 1-(5-(1,3-Benzodioxolyl)carbonyl)-4-piperidone ethylene ketal, pale yellow gum, MS (+EI) 291 (M+).

(dd) 1-((1,3-Dihydro-1,3-dioxo-2H-isoindol-5-yl)carbonyl)-4-piperidone ethylene ketal, white solid, MS (+EI) 316 (M+).

(ee) 1-(3-Thienylcarbonyl)-4-piperidone ethylene ketal, colourless oil, MS (+CI) 254 ([M+H]+).

(ff) 1-(5-Methyl-2-pyrazinyicarbonyl)-4-piperidone ethylene ketal, colourless viscous oil, MS (+EI) 263 (M+).

(gg) 1-(6-Quinolyl)carbonyl-4-piperidone ethylene ketal, white solid, MS (+CI) 299 ([M+H]+).

(hh) 1-(4-Ethynylbenzoyl)-4-piperidone ethylene ketal, pale orange solid, MS (+EI) 271 (M+).

(ii) 1-(4-Phenoxybutanoyl)-4-piperidone ethylene ketal, colourless oil, MS (+CI) 306 ([M+H]+).

(jj) 1-(2-Thiazolylcarbonyl)-4-piperidone ethylene ketal, yellow solid, MS (+CI) 255 ([M+H]+).

(kk) 1-(((2-Trifluoromethyl)phenyl)acetyl)-4-piperidone ethylene ketal, pale yellow solid, m.p. 65°–67° C.

(ll) 1-(1-Methyl-2-pyrrolylcarbonyl)-4-piperidone ethylene ketal, brown oil, MS (+EI) 250 (M+).

(mm) 1-(2-(5-Methylthienylcarbonyl))-4-piperidone ethylene ketal, yellow oil, MS (+CI) 268 ([M+H]+).

(nn) 1-(2-Fluorobenzoyl)-4-piperidone ethylene ketal, colourless solid, m.p. 90°–92° C.

(oo) 1-(3-Isoxazolylcarbonyl)-4-piperidone ethylene ketal, pale yellow oil, MS (+EI) 238 (M+).

(pp) 1-(2-(3-Bromo-2-thienyl))-5-thiazolylcarbonyl))-4-piperidone ethylene ketal, yellow solid, MS (+CI) 239 ([M+H]+).

(qq) 1-(2-Napthylcarbonyl)-4-piperidone ethylene ketal, m.p. 96°–98° C.

(rr) 1-(4-Chloro-3-iodobenzoyl)-4-piperidone ethylene ketal, MS (+EI) 407/409 (M+).

(ss) 1-(4-Ethylbenzoyl)-4-piperidone ethylene ketal, colourless oil, MS (+EI) 275 (M+).

(tt) 1-(4-Propylbenzoyl)-4-piperidone ethylene ketal, colourless oil, MS (+EI) 289 (M+).

(uu) 1-(4-Butylbenzoyl)-4-piperidone ethylene ketal, colourless oil, MS (+EI) 303 (M+).

(vv) 1-(4-Isothiazolylcarbonyl)-4-piperidone ethylene ketal, pale brown oil, MS (+CI) 255 [(M+H)+].

(ww) 1-(1,2,3-Thiadiazol-4-ylcarbonyl)-4-piperidone ethylene ketal, pale yellow solid, MS (+EI) 255 (M+).

(xx) 1-(2-Benzo[b]thienylcarbonyl)-4-piperidone ethylene ketal, pale orange solid, m.p. 103°–104 ° C.

(yy) 1-(5-Ethyl-2-thienylcarbonyl)-4-piperidone ethylene ketal, (this was prepared from 5-ethylthiophene-2-carboxylic acid: D. W. Knight and A. P. Nott, *J. Chem. Soc., Perkin Trans.* 1, 1983, 791) yellow oil, MS (+CI) 282 ([M+H]+).

(zz) 1-(5-Bromo-2-thienylcarbonyl)-4-piperidone ethylene ketal, pale yellow solid m.p.92°–94° C.

EXAMPLE X 1-(2,2,2-Trifluoroacetyl)-4-piperidone ethylene ketal

Trifluoroacetic anhydride (1.47 g, 7.0 mmol) was added to a solution of 4-piperidone ethylene ketal (1.0 g, 7.0 mmol) in acetonitrile (20 ml) and stirred for 4 h. Water was added and the mixture extracted with ethyl acetate, the organic layer dried over sodium sulphate and evaporated to give the product, MS (+EI) 239 (M+), 1H NMR (CDCl$_3$) 3.99 (s, 4H), 3.79 (2H, dd), 3.67 (2H, dd), 1.77 (4H, dd).

EXAMPLE Y 1-(4-Cyano-3-methylbenzoyl)-4-piperidone ethylene ketal (a) 4-Cyano-3-methylbenzoic acid n-Butyl lithium (1.38M in hexane, 5.54 ml, 7.65 mmol) was added dropwise to a solution of 2-methyl-4-bromobenzonitrile (1.5 g, 7.65 mmol) in THF (40 ml) at −100° C. The resulting dark red solution was stirred for 5 min., quenched by the cautious addition of solid carbon dioxide and warmed to room temperature. The solution was diluted with 10% aqueous sodium hydroxide and extracted with ethyl acetate. The aqueous layer was acidified with ice-old 4N aqueous HCl, extracted with dichloromethane and the extracts dried over sodium sulphate and evaporated to furnish a white solid (880 mg), MS (+EI) 233 ([M+TMS]+), 1H NMR (d$_6$-DMSO) 13.50 (1H, br. s), 8.00 (1H, s), 7.92–7.86 (2H, m), 2.55 (3H, s).

(b) 1-(4-Cyano-3-methylbenzoyl)-4-piperidone ethylene ketal

This was prepared by the method of Example V, off-white solid, MS (+EI) 286 (M+).

EXAMPLE Z 1-(4-Cyano-3-fluorobenzoyl)-4-piperidone ethylene ketal

Using the method of Example Y, the following compounds were prepared.

(a) 4-Cyano-3-fluorobenzoic acid, MS (+EI) 165 (M+), 1H NMR (CDCl$_3$) 8.04 (1H, d, J 10.2 Hz), 7.97 (1H, d, J 10.2 Hz), 7.78 (1H, dd, J 6.2, 8.0 Hz).

(b) 1-(4-Cyano-3-fluorobenzoyl)-4-piperidone ethylene ketal, waxy yellow solid, MS (+EI) 290 (M+).

EXAMPLE AA

N-(2-Hydroxyphenyl)-4-(4-oxopiperidinocarbonyl)benzamide ethylene ketal (a) 4-(4-Oxopiperdin-1-ylcarbonyl)benzoic acid ethylene ketal A solution of methyl 4-(4-oxopiperidinocarbonyl)benzoate ethylene ketal (1.5 g, 4.9 mmol) and lithium hydroxide monohydrate (309 mg, 7.4 mmol) in THF/water (1:1) (50 ml) was stirred for 18 h, then acidified with dilute HCl. The product was extracted into ethyl acetate, and the extracts dried over sodium sulphate and concentrated to leave a white solid (1.4g), MS (+CI) 292 ([M+H]+), 1H NMR (CDCl$_3$) 8.10 (2H, d, J 8.2 Hz), 7.45 (2H, d, J 8.3 Hz), 3.99 (4H, s), 3.86 (2H, br. s), 3.44 (2H, br. s), 1.81 (2H, br. s), 1.65 (2H, br. s)

(b) N-(2-Hydroxyphenyl)-4-(4-oxopiperidinocarbonyl)benzamide ethylene ketal

A solution of 4-(4-oxopiperidinocarbonyl)benzoic acid ethylene ketal (291 mg, 1 mmol) in DMF (3 ml) was treated with 1,1'-carbonyldiimidazole (162 mg, 1 mmol) and stirred for 30 min. 2-Aminophenol (109 mg, 1 mmol) was added and stirring continued for 22 h. The mixture was acidified with dilute HCl, extracted with ethyl acetate, washed with brine, dried over sodium sulphate and concentrated under vacuum. The residue was purified by flash column chromatography on silica, eluting with ethyl acetate, to furnish a clear glass, MS (+CI) 383 ([M+H]+).

EXAMPLE BB

N-(4-Methoxyphenyl)-4-(4-oxopiperidinocarbonyl) benzamide ethylene ketal

This was prepared by the method of Example AA step (b) to give a white foam, MS (+CI) 397 ([M+H]+).

EXAMPLE CC 1-(4-(2-Thiazolyl)benzoyl)-4-piperidone ethylene ketal

A solution of 1-(4-bromobenzoyl)-4-piperidone ethylene ketal (652 mg, 2 mmol) and trimethyl-2-thiazolylstannane (595 mg, 2.4 mmol) in degassed toluene was heated at reflux with tetrakis(triphenylphosphine)palladium(0) (200 mg, 0.17 mmol) for 16 h. The mixture was cooled, filtered through celite and evaporated. The residue was purified by flash chromatography on silica eluting with 50% ethyl acetate/hexane to yield a white solid (480 mg), MS (+CI) 331 [(M+H)+].

EXAMPLE DD 1-(1-H-Pyrrol-2-ylcarbonyl)-4-piperidone ethylene ketal (a) 1-(1H-Pyrrole-2-carbonyl)imidazole A solution of 1-(t-butoxycarbonyl)pyrrole-2-carboxylic acid (W. Chen, M. P. Cava, Tetrahedron Lett. 1987, 28, 6025) (2.34 g, 10 mmol) in DMF (20 ml) was treated with 1,1'-carbonyldiimidazole (1.62 g, 10 mmol). After 30 min., 4-piperidone ethylene ketal (1.28 ml, 10 mmol) was added dropwise and stirring continued for 90 min. The mixture was diluted with water, extracted with ethyl acetate, washed with water and brine, dried over sodium sulphate and evaporated. The residue was purified by flash chromatography on silica eluting with dichloromethane/ethyl acetate (3:1, increasing the gradient to 1:1) to give a light brown solid (0.54 g), MS (+CI) 162 ([M+H]+).

(b) 1-(1-H-Pyrrol-2-ylcarbonyl)-4-piperidone ethylene ketal

A solution of 1-(1H-pyrrole-2-carbonyl)imidazole (0.54 g, 3.4 mnmol) and 4-piperidone ethylene ketal (0.43 ml, 3.4 mmol) in THF (10 ml) was heated at reflux for 1 h. The mixture was cooled and evaporated, diluted with ethyl acetate, washed with dilute HCl, dried over sodium sulphate and evaporated to afford a beige solid (0.56 g), MS (+CI) 237 ([M+H]+), 1H NMR (CDCl$_3$) 9.47 (1H, br. s), 6.92 (1H, m), 6.53 (1H, m), 6.25 (1H, m), 4.00 (4H, s), 3.91 (4H, t, J 5.4 Hz), 1.78 (4H, t, J 5.8 Hz).

EXAMPLE EE 1-(1H-Imidazole-1-ylcarbonyl)-4-pilperidone ethylene ketal

A solution of 4-piperidone ethylene ketal (1.43 g, 10 mmol) and 1,1'-carbonyldiimidazole (1.62 g, 10 mmol) in dichloromethane (35 ml) was stirred at 20° C. for 2 h. The solution was washed with water (50 ml) and the organic phase evaporated. The residue was recrystallised from toluene to give the title compound (1.85 g) as needles, m.p. 126–128° C.

EXAMPLE FF 3-(Methylthio)propyl 4-piperidone-1-carboxylate ethylene ketal

To 3-(methylthio)-1-propanol (1.3 g, 12.3 mmol) in acetonitrile (50 ml) was added 1,1'-carbonyldiimidazole (2 g, 12.3 mmol) and the resulting solution was stirred for 5 h. 4-Piperidone ethylene ketal (1.77 g, 12.3 mmol) was added and the solution heated at 60° C. for 20 h. After cooling the solvent was evaporated to give the product, MS (+EI) 275 (M+), 4.06 (2H, m), 3.9 (4H, s), 3.43 (4H, t), 2.51 (2H, t), 1.99 (3H, s), 1.84 (2H, m), 1.56

EXAMPLE GG 3-(Methanesulphonyl)propyl 4-piperidone-1-carboxylate ethylene ketal To 1-(3-(Methylthio)propoxycarbonyl)-4-piperidine ethylene ketal (Example FF, 1 g, 3.6 mmol) in acetone (100 ml) and water (10 ml) was added OXONE™ (12.9 g, 5.8 equiv.) and the resulting mixture was stirred for 20 h. then poured onto 10% aq. sodium bisulphite and extracted with ethyl acetate. The extract was dried (sodium sulphate) and evaporated to give the product, MS (+CI) 308 ([M+H]+), 1H NMR (CDCl$_3$) 4.09 (2H, m), 3.9 (4H, s), 3.44 (4H, m), 3.16 (2H, m), 2.99 (3H, s), 2.00 (2H, m), 1.57 (4H, t).

EXAMPLE HH

O-Ethyl 4-oxopiperidine-1-carbothioate ethylene ketal

Sodium hypochlorite (1M in 0.1N NaOH, 13.3 ml) was added to a solution of 4-piperidone ethylene ketal (4.26 ml, 4.76 g, 33.3 mmol) and potassium ethylxanthate (2.35 g, 14.7 mmol) in water (100 ml) and stirred for 30 min. The mixture was extracted with ether, the ether extract was washed with HCl (1M), dried (sodium sulphate) and evaporated to give the product, MS (+EI) 231 (M+), 1H NMR (CDCl$_3$) 4.51 (2H, q), 4.19 (2H, dd), 3.99 (4H, s), 3.81 (2H, dd), 1.78 (2H, dd), 1.69 (2H, dd), 1.35 (3H, t).

EXAMPLE II 1-(2-Thienyl(iminomethyl))-4-piperidone ethylene ketal hydroiodide A solution of S-methyl-2-thiophenecarboximide hydroiodide (1.0 g, 3.5 mmol) (Fisons plc WO 95/05363) and 4-piperidone ethylene ketal (0.47 ml, 3.6 mmol) in acetonitrile (10 ml) was stirred for 20 h and evaporated. Flash chromatography on silica eluting with dichloromethanelmethanol (20:1) gave the product as a white solid, m.p. 217°–218° C.

EXAMPLE JJ

4-Oxopiperidine-1-carboxamide ethylene ketal

Trimethylsilyl isocyanate (0.6 g, 0.7 ml, 5.2 mmol) was added dropwise by syringe to a well stirred solution of 4-piperidone ethylene ketal (0.71 g, 5 mmol) in dry toluene (5 ml). The mixture was stirred at 20° C. for 24 h and then hexane (25 ml) was added. Stirrng was continued for 1 h during which time a white solid separated. The solid was collected by filtration, washed with hexane and dried to give the title compound (0.45 g), m.p. 201°–203° C.

EXAMPLE KK 1-(1-Pyrrolidinyl)carbonyl)-4-piperidone ethylene ketal (a) A solution of 1-(1H-imidazole-1-ylcarbonyl)-4-piperidone ethylene ketal (Example EE) (950 mg, 4 mmol)

and benzyl bromide (510 mg, 4 mmol) in dry acetonitrile (10 ml) was stirred at 20° C. for 18 h. The solvent was evaporated and the residue triturated with ether to give the crude quaternary salt as a hygroscopic solid (1.35 g, 82%). This was taken up in dichloromethane (20 ml), treated with a small excess of pyrrolidine (0.25 g, 3.5 mmol) and kept at room temperature overnight. The solution was washed successively with dilute HCl and water and dried over magnesium sulphate. Evaporation of solvent left the title compound as a colourless syrup (0.7 g) which slowly crystallised on standing to a waxy solid, m.p. 61°–64° C.

EXAMPLE LL

N-Ethyl-4-oxopiperidine-1-carboxamide ethylene ketal

Ethyl isocyanate (0.85 ml, 0.76 g, 10.7 mmol) was added dropwise with stirring to 4-piperidone ethylene ketal (1.43 g, 10 mmol) in dry dichloromethane (30 ml). The resulting pale yellow solution was stirred at 20° C. for 24 h, then evaporated to yield a yellow solid. Trituration with ether gave the title compound as a white crystalline solid (1.85 g), m.p. 120°–122° C.

EXAMPLE MM (3-Methyl-1,2,4-oxadiazol-5-yl)-4-piperidone ethylene ketal

3-Methyl-5-trichloromethyl-1,2,4-oxadiazole (Moussebois and Eloy, Helv. Chim. Acta 1964, 47, 838) (1 g, 5 mmol) and 4-piperidone ethylene ketal (1.5 g, 10 mmol) in ethanol (20 ml) were heated reflux overnight. The solvent was evaporated and the residue taken up in dichloromethane and filtered. The filtrate was washed with dilute HCl, dried over sodium sulphate and evaporated to leave a pale yellow oil (0.22 g). The acid washing was neutralised with solid sodium bicarbonate and extracted with dichloromethane. Evaporation gave further oil (0.17 g, total 0.39 g), MS (+EI) 225 (M+).

EXAMPLE NN (2-Thiazolyl)-4-piperidone ethylene ketal

4-Piperidone ethylene ketal (2.0 ml, 16 mmol), 2-bromothiazole (2.68 g) and caesium carbonate (8.9 g) in DMF (20 ml) were heated at 90°–100° C. for 16 h. The cooled mixture was diluted with water, extracted twice with ether, the ether layers washed with water six times, dried over sodium sulphate and evaporated. The residue was purified by flash chromatography on silica eluting with 50% ether/hexane to afford the title compound as a pale yellow oil (2.2 g), MS (+EI) 226 (M+), 1H NMR (CDCl$_3$) 7.17 (1H, d, 3.6 Hz), 6.55 (1H, d, 3.6 Hz), 4.00 (4H, s), 3.65–3.61 (4H, m), 1.83–1.80 (4H, m).

EXAMPLE OO 1-(4-Nitrophenyl)sulphonyl-4-piperidone ethylene ketal

A solution of 4-piperidone ethylene ketal (1.28 ml, 10 mmol) and triethylamine (1.4 ml, 10 mmol) in ethyl acetate (20 ml) was treated with a dropwise addition of 4-nitrophenylsulphonyl chloride (1.4 ml, 10 mmol) in ethyl acetate (20 ml) and stirred at room temperature for 2 h. The mixture was washed with water, dilute HCl, saturated sodium bicarbonate solution and brine, dried over sodium sulphate and evaporated to leave the title compound as a solid (2.8 g), MS (+EI) 328 (M+), 1H NMR (CDCl$_3$) 8.38 (2H, d, J 8.8 Hz), 7.96 (2H, d, J 8.8 Hz), 3.90 (4H, s), 3.22 (4H, t, J 5.7 Hz), 1.80 (4H, t, J 5.7 Hz).

EXAMPLE PP

The following compounds were prepared by the method of Example OO:

(a) 1-(4-Methoxyphenyl)sulphonyl-4-piperidone ethylene ketal, off-white solid, MS (+EI) 313 (M+), 1H NMR (CDCl$_3$) 7.70 (2H, d, J 8.8 Hz), 6.99 (2H, d, J 8.8 Hz), 3.90 (4H, s), 3.87 (3H, s), 3.13 (4H, t, J 5.6 Hz), 1.78 (4H, t, J 3.6 Hz).

(b) 1-Methanesulphonyl-4-piperidone ethylene ketal, pale yellow waxy solid.

EXAMPLE QQ 1-((4-Cyanophenyl)thioxomethyl)-4-piperidone ethylene ketal

A solution of 1-(4-cyanobenzoyl)-4-piperidone ethylene ketal (1.00 g, 3.68 mmol) and Lawesson's reagent (1.2 g, 2.9 mmol) in dioxane (20 ml) was heated to reflux for 1 h, cooled and evaporated. The residue was pre-absorbed on silica gel and purified by flash chromatography eluting with 25% ethyl acetate/hexane, increasing the gradient to 40% ethyl acetate/hexane, to afford the product as a yellow solid (353 mg), MS (+EI) 288 (M+), 1H NMR(CDCl$_3$) 7.67 (2H, d, J 7 Hz), 7.36 (2H, d, J 7 Hz), 4.5–4.45 (2H, m), 4.06–3.98 (4H, m), 3.58 (2H, dd, J 6, 4.2 Hz), 1.94 (2H, t, J 6 Hz), 1.69 (2H, t, J 6 Hz).

EXAMPLE RR 1-(6-Cyano-3-pyridyl)carbonyl-4-piperidone ethylene ketal

A stirred suspension of copper (I) cyanide (0.66 g, 7.4 mmol) and 1-(6-bromo-3-pyridyl)carbonyl-4-piperidone ethylene ketal (2.2 g, 6.7 mmol, prepared as in Example V from 6-bromo-3-pyridinecarboxylic acid) in DMF (30 ml) was heated at 150° C. for 3 h. The mixture was cooled, diluted with water, extracted with ethyl acetate, dried over sodium sulphate and evaporated. Purification by flash chromatography on silica, eluting with 20% ethyl acetate/hexane, gave a white crystalline solid (0.96 g, 52%), m.p. 133°–135° C.

EXAMPLE SS 1-(5-Thiazolylcarbonyl)-4-piperidone ethylene ketal (a) 5-Thiazolecarboxylic acid 2-(Trimethylsilyl)thiazole (2 g, 12.7 mmol) in ether (10 ml) was added dropwise to a solution of n-butyllithium (1.43M in hexane, 9.33 ml) in ether (20 ml) over 20 min. at −78° C., stirred for 1 h and quenched with solid carbon dioxide. The mixture was allowed to warm to room temperature over 16 h, diluted with 10% sodium hydroxide and extracted twice with ethyl acetate. The aqueous layer was acidified with ice-cold dilute HCl, extracted with ethyl acetate, the organic extract washed with brine, dried over sodium sulphate and evaporated to give a pale yellow solid (870 mg), 1H NMR (d$_6$-DMSO) 13.58 (1H, br. s), 9.33 (1H, s), 8.45 (1H, s).

(b) 1-(5-Thiazolylcarbonyl)-4-piperidone ethylene ketal

This was prepared by the method of Example V to give a yellow oil, MS (+CI) 255 ([M+H]+).

Preparation of products

EXAMPLE 1

1,2-Dihydro-2-phenyl-4-quinazolinamine hydrochloride

A solution of 2-aminobenzamidine dihydrochloride (Example A) (1.0 g, 4.8 mmol) and benzaldehyde (0.48 ml, 5.8 mmol) in ethanol (30 ml) was heated at reflux for 2 hours. The solution was cooled and the solvent evaporated to give an oil which was purified by flash chromatography on aluminium oxide (Brockman 1, activated neutral) using dichloromethane/methanol as eluant to give a solid which was recrystallised from isopropyl alcohol to afford the title compound as a solid (0.65 g), m.p. 212°–214° C.

The compounds of Examples 2–26 were prepared from 2-aminobenzamidine dihydrochloride and an appropriate aldehyde or ketone by the method of Example 1:

EXAMPLE 2

1,2-Dihydro-4-quinazolinamine hydrochloride

Prepared using aqueous formaldehyde; amorphous solid. MS (+FAB) 148 ([M+H]+), 1H NMR ($d_6$-DMSO) 9.70 (1H, s), 9.09 (1H, s), 8.88 (1H, s), 7.83 (1H, d), 7.46 (1H, dd), 7.40 (1H, s), 6.90 (1H, d), 6.84 (1H, dd), 4.55 (1H, s).

EXAMPLE 3

1,2-Dihydro-2-methyl-4-quinazolinamine hydrochloride

Prepared using acetaldehyde; m.p. 210°–212° C.

EXAMPLE 4

2-Ethyl-1,2-dihydro-4-quinazolinamine hydrochloride

Prepared using propionaldehyde; m.p. 139°–141° C.

EXAMPLE 5

2-Cyclopropyl-1,2-dihydro-4-quinazolinamine hydrochloride

Prepared using cyclopropanecarboxaldehyde; m.p. 192°–193° C.

EXAMPLE 6

2-Cyclobutyl-1,2-dihydro-4-quinazolinamine hydrochloride

Prepared using cyclobutanecarboxaldehyde; m.p. 200°–202° C.

EXAMPLE 7

2-Cyclopentyl-1,2-dihydro-4-quinazolinamine hydrochloride

Prepared using cyclopentanecarboxaldehyde; m.p. 242°–244° C. (dec.).

EXAMPLE 8

1,2-Dihydro-2,2-dimethyl-4-quinazolinamine hydrochloride

Prepared using acetone; m.p. 251°–253° C.

EXAMPLE 9

2-Ethyl-1,2-dihydro-2-methyl-4-quinazolinamine hydrochloride

Prepared using 2-butanone; m.p. 113°–115° C.

EXAMPLE 10

1.2-Dihydro-2-methyl-2-phenyl-4-quinazolinamine hydrochloride

Prepared using acetophenone;.m.p. 155°–157° C.

EXAMPLE 11

2-(2-Furyl)-1,2-dihydro-4-quinazolinamine hydrochloride

Prepared using 2-furancarboxaldehyde; m.p. 239°–240° C.

EXAMPLE 12

1,2-Dihydro-2-(2-thienyl)-4-quinazolinamine hydrochloride

Prepared using 2-thiophenecarboxaldehyde; m.p. 243°–245° C.

EXAMPLE 13

1,2-Dihydro-2-(4-pyridyl)-4-quinazolinamine hydrochloride

Prepared using 4pyridinecarboxaldehyde; m.p. 193°–195° C.

EXAMPLE 14

1,2-Dihydro-2-(1H-imidazol-2-yl)-4-quinazolinamine dihydrochloride

Prepared using 1H-imidazole-2-carboxaldehyde; m.p. 168°–170° C.

EXAMPLE 15

1,2-Dihydro-2-(2-thiazolyl)-4-quinazolinamine dihydrochloride

Prepared using 2-thiazolecarboxaldehyde; amorphous solid, MS (+FAB) 231 ([M+H]+), 1H NMR ($d_6$-DMSO) 10.45 (1H, s), 9.08 (1H, s), 8.45 (1H, s), 7.87 (1H, d), 7.80 (1H, d), 7.74 (1H, d), 7.49 (1H, t), 6.96 (1H, d), 6.84 (1H, t), 6.39 (1H, s).

EXAMPLE 16

2-(4-Cyanophenyl)-1,2-dihydro-4-quinazolinamine hydrochloride

Prepared using 4-cyanobenzaldehyde; m.p. 201°–203° C.

EXAMPLE 17

2-(4-Dimethylaminophenyl)-1,2-dihydro-4-quinazolinamine hydrochloride

Prepared using 4-(dimethylamino)benzaldehyde; m.p. 213°–215° C.

EXAMPLE 18

1,2-Dihydro-2-(4-nitrophenyl)-4-quinazolinamine hydrochloride

Prepared using 4-nitrobenzaldehyde; m.p. 223°–225° C.

EXAMPLE 19

2-(9-Anthracenyl)-1,2-dihydro-4-quinazolinamine hydrochloride

Prepared using anthracene-9-carboxaldehyde; m.p. >250° C., MS (+FAB) 324 ([M+H]+).

EXAMPLE 20

2-(4-Amino-1,2-dihydroguinazolin-2-yl) benzenemethanol hydrochloride

Prepared from 1,3-dihydroisobenzofuran-1-ol; m.p. 120° C. (dec.)

EXAMPLE 21

1,2-Dihydro-2-(2-nitrophenyl)-4-quinazolinamine hydrochloride

Prepared using 2-nitrobenzaldehyde; MS (+FAB) 269 ([M+H]+), 1H NMR ($d_6$-DMSO) 10.00 (1H, s), 9.47 (1H, s), 8.95 (1H, s), 8.14 (1H, dd), 7.91 (1H, dd), 7.88 (1H, s), 7.79–7.84 (3H, m), 7.71 (1H, t), 7.48 (1H, t), 6.96 (1H, d), 6.86 (1H, d), 6.55 (1H, s).

EXAMPLE 22

1,2-Dihydro-2-(5-nitro-2-thienyl)4-quinazolinamine hydrochloride

Prepared using 5-nitro-2-thiophenecarboxaldehyde; m.p. 215°–217° C.

EXAMPLE 23

Ethyl 2-(4-amino-1,2-dihydroquinazolin-2-yl)- 1H-pyrrole-1-carboxylate hydrochloride Prepared using ethyl 2-formylpyrrole-1-carboxylate (Example P); MS (+FAB) 285 ([M+H]+), 1H NMR ($d_6$-DMSO) 9.85 (1H, s), 9.31 (1H, s), 8.92 (1H, s), 7.88 (1H, d), 7.74 (1H, s), 7.48 (1H, t), 7.38 (1H, t), 7.00 (1H, d), 6.83 (1H, t), 6.45 (1H, s), 6.19 (2H, d), 4.44 (2H, q), 1.38 (3H, t).

EXAMPLE 24

1,2-Dihydro-2-(trimethylsilylethyny)-4-quinazolinamine hydrochloride

Prepared using 3-(trimethylsilyl)propynal; MS (+FAB) 244 [(M+H)+], 1H NMR ($d_6$-DMSO) 7.7 (1H, d), 7.5 (1H, br. s), 7.35 (1H, dd), 6.82–6.7 (2H, dt), 5.64 (1H, s), 0.00 (9H, s).

EXAMPLE 25

Spiro [cyclopentane- 1,2'(1'H)-quinazoline]-4'-amine hydrochloride

Prepared using cyclopentanone; m.p. 208.5°–210° C.

EXAMPLE 26

Spiro[cyclohexane-1,2'(1'H)quinazoline]-4'-amine hydrochloride

Prepared using cyclohexanone; m.p. 256°–258° C.

The compounds of Example 27 and 28 were prepared from 2-amino-6-chlorobenzamidine dihydrochloride (Example B) and appropriate aldehydes. using the method of Example 1

EXAMPLE 27

5-Chloro-2-(2-furyl)-1,2-dihydro-4-quinazolinamine hydrochloride

Prepared using 2-furancarboxaldehyde; yellow crystals, m.p. 235°–237° C.

EXAMPLE 28

5-Chloro-1.2-dihydro-2-(2-thienyl)-4-quinazolinamine hydrochloride

Prepared using 2-thiophenecarboxaldehyde; yellow crystals, MS (+FAB) 264/266 ([M+H]+), 1H NMR ($d_6$-DMSO) 8.60 (1H, s), 7.59 (1H, d), 7.46 (1H, t), 7.20 (1H, d), 7.06 (1H, dd), 6.98 (1H, s), 6.97 (1H, s), 6.22 (1H, s).

The compounds of Examples 29–44 were prepared from 2-amino-6-fluorobenzamidine dihydrochloride (Example C) and appropriate aldehydes or ketones using the method of Example 1.

EXAMPLE 29

5-Fluoro-1,2-dihydro-2-phenyl-4-quinazolinamnine hydrochloride

Prepared using benzaldehyde; m.p. 253°–255° C.

EXAMPLE 30

5-Fluoro-2-(2-furyl)-1,2-dihydro-4-guinazolinamine hydrochloride

Prepared using 2-firancarboxaldehyde; yellow crystals, m.p. 228°–229° C.

EXAMPLE 31

5-Fluoro-1,2-dihydro-2-(2-hydroxyphenyl)-4-quinazolinamine hydrochloride

Prepared using salicylaldehyde; m.p. 240° C.

EXAMPLE 32

5-Fluoro-1,2-dihydro-2-(3-hydroxyhenyl)-4-quinazolinamine hydrochloride

Prepared using 3-hydroxybenzaldehyde; m.p. 235°–237° C. (decomp.)

EXAMPLE 33

5-Fluoro-1,2-dihydro-2-(4-hydroxyphenyl)-4-quinazolinamine hydrochloride

Prepared using 4-hydroxybenzaldehyde; m.p. 270°–272° C.

EXAMPLE 34

Ethyl 3-(4-Amino-5-fluoro-1,2-dihydroquinazolin-2-yl)-1H-pyrrole-1-carboxylate hydrochloride Prepared using ethyl 3-formylpyrrole-1-carboxylate (Example Q); m.p. 165°–167° C.

EXAMPLE 35

5-Fluoro-1,2dihydro-2-(2-thienyl)-4-quinazolinamine hydrochloride

Prepared using 2-thiophenecarboxaldehyde; m.p. 204°–205° C.

EXAMPLE 36

5-Fluoro-1,2-dihydro-2-(2-thiazolyl)-4-quinazolinamine hydrochloride

Prepared using 2-thiazolecarboxaldehyde; m.p. 191°–192° C.

EXAMPLE 37

5-Fluoro-2-(4-fluorophenyl)-1.2-dihydro-4-quinazolinamine hydrochloride

Prepared using 4fluorobenzaldehyde; m.p. 191°–193° C.

EXAMPLE 38

5-Fluoro-1,2-dihydro-2-(4-methoxyphenyl)-4-quinazolinamine hydrochloride

Prepared using 4-methoxybenzaldehyde; m.p. 185°–187° C.

EXAMPLE 39

5-Fluoro-1,2-dihydro-2-(4-(methylthio)phenyl)-4-quinazolinamine hydrochloride

Prepared using 4-(methylthio)benzaldehyde; m.p. 157°–159° C.

EXAMPLE 40

5-Fluoro-1,2-dihydro-2-(2-(trifluoromethyl)phenyl)-4-quinazolinamine hydrochloride Prepared using 2-(trifluoromethyl)benzaldehyde; m.p. 241°–243° C.

EXAMPLE 41

5-Fluoro-1,2-dihydro-2-(4-(trifluoromethyl)phenyl)-4-quinazolinamine hdrochloride Prepared using 4-(trifluoromethyl)benzaldehyde; m.p. 220°–222° C.

EXAMPLE 42

5-Fluoro-1,2-dihydro-2-(1-methylethyl)-4-quinazolinamine hydrochloride

Prepared using isobutyraldehyde; m.p. 159°–161° C.

EXAMPLE 43

2-Cyclobutyl-5-fluoro-1,2-dihydro-4-quinazolinamine hydrochloride

Prepared using cyclobutanecarboxaldehyde; m.p. 209°–210° C.

EXAMPLE 44

5-Fluoro-(2-furyl)-1,2-dihydro-2-methyl-4-quinazolinamine hydrochloride

Prepared using 2-acetylfuran; m.p. 224°–226° C. (decomp).

EXAMPLE 45

2-(2-Furyl)-5-(methylthio)-1,2-dihydro-4-quinazolinamine hydrochloride

This was prepared from 2-amino-6-(methylthio)benzamidine dihydrochloride (Example F) and 2-furancarboxaldehyde using the method of Example 1 to give yellow crystals, m.p. 207°–208° C.

The compounds of Example 46 and 47 were prepared from 2-(methylamino) benzamidine dihydrochloride (Example I) and appropriate aldehydes using the method of Example 1.

EXAMPLE 46

1,2-Dihydro-1-methyl-2-phenyl-4-quinazolinamine hydrochloride

Prepared using benzaldehyde; m.p. >250° C., MS (+ESI) 238 ([M+H]+).

EXAMPLE 47

2-Cyclopropyl-1,2-dihydro-1-methyl-4-quinazolinamine hydrochloride

Prepared using cyclopropanecarboxaldehyde; m.p. >250° C., MS (+ESI) 202 ([M+H]+).

The compounds of Examples 48–98 were prepared from 2-aminobenzamidine dihydrochloride (Example A) and an acetal or ketal by the method of Example 1.

EXAMPLE 48

4-Amino-1,2-dihydro-2-quinazolinepropanamine hydrochloride

Prepared using 4-aminobutyraldehyde diethyl acetal; MS (+EI) 206 ([MN+H]+), 1H NMR ($d_6$-DMSO) 10.08 (1H, s), 9.19 (1H, s), 8.77 (1H, s), 8.06 (2H, s), 7.85 (1H, d), 7.45 (1H, t), 6.90 (1H, d), 6.79 (1H, t), 4.92 (1H, s), 2.80 (2H, d), 1.75 (4H,m).

EXAMPLE 49

4-Amino-1,2-dihydro-2-quinazolineethanamine hydrochloride

Prepared using 3-aminopropionaldehyde diethyl acetal; MS (+FAB) 191 ([M+H]+), 1H NMR ($d_6$-DMSO) 10.21 (1H, s), 9.27 (1H, s), 8.82 (1H, s), 8.18 (3H, s), 7.87 (1H, d), 7.76 (1H, s), 7.47 (1H, t), 6.93 (1H, d), 6.82 (1H, t), 5.05 (1H, t), 2.97 (2H, s), 2.04–2.08 (2H, m).

EXAMPLE 50

2-(2-(2-Azidoethyl)phenyl)-1,2-dihydro-4-quinazolinamine hydrochloride

Prepared using the intermediate of Example L; MS (+FAB) 291 ([M+H]+), 1H NMR ($d_6$-DMSO) 7.90 (1H, d), 7.66 (2H, m), 7.37–7.53 (4H, m), 6.83–6.91 (2H, m), 6.18 (1H, s), 3.58–3.63 (2H, m), 3.04–3.07 (2H, m).

EXAMPLE 51

Ethyl N-(4-Amino-1,2-dihydroquinazolin-2-ylpropyl)carbamate hydrochloride

Prepared using the intermediate of Example M; MS (+FAB) 277 ([M+H]+), 1H NMR ($d_6$-DMSO) 9.79 (1H, s), 9.08 (1H, s), 8.55 (1H, s), 7.81 (1H, d), 7.47 (1H, s), 7.43 (1H, t), 7.16 (1H, t), 6.87 (1H, d), 6.79 (1H, t), 4.83 (1H, t), 3.97 (2H, q), 2.98 (2H, dt), 1.66–1.71 (2H, m), 1.48–1.59 (2H, m), 1.14 (3H, t).

EXAMPLE 52

Ethyl N-(4-Amino-1,2-dihydroquinazolin-2-ylethyl) carbamate hydrochloride

Prepared using the intermediate of Example N; MS (+FAB) 263 ([M+H]+), 1H NMR ($d_6$-DMSO) 9.83 (1H, s), 9.13 (1H, s), 8.64 (1H, s), 7.83 (1H, d), 7.51 (1H, s), 7.46 (1H, t), 7.23 (1H, t), 6.89 (1H, d), 6.81 (1H, t), 4.87 (1H, t), 3.97 (2H, q), 3.13 (2H, dt), 1.84 (2H, dt), 1.14 (3H, t).

EXAMPLE 53

Ethyl N-(4-Amino-1,2-dihydroquinazolin-2-ylmethyl)carbamate.

Prepared using the intermediate of Example O. It was purified by reverse phase HPLC chromatography and obtained as the trifluoroacetate salt: MS (+FAB) 249 ([M+H]+), 1H NMR (d$_6$-DMSO) 9.50 (1H, s), 9.00 (1H, s), 8.58 (1H, s), 7.78 (1H, d), 7.54 (1H, s), 7.45 (1H, t), 7.34 (1H, t), 6.77–6.84 (2H, m), 4.83 (1H, s), 3.98 (2H, q), 3.05–3.25 2H,m), 1.15 (3H, t).

EXAMPLE 54

1-(2-Thiazolylcarbonyl)spiro[piperidine-4,2'(1'H)-quinazoline]-4'-amine hydrochloride.

Prepared using the intermediate of Example W(jj); m.p. 217°–219° C.

EXAMPLE 55

1-(4-Methoxybenzoyl)spiro[piperidine-4,2'( 1'H)-quinazoline]-4'-amine hydrochloride Prepared using the intermediate of Example U(a); bright yellow crystals, m.p. >250° C.; M+(+EI) 349 (M+).

EXAMPLE 56

1-(4-Cyanobenzoyl)spiro[piperidine-4,2'(1'H)-quinazoline]-4'-amine hydrochloride Prepared using the intermediate of Example U(b); bright yellow crystals, m.p. >250° C.; MS (+EI) 345 (M+).

EXAMPLE 57

1-(4-Nitrobenzoyl)spiro[piperidine-4,2'(1'H)-quinazoline]-4'-amine hydrochloride Prepared using the intermediate of Example U(c); bright yellow crystals, mp. >250° C.; MS (+EI) 365 (M+).

EXAMPLE 58

1-(2-Furylcarbonyl)spiro[piperidine-4,2'(1'H)-quinazoline]-4'-amine hydrochloride Perpared using the intermediate of Example U(d); bright yellow crystals, m.p. >250° C.; MS (+EI) 311 (M+).

EXAMPLE 59

1-(4-Ethylbenzoyl)spiro[piperidine-4,2'(1'H)-quinazoline]-4'-amine hydrochloride Perpared using the intermediate of Example U(e); bright yellow crystals, m.p. >250° C.; MS (+EI) 348 (M+).

EXAMPLE 60

1-(4-Chlorobenzoyl)spiro[piperidine-4,2'(1'H)-quinazoline]-4'-amine hydrochloride Perpared using the intermediate of Example U(f); bright yellow crystals, m.p. >250° C.; MS (+EI) 354/356 (M+).

EXAMPLE 61

1-(2-Nitrobenzoyl)spiro[piperidine-4,2'(1'H)-quinazoline]-4'-amine hydrochloride Perpared using the intermediate of Example U(g); bright yellow crystals, m.p. >250° C.; MS (+EI) 365 (M+).

EXAMPLE 62

1-(3-Nitrobenzoyl)spiro[piperidine-4,2'(1'H)-quinazoline]-4'-amine hydrochloride Prepared using the intermediate of Example U(h); bright yellow crystals, m.p. >250° C.; MS (+EI) 366 (M+).

EXAMPLE 63

1-(2-Methylbenzoyl)spiro[piperidine-4,2'(1'H)-quinazoline]-4'-amine hydrochloride Perpared using the intermediate of Example U(i); bright yellow crystals, m.p. 206°–207° C.

EXAMPLE 64

1-(3-Methylbenzoyl)spiro[piperidine-4,2'(1'H)-quinazoline]-4'-amine hydrochloride Perpared using the intermediate of Example U(j) bright yellow crystals, m.p. >250° C.; MS (+EI) 334 (M+).

EXAMPLE 65

1-(2-Thienylcarbonyl)spiro[piperidine-4,2'(1'H)-quinazoline]-4'-amine hydrochloride Perpared using the intermediate of Example U(k); bright yellow crystals, m.p. 253°–255° C.

EXAMPLE 66

1-((4-Hydroxy)benzoyl)spiro[piperidine-4,2'(1'H)-quinazoline]-4'-amine hydrochloride Perpared using the intermediate of Example U(l); bright yellow crystals, m.p. >250° C.; MS (+EI) 336 (M+) (cleavage of the acetoxy group occurs spontaneously during reaction).

EXAMPLE 67

1-(3-Hydroxybenzoyl)spiro[piperidine-4,2'(1'H)-quinazoline]4'-amine hydrochloride Perpared using the intermediate of Example U(m); yellow foam, MS (+FAB) 337 ([M+H]+), 1H NMR (d$_6$-DMSO) 10.51 (1H, s), 9.80 (1H, br. s), 9.26 (1H, s), 8.67 (1H, s), 7.85 (1H, d, J 8.0 Hz), 7.72 (1H, s), 7.48 (1H, t, J 7.7 Hz), 7.25 (1H, t, J 7.7 Hz), 6.93 (1H, d, J 8.3 Hz), 6.81 (4H, m), 3.68 (2H, br. s), 3.53 (2H, br. s), 1.97 (4H, br. s).

EXAMPLE 68

1-(4-(Phenylmethoxy)benzoyl)spiro[piperidine-4,2' (1'H)-quinazoline]-4'-amine hydrochloride Perpared using the intermediate of Example W(p); yellow foam, MS (+FAB) 427 ([M+H]+), 1H NMR (d$_6$-DMSO) 7.75 (1H, d, J 7.9 Hz), 7.47–7.32 (9H, m), 7.07 (2H, d, J 8.7 Hz), 6.87 (1H, d, J 8.2 Hz), 6.77 (1H, t, J 7.4 Hz), 5.15 (2H, s), 4.35–3.5 (4H, br. s), 1.97–1.65 (2H, br. s).

EXAMPLE 69

1-(4-(4,4-Dimethyloxazolin-2-yl)benzoyl)spiro [piperidine-4,2'(1'H)-quinazoline]-4'-amine hydrochloride Perpared using the intermediate of Example W(q); yellow crystals, m.p. 224° C. (dec.).

EXAMPLE 70

1-(2-Pyridylcarbonyl)spiro[piperidine-4,2'(1'H)-quinazoline]-4'-amine hydrochloride Perpared using the intermediate of Example W(r); yellow glass, MS (+EI) 321 (M+), 1H NMR ($d_6$-DMSO) 10.36 (1H, br. s), 8.59 (1H, d, J 4.2 Hz), 7.95 (1H, t, J 7.7 Hz), 7.84 (1H, d, J 8.0 Hz), 7.70 (1H, s), 7.39 (1H, d, J 7.7 Hz), 7.49 (2H, m), 6.93 (1H, d, J 8.3 Hz), 6.82 (1H, t, J 7.6 Hz), 3.89 (1H, br. s), 3.77 (1H, br. s), 3.58 (2H, br. s), 2.01 (2H, br. s), 1.90 (2H, br. s).

EXAMPLE 71

1-(4-Pyridylcarbonyl)spiro[piperidine-4,2'(1'H)-quinazoline]-4'-amine hydrochloride Perpared using the intermediate of Example W(s); yellow glass, MS (+EI) 321 (M+), 1H NMR ($d_6$-DMSO) 8.69 (2H, d, J 5.7 Hz), 7.84 (1H, d, J 7.8 Hz), 7.71 (1H, s), 7.48 (1H, t, J 7.3 Hz), 7.39 (2H, d, J 5.9 Hz), 6.94 (1H, d, J 8.2 Hz), 6.82 (1H, d, J 7.5 Hz), 3.88 (2H, br. s), 3.78 (2H, br. s), 2.03 (1H, br. s), 1.92 (2H, br. s), 1.82 (1H, br. s).

EXAMPLE 72

1-(3-Pyridazinylcarbonyl)spiro[piperidine-4,2'(1'H)-quinazoline]-4'-amine hydrochloride Perpared using the intermediate of Example W(t); yellow glass, MS (+FAB) 323 ([M+H]+), 1H NMR ($d_6$-DMSO) 10.48 (1H, br. s), 9.37 (1H, d, J 5.2 Hz), 9.29 (1H, s), 7.83 (1H, d, J 8.0 Hz), 7.75–7.71 (2H, m), 7.47 (1H, t, J 15.4 Hz), 6.94 (1H, d, J 8.3 Hz), 6.81 (1H, t, J 7.5 Hz), 3.97–3.88 (2H, m), 3.86–3.75 (2H, m), 3.48 (2H, br. s), 2.1–1.8 (4H, m).

EXAMPLE 73

1-(3,5-Dimethylbenzoyl)spiro[piperidine-4,2'(1'H)-quinazoline]-4'-amine hydrochloride Perpared using the intermediate of Example W(u); yellow crystals, m.p. 195°–197° C. (dec.).

EXAMPLE 74

1-(3-Fluoro-4-methylbenzoyly)spiro[piperidine-4,2'(1'H)-quinazoline]-4'-amine hydrochloride Perpared using the intermediate of Example W(v); yellow crystals, m.p. 271°–273° C. (dec.).

EXAMPLE 75

1-(3,5-Difluorobenzoyl)spiro[piperidine-4,2'(1'H)-quinazoline]-4'-amine hydrochloride Perpared using the intermediate of Example W(w); yellow crystals, m.p. 259°–261° C. (dec.).

EXAMPLE 76

1-(4-(1,2,3-Thiadiazol-4-yl)benzoyl)spiro[piperidine-4,2'(1'H)-quinazoline]-4'-amine hydrochloride Perpared using the intermediate of Example W(a); yellow crystals, m.p. 220° C. (dec.).

EXAMPLE 77

1-(4-Bromobenzoyl)spiro[piperidine-4,2'(1'H)-quinazoline]-4'-amine hydrochloride Perpared using the intermediate of Example W(b); yellow crystals, m.p. 194°–196° C.

EXAMPLE 78

1-(4-Iodobenzoyl)spiro[piperidine-4,2'(1'H)-quinazoline]-4'-amine hydrochloride

Perpared using the intermediate of Example W(c); yellow crystals, m.p. >250° C., MS (+EI) 446 (M+).

EXAMPLE 79

1-(4-(Trifluoromethyl)benzoyl)spiro[piperidine-4,2'(1'H)-quinazoline]-4'-amine hydrochloride Perpared using the intermediate of Example W(d); yellow crystals, m.p. >250° C., MS (+EI) 388 (M+).

EXAMPLE 80

1-(4-(Methanesulphonyl)benzoyl)spiro[piperidine-4,2'(1'H)-quinazoline]-4'-amine hydrochloride Perpared using the intermediate of Example W(e); yellow crystals, m.p. >250° C., MS (+EI) 398 (M+).

EXAMPLE 81

1-(4-Fluorobenzoyl)spiro[piperidine-4,2'(1'H)-quinazoline]-4'-amine hydrochloride Perpared using the intermediate of Example W(f); yellow crystals, m.p. >250° C., MS (+EI) 338 (M+).

EXAMPLE 82

1-(5-Bromo-2-furylcarbonyl)spiro[piperidine-4,2'(1'H)-quinazoline]-4'-amine hydrochloride Perpared using the intermediate of Example V; yellow crystals, m.p. 251°–253° C.

EXAMPLE 83

1-([1,1'-Biphenyl]-4-ylcarbonyl)spiro[piperidine-4,2'(1'H)-quinazoline]-4'-amine hydrochloride Perpared using the intermediate of Example W(g); yellow crystals, m.p. >250° C., MS (+EI) 323 (M+).

EXAMPLE 84

1-(5-Chloro-2-thienylcarbonyl)spiro[piperidine-4,2'(1'H)-quinazoline]-4'-amine hydrochloride Perpared using the intermediate of Example W(j); yellow crystals, m.p. 243°–245° C.

EXAMPLE 85

1-(3-Pyridylcarbonyl)spiro[piperidine-4,2'(1'H)-quinazoline]-4'-amine hydrochloride Perpared using the intermediate of Example W(i); yellow crystals, m.p. >250° C., MS (+EI) 321 (M+).

EXAMPLE 86

1-(4-(Aminosulphonyl)benzoyl)spiro[piperidine-4,2'(1'H)-quinazoline]-4-amine hydrochloride Perpared using the intermediate of Example W(h); yellow crystals, m.p. >250° C., MS (+EI) 326 (M+).

EXAMPLE 87

1-(4-Methylbenzoyl)spiro[piperidine-4,2'(1'H)-quinazoline]-4'-amine hydrochloride Perpared using the intermediate of Example T; yellow crystals, m.p. >250° C., MS (+EI) 334 (M+).

EXAMPLE 88

1-(3-Amino-4-chlorobenzoyl)spiro[piperidine-4,2'(1'H)-quinazoline]-4'-amine

Perpared using the intermediate of Example W(k) and purified by conversion to the maleate salt; yellow crystals m.p. ca. 125° C.

EXAMPLE 89

1-((2-(Trifluoromethyl)phenyl)acetyl)spiro[piperidine-4,2'(1'H)-quinazoline]-4'-amine hydrochloride Perpared using the intermediate of Example W(kk); yellow solid, MS (+EI) 402 (M+); 1H NMR ($d_6$-DMSO) 10.51 (1H, br. s), 8.78 (2H, br. s), 7.85 (1H, d, J 8.1 Hz), 7.70 (1H, s), 7.69 (1H, d, J 8.2 Hz), 7.62 (1H, t, J 7.5 Hz), 7.48 (2H, m), 7.38 (1H, d, J 7.6 Hz), 6.94 (1H, d, J 8.3 Hz), 6.82 (1H, t, J 7.6 Hz), 3.93 (2H, s), 3.77 (3H, m), 3.56 (1H, m), 1.98 (1H, m), 1.82 (2H, m), 1.74 (1H, m).

EXAMPLE 90

Methyl 4-(4'-aminospiro[piperidine-4,2'(1'H)-quinazoline]-1-ylcarbonyl)benzoate hydrochloride Perpared using the intermediate of Example W(l) and was obtained as a mixture with up to 25% of the corresponding ethyl ester as a yellow glass, MS (+FAB) 393 ([M+H]+, ethyl ester), 379 ([M+H]+, methyl ester); 1H NMR ($d_6$-DMSO) 7.95 (2H, d, J 7.9 Hz), 7.73 (1H, d, J 7.9 Hz), 7.56 (1H, br. s), 7.44 (2H, d, J 7.8 Hz), 7.38 (1H, t, J 7.8 Hz), 6.83 (1H, d, J 8.3 Hz), 6.72 (1H, t, J 7.6 Hz), 3.78 (3H, s), 3.60 (2H, br. s), 3.34 (2H, br. s), 1.93 (1H, br. s), 1.83 (2H, br. s), 1.71 (1H, br. s). Also peaks for ethyl ester: 4.26 (2H, q, J 7.0 Hz), 1,23 (3H, t, J 7.0 Hz).

EXAMPLE 91

1-(4-(1H-Pyrrol-1-yl)benzoyl)spiro[piperidine-4,2'(1'H)-quinazoline]-4'-amine hydrochloride Perpared using the intermediate of Example W(m); yellow foam, MS (+FAB) 386 ([M+H]+); 1H NMR ($d_6$-DMSO) 10.28 (1H, br. s), 7.76 (1H, d, J 8.0 Hz), 7.60 (3H, d, J 8.4 Hz), 7.41 (2H, d, J 8.5 Hz), 7.37 (3H, t, J 2.1 Hz), 6.86 (1H, d, J 8.3 Hz), 6.74 (1H, t, J 7.6 Hz), 6.22 (2H, t, J 2.0 Hz), 3.52 (4H, br. s), 1.90 (2H, br. s), 1.79 (2H, br. s).

EXAMPLE 92

4'-Aminospiro[piperidine-4,2'(1'H)-quinazoline]-1-carboxamide hydrochloride

Perpared using the intermediate of Example JJ; yellow solid, m.p. 245°–248° C. (dec.).

EXAMPLE 93

1-(3-Methyl-1,2,4-oxadiazol-5-yl)spiro[piperidine-4,2'(1'H)-quinazoline]-4'-amine hydrochloride Perpared using the intermediate of Example MM; hygroscopic yellow powder, MS (+EI) 298 (M+); 1H NMR ($d_6$-DMSO) 10.59 (1H, br. s), 9.31 (1H, br. s), 8.68 (1H, br. s), 7.87 (1H, d), 7.77 (1H, s), 7.49 (1H, t), 6.95 (1H, d), 6.83 (1H, t), 3.82–3.70 (4H, m), 2.13 (3H, s), 2.08 (2H, m), 1.93 (2H, m).

EXAMPLE 94

1-(2-Thiazolyl)spiro[piperidine-4,2'(1'H)-quinazoline]-4'-amine hydrochloride

Perpared using the intermediate of Example NN; yellow crystals, m.p. 256°–257° C.

EXAMPLE 95

1-(4-Nitrophenylsulphonyl)spiro[piperidine-4,2'(1'H)-quinazoline]-4'-amine hydrochloride Perpared using the intermediate of Example OO; yellow crystals, m.p. >250° C., MS (+FAB) 402 ([M+H]+).

EXAMPLE 96

1-(4-Methoxyphenylsulphonyl)spiro[piperidine-4,2'(1'H)-quinazoline]-4'-amine hydrochloride Perpared using the intermediate of Example PP(a); yellow crystals, m.p. >250° C., MS (+FAB) 387 ([M+H]+).

EXAMPLE 97

1-(Methanesulphonyl)spiro[piperidine-4,2'(1'H)-quinazoline]-4'-amine hydrochloride Perpared using the intermediate of Example PP(b); yellow crystals, m.p. 267°–269° C. (dec.).

EXAMPLE 98

1-(1-Oxobutyl)spiro[piperidine-4,2'(1'H)-quinazoline]-4'-amine

Perpared using the intermediate of Example S, and was purified by conversion to the maleate salt, m.p. 163°–164° C. (from ethanol and ether).

EXAMPLE 99

5'-Chloro-1-(4H)-cyanobenzoyl)spiro[piperidine-4,2'(1'-quinazoline]-4'-amine hydrochloride.

This was prepared with 2-amino-6-chlorobenzamidine dihydrochloride (Example B) and 1-(4-cyanobenzoyl)4-piperidone ethylene ketal (Example U(b)) by the method of Example 1 to give the tide compound as pale yellow crystals, m.p. 289°–291° C.

The compounds of Examples 100 and 101 were prepared by the method of Example 99

EXAMPLE 100

5'-Chloro-1-(2-thienylcarbonyl)spiro[pieridine-4,2'(1'H)-quinazoline]-4'-amine hydrochloride From the intermediate of Example U(k); yellow crystals, m.p. 247°–249° C.

EXAMPLE 101

5'-Chloro-1-(2-furylcarbonyl)spiro[piperidine-4,2'(1'H)-quinazoline]-4'-amine hydrochloride From the intermediate of Example U(d); yellow crystals, m.p. 234°–236° C.

EXAMPLE 102

1-(4-Cyanobenzoyl)-5'-fluorospiro[piperidine-4,2'(1'H)-quinazoline]-4'-amine hydrochloride.

This was prepared from 1-(4-cyanobenzoyl)-4-piperidone ethylene ketal (Example U(b)) and 2-amino-6-fluorobenzamidine dihydrochloride (Example C) by the method of Example 1, to give the title compound as pale yellow crystals, m.p. 299°–300° C.

The compounds of Examples 103–158 were prepared by the method of Example 102 using the appropriate ketal.

EXAMPLE 103

5'-Fluoro-1-(2-fluorobenzoyl)spiro[piperidine-4,2'(1'H)-quinazoline]-4'-amine hydrochloride From the intermediate of Example W(nn); yellow glass, MS (+CI) 357 ([M+H]+); 1H NMR (d$_6$-DMSO) 7.37 (5H, m), 6.57 (1H, d, J 7.8 Hz), 6.44 (1H, dd, J 11.4, 8.4 Hz), 3.98 (1H, m), 3.58 (1H, m), 3.34 (2H, m), 1.74 (4H, m).

EXAMPLE 104

1-(4-Chlorobenzoyl)-5'-fluorospiro[piperidine-4,2'(1'H)-quinazoline]-4'-amine hydrochloride From the intermediate of Example U(f); pale yellow crystals, m.p. 306°–307° C.

EXAMPLE 105

1-(4-Bromobenzoyl)-5'-fluorospiro[piperidine-4,2'(1'H)-quinazoline]-4'-amine hydrochloride From the intermediate of Example W(b); pale yellow crystals, m.p. 315°–316° C.

EXAMPLE 106

5'-Fluoro-1-(4-iodobenzoyl)spiro[piperidine-4,2'(1'H)-quinazoline]-4'-amine hydrochloride From the intermediate of Example W(c); pale yellow crystals, m.p. 315°–316° C.

EXAMPLE 107

5'-Fluoro-1-(4-nitrobenzoyl)spiro[piperidine-4,2'(1'H)-quinazoline]-4'-amine hydrochloride From the intermediate of Example U(c); pale yellow crystals, m.p. >320° C., MS (+FAB) 384 ([M+]+).

EXAMPLE 108

1-(4-Ethylbenzoyl)-5'-fluorospiro[piperidine-4,2'(1'H)-quinazoline]-4'-amine hydrochloride From the intermediate of Example U(e); yellow crystals, m.p. 287°–289° C.

EXAMPLE 109

5'-Fluoro-1-(4-propylbenzoyl)spiro[piperidine-4,2'(1'H)-quinazoline]-4'-amine hydrochloride From the intermediate of Example W(tt); yellow crystals, m.p. 246°–248° C.

EXAMPLE 110

1-(4-Butylbenzoyl)-5'-fluorospiro[piperidine-4,2'(1'H)-quinazoline]-4'-amine hydrochloride From the intermediate of Example W(uu); yellow foam, MS (+CI) 395 ([M+H]+), 1H NMR (d$_6$-DMSO) 7.4–7.2 (5H, br. m), 6.62 (1H, d, J 8.4 Hz), 6.49 (1H, dd, J 8.1, 12 Hz), 3.93 (1H, br. s), 3.51 (3H, br. s), 2.61 (2H, t, J 7.8 Hz), 2.0–1.6 (4H, br. m), 1.56 (2H, quintet, J 8 Hz), 1.31 (2H, quintet, J 8 Hz), 0.90 (3H, t, J 7.5 Hz).

EXAMPLE 111

1-(4-Ethynylbenzoyl)-5'-fluorospiro[piperidine-4,2'(1'H)-quinazoline]-4'-amine hydrochloride From the intermediate of Example W(hh); yellow crystals, m.p. 302°–305° C. (dec.).

EXAMPLE 112

5'-Fluoro-1-((4-aminosulphonyl)benzoyl)spiro[peridine-4,2'(1'H)-quinazoline]-4'-amine hydrochloride From the intermediate of Example W(h); pale yellow crystals, m.p. 287°–289° C.

EXAMPLE 113

5'-Fluoro-1-((4-methanesulphonyl)benzoyl)spiro[piperidine-4,2'(1'H)-quinazoline]-4'-amine hydrochloride From the intermediate of Example W(e); pale yellow crystals, m.p. 297°–298° C.

EXAMPLE 114

5'-Fluoro-1-(4-(trifluoromethoxy)benzoyl)spiro[piperidine-4,2'(1'H)-quinazoline]-4'-amine hydrochloride From the intermediate of Example W(bb); yellow foam, MS (+FAB) 423 ([M+H]+), 1H NMR (d$_6$-DMSO) 7.53 (2H, d, J 8.6 Hz), 7.45 (2H, d, J 8.2 Hz), 7.34 (1H, d, J 6.6 Hz), 6.65 (1H, d, J 8.2 Hz), 6.50 (1H, dd, J 8.3, 11.8 Hz), 3.95 (1H, br. s), 3.65–3.4 (3H, br. m), 2.0–1.71 (4H, m).

EXAMPLE 115

Methyl 4-(4'-Amino-5'-fluorospiro[piperidine-4,2'(1'H)-quinazoline]-1-ylcarbonyl) -benzoate hydrochloride From the intermediate of Example W(l); yellow glass, MS (+FAB) 397 ([M+H]+), 1H NMR (d$_6$-DMSO) 8.03 (2H, d, J 8.0 Hz), 7.72 (2H, d, J 8.0 Hz), 7.26 (2H, d, J 6.4 Hz), 6.59 (1H, d, J 8.2 Hz), 6.45 (1H, t, J 8.4 Hz), 3.96 (1H, br. s), 3.87 (3H, s) 3.58 (1H, br. s), 3.35 (2H, br. s), 1.90 (1H, br. s), 1.77 (2H, br. s), 1.62 (2H, br. s).

EXAMPLE 116

4-(4'-Amino-5'-fluorospiro[piperidine-4,2'(1'H)-quinazoline]-1-ylcarbonyl)-N-(2-hydroxyphenyl)benzamide hydrochloride From the intermediate of Example AA; yellow crystals, m.p. 273°–275° C.

EXAMPLE 117

4-(4'-Amino-5'-fluorospiro[piperidine-4,2'(1'H)-quinazoline]-1-ylcarbonyl)-N-(4-methoxyphenyl)benzamide hydrochloride From the intermediate of Example BB; yellow crystals, m.p. 243°–245° C.

EXAMPLE 118

5'-Fluoro-1-(4-(2-thiazolyl)benzoyl)spiro[piperidine-4,2'(1'H)-quinazoline]-4'-amine hydrochloride From the intermediate of Example CC; yellow crystals, m.p. >270° C., MS (+CI) 422 ([M+H]+).

EXAMPLE 119

1-(3,4-Dichlorobenzoyl)-5'-fluorospiro[piperidine-4,2'(1'H)-quinazoline]-4'-amine hydrochloride From the intermediate of Example W(x); yellow crystals, m.p. 262°–264° C.

EXAMPLE 120

1-(4-Chloro-3-iodobenzoyl)-5'-fluorospiro[piperidine-4,2'(1'H)-quinazoline]-4'-amine hydrochloride From the intermediate of Example W(rr); yellow crystals, m.p. 264°–266° C.

EXAMPLE 121

1-(4-Cyano-3-methylbenzoyl)-5'-fluorospiro[piperidine-4,2'(1'H)-quinazoline]-4'-amine hydrochloride From the intermediate of Example Y; yellow crystals, m.p. 302°–303° C.

EXAMPLE 122

1-(4-Cyano-3-fluorobenzoyl)-5'-fluorospiro[piperidine-4,2'(1'H)-quinazoline]-4'-amine hydrochloride From the intermediate of Example Z; yellow crystals, m.p. 301°–303° C.

EXAMPLE 123

5'-Fluoro-1-(2-furylcarbonyl)spiro[piperidine-4,2'(1'H)-quinazoline]-4'-amine hydrochloride From the intermediate of Example U(d); yellow crystals, m.p. 231°–233° C.

EXAMPLE 124

5'-Fluoro-1-(2-thienylcarbonyl)spiro[piperidine-4,2'(1'H)-quinazoline]-4'-amine hydrochloride From the intermediate of Example U(k); yellow crystals, m.p. 264°–265° C.

EXAMPLE 125

5'-Fluoro-1-(3-thienylcarbonyl)spiro[piperidine-4,2'(1'H)-quinazoline]-4'-amine hydrochloride From the intermediate of Example W(ee); yellow crystals, m.p. 285°–287° C.

EXAMPLE 126

1-(4-Bromo-2-thienylcarbonyl)-5'-fluorospiro[piperidine-4,2'(1'H)-quinazoline]-4'-amine hydrochloride From the intermediate of Example W(y); yellow crystals, m.p. 209°–211° C.

EXAMPLE 127

1-(5-Bromo-3-thienylcarbonyl)-5'-fluorospiro[piperidine-4,2'(1'H)-quinazoline]-4'-amine hydrochloride From the intermediate of Example W(o); pale yellow crystals, m.p. 251°–252° C.

EXAMPLE 128

5'-Fluoro-1-(5-chloro-2-thienylcarbonyl)spiro[piperidine-4,2'(1'H)-quinazoline]-4'-amine hydrochloride From the intermediate of Example W(j); yellow crystals, m.p. 257°–259° C.

EXAMPLE 129

1-(5-Bromo-2-thienylcarbonyl)-5'-fluorospiro[piperidine-4,2'(1'H)-quinazoline]-4'-amine hydrochloride From the intermediate of Example W(zz); yellow crystals, m.p. 258°–259° C.

EXAMPLE 130

5'-Fluoro-1-(5-methyl-2-thienylcarbonyl)spiro[piperidine-4,2'(1'H)-quinazoline]-4'-amine hydrochloride From the intermediate of Example W(mm); yellow foam, MS (+CI) 359 ([M+H]+), 1H NMR ($d_6$-DMSO) 7.31 (1H, q, J 7.6 Hz), 7.22 (1H, d, J 3.6 Hz), 6.83 (1H, d, J 3.6 Hz), 6.63 (1H, d, J 8.4 Hz), 6.51 (1H, dd, J 10.5, 8.7 Hz), 3.84 (2H, m), 3.66 (2H, m), 2.50 (3H, s), 1.88 (2H, m), 1.73 (2H, m).

EXAMPLE 131

1-(5-Ethyl-2-thienylcarbonyl)-5'-fluorospiro[piperidine-4,2'(1'H)-quinazoline]-4'-amine hydrochloride From the intermediate of Example W(yy); yellow crystals, m.p. 252°–254° C.

EXAMPLE 132

5'-Fluoro-1-(1H-pyrrol-2-ylcarbonyl)spiro[piperidine-4,2'(1'H)-quinazoline]-4'-amine hydrochloride From the intermediate of Example DD; light brown crystals, m.p. 255°–257° C.

EXAMPLE 133

5'-Fluoro-1-(1-methyl-1H-pyrrol-2-ylcarbonyl)spiro[piperidine-4,2'(1'H)-quinazoline]-4'-amine hydrochloride From the intermediate of Example W(ll); pale brown glass, MS (+ESI) 342 ([M+H]+), 1H NMR ($d_6$-DMSO) 7.53 (1H, br. s), 7.34 (1H, q, J 6.4 Hz), 6.90 (1H, s), 6.65 (1H, d, J 8.3 Hz), 6.52 (1H, dd, J 11.6, 8.4 Hz), 6.29 (1H, s), 6.03 (1H, t, J 3.2 Hz), 3.87 (2H, m), 3.67 (3H, s), 3.64 (2H, m), 1.89 (2H, m), 1.73 (2H, m).

EXAMPLE 134

5'-Fluoro-1-(3-isoxazolylcarbonyl)spiro[piperidine-4,2'(1'H)-quinazoline]-4'-amine hydrochloride From the intermediate of Example W(oo); yellow glass, MS (+CI) 330 ([M+H]+), 1H NMR ($d_6$-DMSO) 9.10 (1H, d, J 1.8 Hz), 7.27 (1H, q, J 7.4 Hz), 6.83 (1H, d, J 1.8 Hz), 6.59 (1H, d, J 8.1 Hz), 6.46 (1H, dd, J 11.7, 8.1 Hz), 3.99 (1H, m), 3.64 (3H, m), 1.89 (2H, m).

EXAMPLE 135

5'-Fluoro-1-(5-isoxazolylcarbonyl)spiro[piperidine-4,2'(1'H)-quinazoline]-4'-amine hydrochloride From the intermediate of Example U(n); pink crystals, m.p. 220°–221° C.

EXAMPLE 136

5'-Fluoro-1-(2-thiazolylcarbonyl)spiro[piperidine-4, 2'(1'H)-quinazoline]-4'-amine hydrochloride From the intermediate of Example W(jj); yellow crystals, m.p. 247° C. (dec.).

EXAMPLE 137

5'-Fluoro-1-(5-thiazolylcarbonyl)spiro[piperidine-4, 2'(1'H)-quinazoline]-4'-amine hydrochloride From the intermediate of Example SS; yellow crystals, m.p. 257°–259° C.

EXAMPLE 138

1-(2-(3-Bromo-2-thienyl)-5-thiazolylcarbonyl)-5'-fluorospiro[piperidine-4,2'(1H)-quinazoline]-4'-amine hydrochloride From the intermediate of Example W(pp); yellow crystals, m.p. 231°–233° C.

EXAMPLE 139

5'-Fluoro-1-(4-isothiazolylcarbonyl)spiro[piperidine-4,2'(1'H)-quinazoline]-4'-amine hydrochloride From the intermediate of Example W(vv); light brown crystals, m.p. 267°–269° C. (dec.).

EXAMPLE 140

5'-Fluoro-1-(1,2,3-thiadiazol-4-ylcarbonyl)spiro[piperidine-4,2'(1'H)-quinazoline]-4'-amine hydrochloride From the intermediate of Example W(ww); yellow crystals, m.p. 254°–255° C.

EXAMPLE 141

5'-Fluoro-1-(4-pyridylcarbonyl)spiro[piperidine-4,2'(1'H)-quinazoline]-4'-amine hydrochloride From the intermediate of Example W(s); yellow crystals, m.p. 283°–285° C.

EXAMPLE 142

5'-Fluoro-1-(3-pyridylcarbonyl)spiro[piperidine-4,2'(1'H)-quinazoline]-4'-amine hydrochloride From the intermediate of Example W(i); yellow crystals, m.p. 220°–223° C.

EXAMPLE 143

1-(6-Chloro-3-pyridylcarbonyl)-5'-fluorospiro[piperidine-4,2'(1'H)-quinazoline]-4'-amine hydrochloride From the intermediate of Example W(n); pale yellow crystals, m.p. 297°–298° C.

EXAMPLE 144

1-(6-Cyano-3-pyridylcarbonyl)-5'-fluorospiro[piperidine-4,2'(1'H)-quinazoline]-4'-amine hydrochloride From the intermediate of Example RR; yellow crystals, m.p. 274°–276° C.

EXAMPLE 145

5'-Fluoro-1-(2-pyrazinylcarbonyl)spiro[piperidine-4, 2'(1'H)-quinazoline]-4'-amine hydrochloride From the intermediate of Example W(aa); yellow glass, MS (+FAB) 341 ([M+H]+), 1H NMR ($d_6$-DMSO)8.84 (1H, d, J 1.2 Hz), 8.75 (1H, d, J 2.5 Hz), 8.68 (1H, d, J 1.5 Hz), 7.30 (1H, d, J 7.0 Hz), 6.62 (1H, d, J 8.1 Hz), 6.48 (1H, dd, J 8.4, 11.5 Hz), 4.08–4.00 (1H, m), 3.66–3.50 (3H, m), 2.0–1.73 (4H, m).

EXAMPLE 146

5'-Fluoro-1-(5-methyl-2-pyrazinylcarbonyl)spiro[piperidine-4.2'(1'H)-quinazoline]-4'-amine hydrochloride From the intermediate of Example W(ff); yellow crystals, m.p. 282°–283° C.

EXAMPLE 147

5'-Fluoro-1-(2-naphthylcarbonyl)spiro[piperidine-4, 2'(1'H)-quinazoline]-4'-amine hydrochloride From the intermediate of Example W(qq); yellow crystals, m.p. 199°–201° C.

EXAMPLE 148

5'-Fluoro-1-(2-benzo[b]thienylcarbonal)spiro[piperidine-4,2'(1'H)-quinazoline]-4'-amine hydrochloride From the intermediate of Example W(xx); yellow crystals, m.p. 267°–268° C. (dec.).

EXAMPLE 149

5'-Fluoro-1-(6-quinolylcarbonyl)spiro[piperidine-4,2'(1'H)-quinazoline]-4'-amine hydrochloride From the intermediate of Example W(gg); yellow crystals, m.p. 267°–269° C.

EXAMPLE 150

1-(1,3-Benzodioxol-5-ylcarbonyl)-5'-fluorospiro[piperidine-4,2'(1'H)-quinazoline]-4'-amine hydrochloride From the intermediate of Example W(cc); yellow crystals, m.p. 294°–296° C.

EXAMPLE 151

1-(5-Benzofuroxanylcarbonyl)-5'-fluorospiro[piperidine-4,2'(1'H)-quinazoline]-4'-amine hydrochloride From the intermediate of Example W(z); yellow crystals, m.p. 280°–282° C.

EXAMPLE 152

1-(1,3-Dihydro-1,3-dioxo-2H-isoindol-5-ylcarbonyl)5'-fluorospiro[piperidine-4,2'(1'H)-quinazoline]-4'-amine hydrochloride From the intermediate of Example W(dd); yellow crystals, m.p. 312°–315° C.

EXAMPLE 153

O-Ethyl 4'-amino-5'-fluorospiro[piperidine-4,2'-[1'H]-quinazoline]-1-carbothioate hydrochloride From the intermediate of Example HH; bright yellow powder, m.p. 224°–225° C.

EXAMPLE 154

5'-Fluoro-1-(2-thienyl)iminomethylspiro[piperidine-4,2'-[1'H]-quinazoline]-4'-amine dihydrochloride From the intermediate of Example II; m.p. >270° C., MS (APCI+) 344 ([M+H]+).

EXAMPLE 155

1-((4-Cyanopheyl)thioxomethyl)-5'-fluorospiro[piperidine-4,2'(1'H)-quinazoline]-4'-amine hydrochloride From the intermediate of Example QQ; yellow crystals, m.p.>250° C., MS (+CI) 380 ([M+H]+).

EXAMPLE 156

5'-Fluoro-1-(trifluoroacetyl)spiro[piperidine-4,2'(1'H)-quinazoline]-4'-amine hydrochloride From the intermediate of Example X; yellow crystals, m.p.>250° C., MS (+CI) 331 ([M+H]+).

EXAMPLE 157

5'-Fluoro-1-(4-phenoxybutanoyl)spiro[piperidine-4,2'(1'H)-quinazoline]-4'-amine hydrochloride From the intermediate of Example W(ii); bright yellow crystals, m.p. 114°–116° C.

EXAMPLE 158

3-(Methanesulphonyl)propyl 4'-amino-5'-fluorospiro[piperidine-4,2'-[1'H]-quinazoline]-1-carboxylate hydrochloride From the intermediate of Example GG as a yellow foam, MS (+CI) 399 ([M+H]+), 1H NMR ($d_6$-DMSO) 10.53 (1H, s), 8.86 (1H, s), 8.06 (1H, s), 7.25 (1H, dd), 6.76 (1H, d), 6.66 (1H, dd), 4.12 (2H, t), 3.68–3.51 (4H, m), 3.2 (2H, t), 2.99 (3H, s), 2.0 (4H, m), 1.78 (2H, m).

The compounds of Examples 159–162 were prepared by the method of Example 102 using 2-fluoro-6-(methylamino)benzamidine dihydrochloride (Example J) and appropriate ketals.

EXAMPLE 159

5'-Fluoro-1'-methyl-1-(2-thienylcarbonyl)spiro[piperidine-4,2'(1'H)-quinazoline]-4'-amine hydrochloride Yellow glass, MS (+CI) 359 ([M+H]); 1H NMR ($d_6$-DMSO) 7.75 (1H, d, J 5.1 Hz), 7.43 (1H, m), 7.39 (1H, q, J 7.2 Hz), 7.12 (1H, m), 6.69 (1H, d, J 8.5 Hz), 6.59 (1H, dd, J 11.0, 8.6 Hz), 4.21 (2H, br. s), 3.35 (2H, br. s), 1.91 (2H, br. s), 1.74 (2H, br. s).

EXAMPLE 160

5'-Fluoro-1'-methyl-1-(4-cyanobenzoyl)spiro[piperidine-4,2'(1 'H)-quinazoline]-4'-amine hydrochloride Bright yellow solid, m.p. 303°–304° C.

EXAMPLE 161

1-((4-Aminosulphonyl)benzoyl)-5'-fluoro-1'-methyl-spiro[piperidine-4,2'(1'H)-quinazoline]-4'-amine hydrochloride Bright yellow solid, mn.p. 274°–276° C. (dec.).

EXAMPLE 162

1-(4-Cyanobenzoyl)-5',8'-difluorospiro[piperidine-4,2'(1'H)-quinazoline]-4'-amine hydrochloride This was prepared with 2-amino-3,6-difluorobenzamidine dihydrochloride (Example G) and 1-(4-cyanobenzoyl)-4-piperidone ethylene ketal by the method of Example 1 to give the title compound as a yellow solid, m.p >270° C., MS (+CI) 382 ([M+H]+).

The compounds of Examples 163–167 were prepared by the method of Example 162.

EXAMPLE 163

1-(4-Chlorobenzoyl)-5',8'-difluorospiro[piperidine-4,2'(1'H)-quinazoline-]4'-amine hydrochloride From the intermediate of Example U(f); m.p.>250° C., MS (+CI) 391 ([M+H]+).

EXAMPLE 164

5',8'-difluoro-1-(2-thienylcarbonyl)spiro[piperidine-4,2'(1'H)-quinazoline]-4'-amine hydrochloride From the intermediate of Example U(k); m.p.>250° C., MS (APCI+) 363 ([M–HCl+H]+).

EXAMPLE 165

5',8'-Difluoro-1-(2-pyrazinylcarbonyl)spiro[piperidine-4,2'(1'H)-quinazoline]-4'-amine hydrochloride From the intermediate of Example W(aa); m.p. 140° C. (dec.).

EXAMPLE 166

1-(6-Chloro-3-pyridylcarbonyl)-5',8'-difluorospiro[piperidine-4,2'(1')-quinazoline]-4'-amine hydrochloride From the intermediate of Example W(n); m.p. >246° C., MS (+CI) 392/394 ([M+H]+).

EXAMPLE 167

1-(6-Cyano-3-pyridylcarbonyl)-5',8'-difluorospiro[piperidine-4,2'(1'H)-quinazoline]-4'-amine dihydrochloride From the intermediate of Example RR: m.p. 297°–298° C.

EXAMPLE 168

1-(4-Cyanobenzoyl)-5',7'-difluorospiro[piperidine-4,2'(1'H)-quinazoline]-4'-amine hydrochloride.

This was prepared with 2-amino4,6-difluorobenznmidine dihydrochloride (Example H) and 1-(4-cyanobenzoyl)-4piperidone ethylene ketal (Example U(b)) by the method of Example 1 to give the title compound, m.p>250° C., MS (+CI) 382 ([M+H]+).

EXAMPLE 169

5',7'-Difluoro-1-(2-thienylcarbonyl)spiro[piperidine-4,2'(1'H)-quinazoline]-4'-amine hydrochloride This was prepared by the method of Example 168 using 1-(2-thienylcarbonyl)4-piperidone ethylene ketal (Example U(k)). Yellow solid, m.p. 241°–243° C.

EXAMPLE 170

1-(4-Cyanobenzoyl)-5'-methoxyspiro[piperidine-4,2'(1'H)-quinazoline]-4'-amine hydrochloride.

This was prepared with 2-amino-6-methoxybenzamidine dihydrochloride (Example E) and 1-(4-cyanobenzoyl)-4-piperidone ethylene ketal by the method of Example 1 to give the title compound as a yellow solid, m.p. 252°–253° C.

The compounds of Examples 171 and 172 were prepared by the method of Example 1 using 2-amino-6-hydroxybenzamidine dihydrochloride (Example D) and the appropriate ketal.

EXAMPLE 171

1-(4-Bromobenzoyl)-5'-hydroxyspiro[piperidine-4,2'(1'H)-quinazoline]-4'-amine hyrochloride From the intermediate of Example W(b); yellow solid, MS (+CI) 415/417 ([M+H]+), 1H NMR ($d_6$-DMSO) 8.61 (1H, s), 8.27 (1H, s), 7.68 (2H, d), 7.54 (1H, s), 7.36 (2H, d), 7.25 (1H, t), 6.35 (1H, d), 6.27 (1H, d), 3.2–3.9 (4H, m), 1.5–2.1 (4H, m).

EXAMPLE 172

1-(4-Cyanobenzoyl)-5'-hydroxyspiro[piperidine-4,2'(1'H)-quinazoline]-4'-amine hydrochloride From the intermediate of Example U(b); yellow solid, MS (APCI+) 362 ([M−HCl+H]+), 1H NMR ($d_6$-DMSO) 11.80 (H, s), 8.65 (H, s), 8.46 (H, s), 7.96 (2H, d), 7.58 (2H, d), 7.54 (H, s), 7.24 (H, t), 6.35 (H, d), 6.27 (H, d), 3.8–4.0 (2H, m), 3.63–3.8 (2H, m), 1.6–2.1 (4H, m).

EXAMPLE 173

Ethyl 4'-aminospiro[piperidine-4,2'(1'H)-quinazoline]1-carboxylate hydrochloride A solution of 2-aminobenzamidine dihydrochloride (416 mg, 2 mmol) and 1-carb-ethoxy4-piperidone (342 mg, 2 mmol) in ethanol (10 ml) was heated at reflux for 4 hours. The solution was cooled and the solvent evaporated. The residue was triturated with ethanol and ether to afford the title compound (550 mg) as a bright yellow powder, m.p. 192°–194° C. (dec.).

The compounds of Examples 174–177 were prepared using the method of Example 173.

EXAMPLE 174

1-Acetylspiro[piperidine-4,2'(1'H-quinazoline]-4'-amine

From 1-acetyl-4-piperidone; purified as the maleate salt; m.p. 213°–215° C.

EXAMPLE 175

Methyl 4'-ainospiro[piperidine-4,2'(1'H)-quinazoline]-1-carboxylate hydrochloride From methyl 4-oxopiperidine-1-carboxylate; m.p. 195°–197° C.

EXAMPLE 176

1-Methylethyl 4'-aminospiro([piperidine-4,2'(1'H)-quinazoline]-1-carboxylate hydrochloride From isopropyl 4-oxopiperidine-1-carboxylate; m.p. 229°–232° C.

EXAMPLE 177

1-Benzoylspiro[piperidine-4,2'(1'H)-quinazoline]-4'-amine hydrochloride

From 1-benzoyl-4-piperidone; m.p. 210°–212° C.

EXAMPLE 178

Ethyl 4'-amino-5'-chlorospiro[piperidine-4,2'(1'H)-quinazoline]-1-carboxylate hydrochloride This was prepared by the method of Example 173 using 2-chloro-6-anino benzamidine dihydrochloride (Example B) and ethyl 4-oxopiperidine-1-carboxylate giving the title compound, m.p. 181°–183° C.

The compounds of Examples 179 and 180 were prepared by the method of Example 173 using 2-fluoro-6-aminobenzamidine dihydrochloride (Example C) and the appropriate ketone.

EXAMPLE 179

Ethyl 4'-amino-5'-fluorospiro[piperidine-4,2'(1'H)-quinazoline]-1-carboxylate hydrochloride From ethyl 4-oxopiperidine-1-carboxylate; m.p. 187°–189° C.

EXAMPLE 180

1-Benzoyl-5'-fluorospiro[piperidine-4,2'(1'H)-quinazoline]-4'-amine hydrochloride From 1-benzoyl-4-piperidone; m.p. 268°–270° C. (dec.).

EXAMPLE 181

Ethyl 4'-amino-5'-hydroxyspiro[piperidine-4,2'(1'H)-quinazoline]-1-carboxylate hydrochloride This was prepared by the method of Example 173 using 2-hydroxy-6-aminobenzamidine dihydrochloride (Example D) and ethyl 4-oxopiperidine-1-carboxylate to give the title compound as a yellow solid, MS (+CI) 305 ([M+H]+), 1H NMR ($d_6$-DMSO) 11.80 (1H, s), 9.96 (1H, s), 8.64 (1H, s), 8.54 (1H, s), 7.49 (1H, s), 7.23 (1H, t), 6.31 (1H, d), 6.27 (1H, d), 4.02–4.08 (2H, m), 3.5–3.7 (2H, m), 3.3–3.5 (2H, m), 1.6–1.8 (2H, m), 1.19 (3H, t).

EXAMPLE 182

Ethyl 4'-amino-5'-methoxyspiro[piperidine-4,2'(1'H) quinazoline]-1-carboxylate hydrochloride This was prepared by the method of Example 173 using 2-methoxy-6-aminobenzamidine dihydrochloride (Example E) and ethyl 4-oxopiperidine-1-carboxylate to give the title compound as a yellow solid, MS (+CI) 319 ([M+H]+), 1H NMR ($d_6$-DMSO) 9.97 (1H, s), 8.69 (1H, s), 8.64 (1H, s), 7.70 (1H, s), 7.40 (1H, dd), 6.48 (1H, d), 6.42 (1H, d), 4.05 (2H, q), 3.88 (3H, s), 3.6–3.72 (2H, m), 3.4–3.55 (2H, m), 1.85–2.0 (2H, m), 163–1.80 (2H, m), 1.19 (3H, t).

EXAMPLE 183

Ethyl 4'-amino-5'.8'-difluorospiro[piperidine-4,2'(1'H)-quinazoline]-1-carboxylate hydrochloride This was prepared by the method of Example 173 using 2-amino-3,6-difluorobenzamidine dihydrochloride (Example G) and ethyl 4-oxopiperidine-1-carboxylate to give the title compound, m.p. 228°–229° C.

EXAMPLE 184

Ethyl 4'-amino-5'.7'-difluorospiro[piperidine-4,2'(1'H)-quinazoline]-1-carboxylate hydrochloride This was prepared by the method of Example 173 using 2-anino-4,6-difluorobenzamidine dihydrochloride (Example H) and ethyl 4-oxopiperidine-1-carboxylate to give the title compound, m.p. 245°–246° C.

EXAMPLE 185

Ethyl 4'-amino-8'-chloro-5'-fluorospiro[piperidine-4,2'(1'H)-quinazoline]-1-carboxylate 2-Amino-3-chloro-6-fluorobenzamide dihydrochloride [Example I(d)] (100 mg, 0.38 mmol) and 1-carbethoxy-4-piperidone (0.1 ml) were heated together neat at 160° C. for 3 h. The mixture was cooled and taken up in ether. The ethereal solution was decanted and the resulting solid purified by flash chromatography on neutral alumina, eluting with 1% methanol/dichloromethane to give a glass which was triturated with dichloromethane/ether to afford the title compound as a pale yellow/orange powder, m.p. 182°–184° C.

EXAMPLE 186

Ethyl 4'-amino-5'-fluoro-1'-methylspiro[piperidine-4,2'(1'H)-quinazoline]-1-carboxylate hydrochloride This was prepared by the method of Example 173 using 2-fluoro-6-(methylamino)benzamidine dihydrochloride (Example K) and ethyl 4-oxopiperidine-1-carboxylate to give the title compound, m.p. 234°–235° C.

EXAMPLE 187

Ethyl 4'-aminospiro[piperidine-3,2'(1'H)-quinazoline]-1-carboxylate hydrochloride This was prepared by the method of Example 173 using ethyl 3-oxopiperidine-1-carboxylate (P. Duhamel et al., *Tetrahedron Lett.*, 1993, 34, 3863) and 2-aminobenzamidine hyrocioride to give the title compound, MS (+EI) 288 ([M+H]+), 1H NMR (d$_6$-DMSO) (rotamers) 9.83 (1H, s), 9.20 (1H, s), 8.37 (1H, s), 7.86 (1H, d), 7.68 (1H, s), 7.50 (1H, t), 6.91 (1H, d), 6.84 (1H, t), 4.1–3.8 (2H, m), 3.6–3.4 (2H, m), 2.1–1.7 (2H, m), 1.3–0.9 (5H, m).

EXAMPLE 188

Ethyl 4'-aminospiro[pyrrolidine-3,2'(1'H)-quinazoline]-1-carboxylate hydrochloride This was prepared by the method of Example 173 using 2-aminobenzamidine hydrochloride and ethyl 3-oxopyrrolidine-1-carboxylate to give the title compound, MS (+EI) 274 ([M+H]+), 1H NMR (d$_6$-DMSO) (rotamers) 10.48 (1H, s), 9.2–8.2 (2H, m), 7.94 (1H, s), 7.88 (1H, d), 7.49 (1H, t), 6.89 (1H, d), 6.85 (1H, t), 4.04 (2H, dt), 3.6–3.4 (4H, m) 2.86–2.7 (1H, m), 2.09–2.02 (1H, m), 1.18 (3H, dq).

EXAMPLE 189

Propyl 4'-amino-5'-fluorospiro[piperidine-4,2'(1'H)-quinazoline]-1-carboxylate hydrochloride Propyl chloroformate (0.47 ml, 4.2 mmol) was added dropwise to a solution of 4-piperidone ethylene ketal (0.57 ml, 1.0 equiv.) and pyridine (0.67 ml, 2.0 equiv.) in dichloromethane. The solution was stirred for 2 h, diluted with aqueous HCl (1.0M) and extracted with diethyl ether. The organic extracts were dried (sodium sulphate) and evaporated to give crude propyl 4-oxopiperidine-1-carboxylate ethylene ketal as a colourless oil. A solution of 2-amino-6-fluorobenzamidine dihydrochloride (200 mg, 0.88 mmol) and the crude ketal (500 mg) in ethanol (10 ml) and HCl(3 ml, 1M in ether) was refluxed for 12 h, cooled and evaporated. The residue was purified by flash column chromatography on untreated alumina eluting with dichloromethane to dichloromethane/methanol (10:1) to give a yellow foam which was triturated with ethanol/dichloromethane/ether to yield the product as a bright yellow powder, m.p. 209°–210° C.

The compounds of examples 190–194 were prepared following the method of Example 189.

EXAMPLE 190

Methyl 4'-amino-5'-fluorospiro[piperidine-4,2'-[1'H]quinazoline]-1-carboxylate hydrochloride From methyl chloroformate; bright yellow powder, m.p. 252°–25° C.

EXAMPLE 191

2-Methylpropyl 4'-amino-5'-fluorospiro[piperidine-4,2'-[1'H]-quinazoline]-1 -carboxylate hydrochloride From isobutyl chmoroformate; bright yellow powder, m.p. 202°–203° C.

EXAMPLE 192

Cyclopentvl 4'-amino-5'-fluorospiro[piperidine-4,2'-[1'H]-quinazoline]-1-carboxylate hydrochloride From cyclopenyl chloroformate; bright yellow powder, m.p. 180°–181° C.

EXAMPLE 193

2-methoxyethyl 4'-amino-5'-fluorospiro[piperidine-4,2'-[1'H]-quinazoline]-carboxylate hydrochloride From 2-methoxyethyl chloroformate; bright yellow powder, m.p. 102°–103° C.

EXAMPLE 194

S-Ethyl 4'-amino-5'-fluorospiro[piperidine-4,2'-[1'H]quinazoline]-1-carbothioate hydrochloride From (ethylthio)carbonyl chloride; bright yellow powder, m.p. 255°–256° C.

EXAMPLE 195

2-Phenoxyethyl 4'-amino-5'-fluorospiro[piperidine-4,2'-[1'H]-quinazoline]-1-carboxylate hydrochloride A solution of 2-phenoxyethanol (0.47 ml, 4.2 mmol) and 1,1'-carbonyldiimidazole (1.16 g, 1.0 eq.) in acetonitrile (10 ml) was stirred for 5 h. 4-piperidone ethylene ketal (0.82 ml, 1.0 eq.).was added, the solution was heated at 70° C. for 17 h and then cooled and evaporated to give the crude 2-phenoxyethyl 4oxopiperidine-1-carboxylate ethylene ketal. A solution of 2-amino-6-fluorobenzamidine dihydrochloride (200 mg, 0.88 mmol) and the crude ketal (500 mg) in ethanol (10 ml) and HCl (3 ml, 1N in ether) was refluxed for 12 h, cooled and evaporated. The residue was purified by flash column chromatography on untreated neutral alumina eluting with dichloromethane, increasing the gradient to 10% methanol in dichloromethane, to give a yellow foam, which was triturated with ethanol/dichloromethane/ether to yield a bright yellow powder, m.p. 105°–106° C.; MS (+FAB) 399 ([M+H]+).

The compounds of Examples 196–235 were prepared by the method of Example 195, using the appropriate alcohol.

EXAMPLE 196

1-Methylethyl 4'-amino-5'-fluorospiro[piperidine-4, 2'(1'H)-quinazoline]-1-carboxylate hydrochloride Bright yellow powder, m.p. 260°–261° C.

EXAMPLE 197

Butyl 4'-amino-5'-fluorospiro[piperidine-4,2'(1'H)-quinazoline]-1-carboxylate hydrochloride Bright yellow powder, m.p. 121°–122° C.

EXAMPLE 198

Pentyl 4'-amino-5'-fluorospiro[piperidine-4,2'(1'H)-quinazoline]-1 -carboxylate hydrochloride Bright yellow powder, m.p. 95°–96° C.

EXAMPLE 199

Hexyl 4'-amino-5'-fluorospiro[piperidine-4,2'(1'H)-quinazoline]-1-carboxylate hydrochlorid Bright yellow powder, m.p. 80°–81° C.

EXAMPLE 200

Cyclobutyl 4'-amino-5'-fluorospiro[piperidine-4,2'(1'H)-quinazoline]-1-carboxylate hydrochloride Yellow solid, m.p. 205°–206° C.

EXAMPLE 201

Prop-2-yn-1-yl 4'-amino-5'-fluorospiro[piperidine-4, 2'(1'H)-quinazoline]-1-carboxylate hydrochloride Bright yellow powder, m.p. 145°–150° C.

EXAMPLE 202

But-3-yn-1-yl 4'-amino-5'-fluorospiro[piperdine-4,2' (1'H)-quinazoline]-1-carboxylate hyochloride Bright yellow powder, m.p. 209°–210° C.

EXAMPLE 203

Pent-4-yn-1 -yl 4'-amino-5'-fluorospiro[piperidine-4, 2'(1'H)-quinazoline]-1carboxylate hydochloride Bright yellow foam, MS (+CI) 345 ([M+HI+), 1H NMR (d₆-DMSO) 10.46 (1H, s), 8.84 (1H, s), 8.56 (1H, s), 8.05 (1H, s), 7.5 (1H, m), 6.76 (1H, d), 6.65 (1H,dd), 4.06 (2H, t), 3.64–3.5 (4H, m), 2.84 (1H, t), 2.24 (2H, m), 1.96 (2H, m), 1.76 (2H, m).

EXAMPLE 204

Hex-5-yn-1-yl 4'-amino-5'-fluorospiro[piperidine-4, 2'(1'H)-qiuinazoline]-1-carboxylate hydrochloride Bright yellow foam, MS (+CI) 359 ([M+H]+), 1H NMR (d₆-DMSO) 10.46 (1H, s), 8.84 (1H, s), 8.56 (1H, s), 8.04 (1H, s), 7.5 (1H, m), 6.76 (1H, d), 6.65 (1H, dd), 404 (2H, t), 3.66–3.5 (4H, m), 2.8 (1H, t), 2.19 (2H, t), 1.77–1.96 (4H, m), 1.66 (2H, m), (1.52 2H, m).

EXAMPLE 205

2.2.2-Trifluoroethyl 4'-amino-5'-fluorospiro [piperidine-4,2'(1'H)-quinazoline]-1-carboxylate hydrochloride Bright yellow powder, m.p. 175°–176° C.

EXAMPLE 206

4.4.4-Trifluorobutyl 4'-amino-5'-fluorospiro [piperidine-4,2'(1'H)-quinazoline]-1-carboxylate hydrochloride Bright yellow powder, m.p. 206°–207° C.

EXAMPLE 207

3 -Chloropropyl 4'-amino-5'-fluorospiro[piperidine-4,2'(1'H)-quinazoline-]-1-carboxylate hydrochloride Bright yellow powder, m.p. 183°–184° C.

EXAMPLE 208

4-Chlorobutyl 4'-amino-5'-fluorospiro[piperidine-4, 2'(1'H)-quinazoline]-1-carboxylate hydrochloride Bright yellow powder, m.p. 206°–207° C.

EXAMPLE 209

5-Chloropentyl 4'-amino-5'-fluorospiro[piperidine-4, 2'(1'H)-quinazoline]-1-carboxylate hydrochloride Bright yellow powder, m.p. 170°–172° C.

EXAMPLE 21

6-Chlorohexyl 4'-amino-5'-fluorospiro[piperidine-4, 2'(1'H)-quinazoline]-1-carboxylate hydrochloride Bright yellow powder, m.p. 75°–76° C.

EXAMPLE 211

2-Cyanoethyl 4'-amino-5'-fluorospiro[piperidine-4,2' (1'H)-quinazoline]-1-carboxylate hydrochloride Bright yellow powder, m.p. 182°–183° C.

EXAMPLE 212

2-(Methylthio)ethyl 4'-amino-5'-fluorospiro [piperidine-4,2'(1'H)-quinazoline]-1-carboxylate hydrochloride Bright yellow powder, m.p. 111°–113° C.

EXAMPLE 213

3-(Methylthio)lpropyl 4'-amino-5'-fluorospiro[piperidine-4,2'(1'H)-quinazoline]-1-carboxylate hydrochloride Bright yellow powder, m.p. 108°–109° C.

EXAMPLE 214

2-Phenylethyl 4'-amino-5'-fluorospiro[piperidine-4,2'(1'H)-quinazoline]-1-carboxylate hydrochloride Bright yellow powder, m.p. 110°–112° C.

EXAMPLE 215

3-Phenylpropyl 4'-amino-5'-fluorospiro[piperidine-4,2'-(1'H)quinazoline]-1-carboxylate hydrochloride Bright yellow powder, m.p. 111°–113° C.

EXAMPLE 216

4-Phenylbutyl 4'-amino-5'-fluorospiro[piperidine-4,2'(1'H)-quinazoline]-1-carboxylate hydrochloride Bright yellow powder, m.p. 103°–104° C.

EXAMPLE 217

2-(2-Pyridyl)ethyl 4'-amino-5'-fluorospiro[piperidine-4,2'(1'H)-quinazoline]-1-carboxylate hydrochloride Bright yellow powder, m.p. 142°–143° C.

EXAMPLE 218

2-(3-Pyridyl)ethyl 4'-amino-5'-fluorospiro[piperidine-4,2'(1'H)-quinazoline]-1-carboxylate hydrochloride Bright yellow powder, m.p. 224°–225° C.

EXAMPLE 219

3-(2-Pyidyl)propyl 4'-amino-5'-fluorospiro[piperidine-4,2'(1'H)-quinazoline]-1-carboxylate hydrochloride Hygroscopic yellow powder, MS (FAB+) 398 ([M+H]+), 1H NMR ($d_6$-DMSO) 10.5 (1H, s), 8.5 (1H, s), 8.49 (1H, d), 8.00 (1H, s), 7.69 (1H, t), 7.47 (1H, q) 7.27 (1H, d), 7.20 (1H, dd), 6.75 (1H, d), 6.64 (1H, dd), 4.05 (2H, t), 3.55–3.7 (2H, m), 3.4–3.5 (2H, m), 2.80 (2H, t), 1.9–2.1 (4H, m), 1.7–1.8 (2H, m).

EXAMPLE 220

2-(2-Pyrdylthioethyl 4'-amino-5'-fluorospiro[piperidine-4,2'(1'H)-quinazoline]-1-carboxylate hydrochloride Bright yellow powder, m.p. 112°–114° C.

EXAMPLE 221

2-(Phenylthio)ethyl 4'-amino-5'-fluorospiro[piperidine-4,2'(1'H)-quinazoline]-1-carboxylate hydrochloride Bright yellow powder, m.p. 116°–117° C.

EXAMPLE 222

2-(Phenylamino)ethyl 4'-amino-5'-fluorospiro[piperidine-4,2'(1'H)-quinazoline]-1-carboxylate hydrochloride Bright yellow foam, MS (+CI) 398 ([M+H]+), 1H NMR ($d_6$-DMSO) 10.72 (1H, s), 5 9.0 (1H, s), 8.56 (1H, s), 8.12 (1H, s), 7.5 (1H, ddd), 7.24 (1H, t), 6.95 (1H, m), 6.76 (1H, d), 6.64 (1H, dd), 4.26 (2H, t), 3.69 (2H, s), 3.45 (4H, m), 1.96 (2H, m).

EXAMPLE 223

2-(K-Ethyl-N-phenlamino)ethyl 4'-amino-5'-fluorospiro[piperidine-4,2'(1'H)-quinazoline]-1-carboxylate hydrochloride Bright yellow powder, m.p. 203°–204° C.

EXAMPLE 224

2-(4-Chlorophenoxy)ethyl 4'-amino-5'-fluorospiro[piperidine-4,2'(1'H)-quinazoline]-1-carboxylate hydrochloride Bright yellow powder, m.p. 201°–202° C.

EXAMPLE 225

2-Benzofuranylmethyl 4'-amino-5'-fluorospiro[piperidine-4,2'(1'H)-quinazoline]-1-carboxylate hydrochloride Bright yellow powder, m.p. 126°–127° C.

EXAMPLE 226

3-Phenoxypropyl 4'-amino-5'-fluorospiro[piperidine-4,2'(1'H)-quinazoline]-1-carboxylate hydrochloride Bright yellow powder, m.p. 100°–101 C.

EXAMPLE 227

2-(2-Thienyl)ethyl 4'-amino-5'-fluorospiro[piperidine-4,2'(1'H)-quinazoline]-1-carboxylate hydrochloride Bright yellow powder, m.p. 160°–161° C.

EXAMPLE 228

3-(2-Thienyl)propyl 4'-amino-5'-fluorospiro[piperidine-4,2'(1'H)-quinazoline]-1-carboxylate hydrochloride This was prepared from 2-(3-hydroxypropyl)thiophene: A. A. Macco et al., *J Org. Chem.* 1978, 43, 1591); bright yellow powder, m.p. 93°–94° C.

EXAMPLE 229

4-(2-Thienylbutyl 4'-amino-5'-fluorospiro[piperidine-4,2'(1'H)-quinazoline]-1-carboxylate hydrochloride This was prepared from 2-(4-hydroxybutyl)thiophene (R. M. Acheson and M. W. Cooper, *J. Chem. Soc., Perkin Trans.* 1, 1980, 1185) as a bright yellow foam, MS (+CI) 417 ([M+H]+), 1H NMR ($d_6$-DMSO) 10.42 (1H, s), 8.91 (1H, s), 8.56 (1H, s), 7.5 (1H, m), 7.32 (1H, m), 6.95 (1H, m), 6.85

(1H, d), 6.76 (1H, d), 6.66 (1H, dd), 4.03 (2H, t), 3.64–3.45 (4H, m), 2.83 (1H, t), 1.96–1.76 (2H, m), 1.64 (2H, m).

EXAMPLE 230

2-(Phenylmethoxy)ethyl 4'-amino-5'-fluorospiro[piperidine-4,2'(1'H)-quinazoline]-1-carboxylate hydrochloride Bright yellow powder, m.p. 64°–65° C.

EXAMPLE 231

3-1,3-Dihydro-1,3-dioxo-2H-isoindol-2-yl)propyl 4'-amino-5'-fluorospiro[piperidine-4,2'(1'H)-quinazoline]-1-carboxylate hydrochloride Bright yellow powder, m.p. 199°–201° C.

EXAMPLE 232

3-(2-oxo-1(2H)-pyridyl)propyl 4'-amino-5'-fluorospiro[piperidine-4,2'(1'H)-quinazoline]-1-carboxylate hydrochloride This was prepared from 1-(3-hydroxypropyl)pyridin-2-one H. Sliwa, Bull. Soc. Chim. Fr. 1970, 631), m.p. 194°–195° C.

EXAMPLE 233

2-(?henylmethoxy)phenyl 4'-amino-5'-fluorospiro[piperidine-4,2'(1'H)-quinazoline]-1-carboxylate hydrochloride Bright yellow powder, m.p. 213°–214° C.

EXAMPLE 234

5-Bromo-2-methoxyphenylmethyl 4'-amino-5'-fluorospiro[piperidine-4,2'(1'H)-quinazoline]1-carboxylate hydrochloride Bright yellow powder, m.p. 239°–240° C.

EXAMPLE 235

2-(4-Methyl-5-thiazolyl)ethyl 4'-amino-5'-fluorospiro[piperidine-4,2'(1'H)-quinazoline]-1-carboxylate hydrochloride Bright yellow powder, m.p. 115°–116° C.

EXAMPLE 236

Phenyl 4'-aminospiro[piperidine-4,2'(1'H)-quinazoline]-1-carboxylate hydrochloride This was prepared from 2-aminobenzamidine dihydrochloride (Example A) and phenol using the method of Example 195 to give yellow crystals, MS (+EI) 336 ([M+H]+), 1H NMR (d$_6$-DMSO) 10.38 (1H, s), 9.24 (1H, s), 8.59 (1H, s), 7.86 (1H, d), 7.72 (1H, s), 7.50 (1H, dd), 7.40 (2H, dd), 7.24 (1H, dd), 7.13 (2H, d), 6.95 (1H, d), 6.84 (1H, dd), 3.5–3.9 (4H, m), 1.8–2.1 (4H, m).

EXAMPLE 237

4-Chlorobutyl 4'-amino-5',8'-difluorospiro[piperidine-4,2'(1'H)-quinazoline]-1-carboxylate hydrochloride This was prepared from 2-amino-3,6-difluorobenzamidine hydrochloride (Example G) and 4-chlorobutanol using the method of Example 195 to give yellow crystals, m.p. 189°–190° C.

EXAMPLE 238

4-Chlorobutyl 4'-amino-5'-fluoro-1'-methylspiro piperidine-4,2'-[1'H]-quinazoline]-1-carboxylate hydrochloride This was prepared from 2-(methylamino)-6-fluorobenzamidine hydrochloride (Example K) and 4-chlorobutanol using the method of Example 195 to give yellow crystals, m.p. 178°–180° C.

EXAMPLE 239

4'-Amino-5'-fluoro-1-(1 H-imidazol-1-ylcarbonyl)spiro[piperidine-4,2'(1'H) -quinazoline] hydrochloride 1-(1H-Imidazol-1-ylcarbonyl)-4-piperidone ethylene ketal (Example EE, 156 mg., 0.66 mmol) was added to 2-amino-6-fluorobenzamidine dihydrochloride (150 mg, 0.66 is mmol) in ethanol (10 ml) together with an excess of HCl (1M in ether). This mixture was heated to 55° C. overnight, concentrated in vacuo and purified by flash column chromatography eluting with dichloromethane, increasing the gradient to dichloromethane/methanol (10:1), to give a solid which triturated from ethanol/ether to give yellow crystals, m.p. 260° C. (dec.).

EXAMPLE 240

5'-Fluorospiro[piperidine-4,2'(1'H)-quinazoline]-4'-amine dihydrochloride

To a solution of 2-amino-6-fluorobenzamidine dihydrochloride (Example C, 226 mg, 1 mmol) and 4-piperidone ethylene ketal (143 mg, 1 mmol) in dry ethanol (10 ml) was added IN HCl in ether (1 ml, 1 mmol) and the resulting mixture was heated at reflux for 36 h. The solid which separated on cooling was collected by filtration and recrystallised from ethanol to give the title compound (260 mg) as yellow crystals, m.p. 305°–307° C. (dec.).

EXAMPLE 241

Spiro[piperidine-4,2'(1'H)-quinazoline]-4'-amine dihydrochloride

This was prepared using the method of Example 240 using 2-aminobenzamidine dihydrochloride (Example A), as pale yellow crystals from propan-2-ol, m.p. 271°–272° C. (dec.).

EXAMPLE 242

1-(Phenylmethyl)spiro[piperidine-4,2'(1'H)-quinazoline]-4'-amine dihydrochloride A solution of 2-aminobenzamidine dihydrochloride (2.0 g, 9.6 mmol) and N-benzyl4-piperidone (2.1 ml, 11.5 mmol) in ethanol (40 ml) and HCl (1M in Et$_2$O, 5 ml) was heated at 70° C. for 20 h. Evaporation and flash column chromatography on untreated alumina eluting with DCM/methanol (10:1) gave after trituration from ether a yellow solid, MS (+EI) 307 ([M+H]+), 1H NMR (d$_6$-DMSO) 9.99 (1H, s), 9.1 (1H, s), 8.5 (1H, s), 7.81 (1H, d), 7.53 (1H, s), 7.46 (1H, t), 7.2–7.4 (5H, m), 6.89 (1H, d), 6.79 (1H, dd), 3.52 (2H, s), 2.4–2.6 (4H, m), 1.91 (2H, m), 1.82 (2H, m).

The compounds of Examples 243 and 244 were prepared by the method of Example 242.

EXAMPLE 243

1-(Phenylmethyl)spiro[piperidine-3,2'(1'H)-quinazoline]-4'-amine dihydrochloride Yellow solid, MS (+ESI) 307 ([M+H]+), 1H NMR (d$_6$-DMSO) 9.56 (1H, s), 9.19 (1H, s), 8.69 (1H, s), 7.78 (1H, d), 7.52 (1H, s), 7.2–7.4 (6H, m), 6.89 (1H, d), 6.75 (1H, dd), 3.58 (2H, dd), 2.69 (2H, s), 2.30 (1H, s), 2.19 (1H, s), 1.96 (1H, s), 1.71 (1H, s), 1.55 (1H, s).

EXAMPLE 244

1-(Phenylmethyl)spiro[pyrrolidine-3,2'-[1'H]-quinazoline]4'-amine dihydrochloride Yellow solid, m.p. 242°–243° C.

EXAMPLE 245

5'-Fluoro-1-(phenylmethyl)spiro[piperidine-4,2'-[1'H]-quinazoline-4'-amine dihydrochloride This was prepared by the method of Example 242 using 2-amino-6-fluorobenzamidine dihydrochloride (Example C) to give the product as a yellow solid, m.p. 215°–216° C.

EXAMPLE 246

5'-Fluoro-1-(pyrrolidinylcarbonyl)spiro[piperidine-4,2'(1'H)-quinazoline]-4'-amine hydrochloride 1-(1-pyrrolidinylcarbonyl)-4-piperidone ethylene ketal (120 mg, 0.5 mmol) and 2-amino-6-fluorobenzamidine hydrochloride (113 mg, 0.5 mmol) in dry acetonitrile (10 ml) were heated at reflux for 18 h. The mixture was cooled and filtered and the filtrate treated with an equal volume of dry ether. After standing in the refrigerator overnight the pale yellow solid which separated was filtered, washed with dry ether and dried to give the title compound (55 mg), m.p. 246°–248° C. (dec.).

EXAMPLE 247

4'-Amino-N-ethyl-5'-fluorospiro[piperidine-4,2'(1'H)-quinazoline]-1-carboxamide hydrochloride This was prepared using the method of Example 246 using the intermediate of Example LL to give a pale yellow amorphous powder, m.p. 200° C. (dec.), MS (+CI) 306 ([M+H]+).

EXAMPLE 248

Ethyl 4'-Amino-5'-fluorospiro[azetidine-3,2'(1'H)-quinazoline]-1-carboxylate

Ethyl 3-oxoazetidine-1-carboxylate (Y. Nitta, T. Yamagouchi, T. Tanaka; Heterocycles, 1986, 24, 25) (175 mg, 1.22 mmol) and 2-amino-6-fluorobenzamidine dihydrochloride (Example C, 280 mg, 1.22 mmol) in dry DMF (10 ml) were heated at 80° C. for 4 hours. The resulting solution was cooled and poured into aqueous sodium bicarbonate solution and the resulting mixture was extracted with ethyl acetate. The extracts were concentrated and the residue purified by flash chromatography on silica eluting with dichloromethane/methanol (10:1) to give the title compound as a solid (0.13 g) m.p. 210°–212° C.

EXAMPLE 249

Phenylmethyl 4'-Amino-5'-fluorospiro[azetidine-3,2'(1'H)-quinazoline]-1-carboxylate This was prepared by the method of Example 248 using benzyl 3-oxoazetidine-1-carboxylate and obtained as a solid, m.p. 157°–159° C.

EXAMPLE 250

5'-Fluorospiro[azetidine-3,2'(1'H)-quinazoline]-4'-amine

Phenylmethyl 4'-Amino-5'-fluorospiro[azetidine-3,2'(1'H)-quinazoline]-1-carboxylate (Example 249, 1 g, 2.94 mmol) in ethanol (50 ml) containing 10% palladium on carbon catalyst (0.1 g) was stirred under hydrogen at 3 atmospheres pressure for 48 h. The catalyst was removed by filtration and the filtrate concentrated to leave the crude title compound as a gum (0.6 g), MS (+CI) 207 ([M+H]+).

EXAMPLE 251

5'-fluoro-1-(2-thienylcarbonyl)spiro[azetidine-3,2'(1'H)-quinazoline]4'-amine:

5'-Fluorospiro[azetidine-3,2'(1'H)quinazoline]-4'-amine (Example 250, 206 mg, 1 mmol) and triethylamine (0.28 ml., 2 mmol) in dry dichloromethane (15 ml) was stirred at 20° C. and thiophene-2-carbonyl chloride (0.12 ml, 1.1 mmol) added. The mixture was stirred at ambient temperature for 3 h then concentrated to dryness and separated by flash chromatography on silica using dichloromethane/methanol mixtures as eluant. The more polar fraction eluted afforded the title compound (50 mg) as a solid, m.p. 214°–215° C.

EXAMPLE 252

1-(3,5-Dimethylisoxazol-4-yl)sulphonyl)spiro[piperidine-4,2'(1'H)-quinazoline]-1'amine hydrochloride A suspension of spiro[piperidine-4,2'(1'H)-quinazoline]-4'-amine dihydrochloride (Example 241) (0.20 g, 0.70 mmol) in pyridine (10 ml) was treated with solid 3,5-dimethylisoxazole-4-sulphonyl chloride (0.14 g, 0.70 mmol) and the mixture stirred for 24 h. The solvent was evaporated and the residue taken up in methanol, stirred for 16 h and evaporated. The resulting residue was purified by flash chromatography on neutral alumina eluting with 25% ethanol/dichloromethane to afford a yellow glass, MS (+CI) 376 ([M+H]+), 1H NMR (d$_6$-DMSO) 7.81 (1H, d, J 8.0 Hz), 7.60 (1H, br. s), 7.46 (1H, t, J7.6 Hz), 6.88 (1H, d, J 8.3 Hz), 6.80 (1H, t, J 7.6 Hz), 3.32 (4H, m), 2.64 (3H, s).

EXAMPLE 253

2-Ethynyl-1,2-dihydro-4-quinazolinamine hydrochloride

A suspension of 1,2-dihydro-2-(trimethylsilylethynyl)-4-quinazolinamine hydrochloride (Example 24, 0.6 g, 2.14 mmol) in THF (30 ml) was treated with tert-butyl-ammonium fluoride (1.0M in THF, 2.36 ml) and stirred for 2 h. The mixture was evaporated and purified by flash chromatography on untreated neutral alumina eluting with 20% methanol/dichloromethane to give, after crystallisation with ethanol/ether, the product as a yellow powder (90 mg), m.p. 198°–200° C. (dec.).

EXAMPLE 254

2-(2-(2-Aminoethyl)phenyl)-1,2-dihydro-4-quinazolinamine dihydrochloride

To a solution of 2-(2-(2-azidoethyl)phenyl)-1,2-dihydro-4-quinazolinamine hydrochloride (Example 50, 0.38 g, 1.16 mmol) in methanol (10 ml) was added tin dichloride (0.33 g, 1.73 mmol) and the mixture stirred for 2 h (effervescence). Evaporation and purification by RPHPLC eluting with trifluoroacetic acid/water/methanol (1:90:10, increasing the gradient to 1:5:95) gave the product, MS (+FAB) 266 ([M+H]+), 1H NMR (d$_6$-DMSO) 10.07 (1H, s), 9.29 (1H, s), 8.51 (1H, s), 7.98 (2H, s), 7.91 (1H, s), 7.69 (1H, d), 7.33–7.55 (4H, m), 6.7–7.0 (2H, m), 6.17 (1H, s), 2.9–3.1 (4H, m).

EXAMPLE 255

1-(4-Aminobenzoyl)spiro[piperidine-4,2'(1'H)-quinazoline]-4'-amine dihydrochloride A suspension of 1-(4-Nitrobenzoyl)spiro[piperidine-4,2'(1'H)-quinazoline]4'-amine hydrochloride (Example 57) (181 mg, 0.45 mnmol) and 10% palladium on charcoal (18 mg, 10 mol%) in ethanol (20 ml) was stirred under 3 atmospheres pressure of hydrogen for 20 h. The mixture was filtered and concentrated in vacuo. Purification by RP-HPLC eluting is with trifluoroacetic acid/water/methanol (1:90:10, increasing the gradient to 1:5:95) gave a yellow foam, MS (+FAB) 336 ([M+H]+), 1H NMR (d$_6$-DMSO) 10.64 (1H, s), 9.30 (1H, s), 8.75 (1H, s), 7.86 (1H, d, J 8.0 Hz), 7.78 (1H, s), 7.48 (1H, t, J 7.7 Hz), 7.42 (2H, d, J 8.2 Hz), 7.23 (2H, d, J 8.1 Hz), 6.94 (1H, d, J 8.3 Hz), 6.81 (1H, t, J 7.6 Hz), 4.05 (2H, br. s), 3.75 (2H, br. s), 3.63 (2H, br. s), 1.97 (2H, br. s), 1.84 (2H, br. s).

EXAMPLE 256

1-(3-Aminobenzoyl)spiro[piperidine-4,2'(1'H)-quinazoline1-4'-amine hydrochloride This was prepared by the method of Example 255, using 1-(3-nitrobenzoyl)spiro-]piperidine-4,2'(1'H)-quinazoline]-4'-amine hydrochloride (Example 62) to give a yellow foam, MS (+EI) 335 (M+), 1H NMR (d6-DMSO) 8.79 (3H, br. s), 7.87 (1H, d, J 8.0 Hz), 7.66 (1H, s), 7.47 (1H, t, J 7.7 Hz), 7.07 (1H, t, J 7.7 Hz), 6.92 (1H, d, J 8.3 Hz), 6.81 (1H, t, J 7.6 Hz), 6.61 (1H, d, J 8.0 Hz), 6.54 (1H, s), 6.46 (1H, d, J 7.2 Hz), 5.30 (2H, s), 3.86 (1H, br. s), 3.64 (1H, br. s), 3.54 (2H, br. s), 1.94 (4H, br. s).

EXAMPLE 257

4-(4'-Aminospiro[piperidine-4,2'(1'H)-quinazoline]-1-ylcarbonyl)benzoic acid hydrochloride A solution of methyl 4-(4'-aminospiro[piperidine-4,2'(1'H)-quinazoline]-1-ylcarbonyl)- benzoate hydrochloride (Example 90)(417 mg) and lithium hydroxide monohydrate (39 mg) in water (1 ml) was stirred for 16 h at room temperature. A further 26 mg of lithium hydroxide in water (2 ml) was added and the mixture heated to 60° C. for 8 h, cooled, acidified with 4N HCl and concentrated to furnish a brown foam, MS (+FAB) 365 ([M+H]+), 1H NMR (d$_6$-DMSO) 13.19 (1H, br. s), 10.72 (1H, s), 9.34 (1H, s), 8.97 (1H, s), 8.01 (2H, d, J8.1 Hz), 7.87 (1H, d, J 7.9 Hz), 7.80 (1H, s), 7.50 (1H, d, J 8.1 Hz), 7.47 (1H, t, J 8.0 Hz), 6.95 (1H, d, J 8.3 Hz), 6.81 (lH, t, J 7.6 Hz), 4.13 (2H, br. s), 4.04 (1H, br. s), 3.72 (1H, br..s), 1.93 (4H, br. s).

We claim:
1. A compound of formula I:

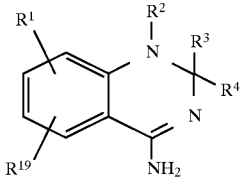

wherein $R_1$ and $R^{19}$ independently represent hydrogen, alkyl C1 to 6, alkoxy C1 to 6, alklthio C1 to 6, halogen, hydroxyl or amino;

$R^3$ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic ring may be optionally substituted by alkyl C1 to 6, alkoxy C1 to 6, halogen, hydroxyl, alkylthio C1 to 6, cyano, trifluoromethyl, nitro, hydroxymethyl, amino, a group —(CH$_2$)$_c$.NHCO$_2$R$^{10}$, a group —(CH$_2$)$_c$.NR$^5$R$^6$, or a group —CO$_2$R$^{11}$, or $R^3$ represents hydrogen or alkyl C1 to 8, which alkyl group may be optionally substituted by amino or a group —NHCO$_2$R$^{10}$; and $R^4$ represents hydrogen or alkyl C1 to 6;

or $R^3$ and $R^4$ taken together represent a group (CH$_2$)$_a$.Z.(CH$_2$)$_b$;

c represents an integer 0 to 2;

a and b independently represent an integer 1 to 3;

Z represents CH$_2$, NH, a group >N(CH$_2$)$_n$YR$^{13}$, a group >NCOX(CH$_2$)$_n$YR$^{13}$, a group >NCSX(CH$_2$)$_n$YR$^{13}$, or a group >NCNHX(CH$_2$)$_n$YR$^{13}$;

X represents O, S or a bond;

Y represents O, S, SO, SO$_2$, NR$^9$ or a bond;

n represents an integer 0 to 6;

$R^{13}$ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or $R^{13}$ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trifluoromethoxy, methanesulphonyl, sulphamoyl, —NR$^{14}$R$^{15}$, —COOR$^{16}$ or —CONR$^7$R$^8$;

or $R^{13}$ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by— benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or $R^{13}$ may be as defined save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

$R^2$, $R^5$, $R^6$, $R^{11}$, $R^9$, $R^{14}$, $R^{15}$ and $R^{16}$ independently represent hydrogen or alkyl C1 to 6;

in addition, when Y represents $NR^9$, —$NR^9R^{13}$ may together represent a pyrroldine or piperidine ring;

$R^{10}$ represents alkyl C1 to 6; and $R^7$ and $R^8$ independently represent hydrogen, alkyl C1 to 6 or phenyl optionally substituted by one or more groups selected from alkyl C1 to 6, halogen, cyano, nitro, hydroxyl, alkoxy C1 to 6, trifluoromethyl and trifluoromethoxy;

provided that (a) when $R^3$ and $R^4$ taken together represent a group $(CH_2)_a.Z.(CH_2)_b$, in which Z represents a group >$NCOX(CH_2)_nYR^{13}$, a group >$NCSX(CH_2)_nYR^{13}$, or a group >$NCNHX(CH_2)_nYR^{13}$ in which neither X nor Y represents a bond then n represents an integer 2 to 4; and (b) when $R^3$ and $R^4$ taken together represent a group $(CH_2)_a.Z.(CH_2)_b$, in which Z represents a group >$NCOX(CH_2)_nYCN$, a group >$NCSX(CH_2)_nYCN$, or a group >$NCNHX(CH_2)_nYCN$, then Y represents a bond and either X also represents a bond or X does not represent a bond and n represents an integer 1 to 4;

(c) when $R^1$, $R^{19}$, $R^2$ and $R^4$ represent hydrogen, $R^3$ does not represent phenyl; and (d) when $R^1$ represents hydrogen or chloro, and $R^{19}$ and $R^2$ represent hydrogen, $R^3$ and $R^4$ do not both represent methyl;

or a pharmaceutically acceptable salt thereof.

2. A compound of formula I as claimed in claim 1, wherein $R^3$ and $R^4$ taken together represent a group $(CH_2)_a.Z.(CH_2)_b$, in which Z represents a group >NCO$(CH_2)_nR^{13}$, a group >NCS$(CH_2)_nR^{13}$, or a group >NCNH$(CH_2)_nR^{13}$ and $R^{13}$ represents optionally substituted phenyl, furyl, thienyl, thiazolyl, isoxazolyl, isothiazolyl, thiadiazolyl, pyridyl or pyrazinyl.

3. A compound of formula I as claimed in claim 2, wherein $R^{13}$ represents substituted phenyl, wherein the substituent is in the para position.

4. A compound of formula I as claimed in claim 3, wherein n represents 0.

5. A compound of formula I as claimed in claim 1, wherein $R^1$ and $R^{19}$ independently represent hydrogen or halogen.

6. A compound of formula I as claimed in claim 5, wherein at least one of $R^1$ and $R^{19}$ represents fluoro or chloro.

7. A compound of formula I as claimed in claim 6, wherein $R^1$ represents 5-fluoro or 5-chloro.

8. A compound of formula I as claimed in claim 7, wherein $R^1$ represents 5-fluoro and $R^{19}$ represents 8-fluoro.

9. A compound of formula I as claimed in claim 1, wherein $R^3$ and $R^4$ taken together represent a group $(CH_2)_a.Z.(CH_2)_b$, in which a and b each represents 2.

10. A compound of formula I as claimed in claim 1, wherein $R^2$ represents hydrogen.

11. A compound of formula I as claimed in claim 1, wherein $R^4$ represents hydrogen and $R^3$ represents ethyl, isopropyl, cyclopropyl, cyclobutyl, furyl, thienyl or substituted phenyl wherein the substituent is fluoro or hydroxyl.

12. A compound of formula I as claimed in claim 1, wherein $R^3$ and $R^4$ taken together represent a group $(CH_2)_a.Z.(CH_2)_b$, in which Z represents a group >$NCO_2(CH_2)_nYR^{13}$ or >$NCSO(CH_2)_nYR^{13}$.

13. A compound of formula I as claimed in claim 12 in which n represents 0, Y represents a bond and $R^{13}$ represents alkyl C1–6 or chloroalkyl C3–6.

14. A compound of formula I as claimed in claim 12 in which n represents 2, Y represents oxygen and $R^{13}$ represents optionally substituted phenyl.

15. A process for the production of a compound of formula I as claimed in claim 1, or a pharmaceutically acceptable salt thereof, which comprises:

(a) reaction of a compound of formula II:

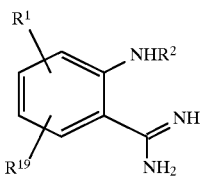

wherein $R^1$, $R^2$ and $R^{19}$ are as defined above, or an acid salt thereof, with a compound of formula III:

wherein $R^3$ and $R^4$ are as defined above, or a protected derivative thereof;

(b) preparation of a compound of formula I wherein $R^2$ represents alkyl C1 to 6 by alkylation of a corresponding compound of formula I wherein $R^2$ is hydrogen;

(c) preparation of a compound of formula I in which one or more of the substituents contains an amino group by reduction of the corresponding nitro or azido compound;

(d) preparation of a compound of formula I wherein $R^{13}$ contains a substituent —$CONR^7R^8$ by reaction of a compound of formula I wherein $R^{13}$ contains a substituent —COOH with an amine $R^7R^8NH$;

(e) preparation of a compound of formula I where $R^3$ and $R^4$ together represent $(CH_2)_aZ(CH_2)_b$ and Z represents >$NCOX(CH_2)_nYR^{13}$ by reaction of a compound of formula I where $R^3$ and $R^4$ together represent $(CH_2)_aZ(CH_2)_b$ and Z represents >NH with a compound of formula IV:

wherein $R^{13}$, X, Y and n are as defined above and L is a leaving group;

(f) preparation of a compound of formula I where $R^3$ and $R^4$ together represent $(CH_2)_aZ(CH_2)_b$ and Z represents >$NSO_2R^{13}$ by reaction of a compound of formula I where $R^3$ and $R^4$ together represent $(CH_2)_aZ(CH_2)_b$ and Z represents >NH with a compound of formula V:

wherein $R^{13}$ is as defined above and L is a leaving group;

(g) preparation of a compound of formula I wherein $R^3$ or $R^{13}$ represents a ring substituted by a group —$COOR^{11}$ or —$COOR^{16}$ respectively and $R^{11}$ or $R^{16}$ represents alkyl C1 to 6 by esterification of the compound where $R^{11}$ or $R^{16}$ represents hydrogen;

(h) deprotection of a compound of formula I wherein one or more atoms is protected;

(i) reaction of a compound of formula XXII:

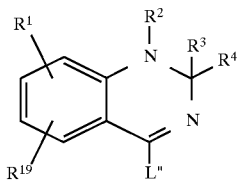

wherein $R^1$, $R^2$, $R^3$, $R^4$ and $R^{19}$ are as defined above, and L" is a leaving group, or a protected derivative thereof, with ammonia or a deprotonated derivative thereof;

(j) deoxygenation of the tautomeric compounds of formula XXVIII(a) or XXVIII(b):

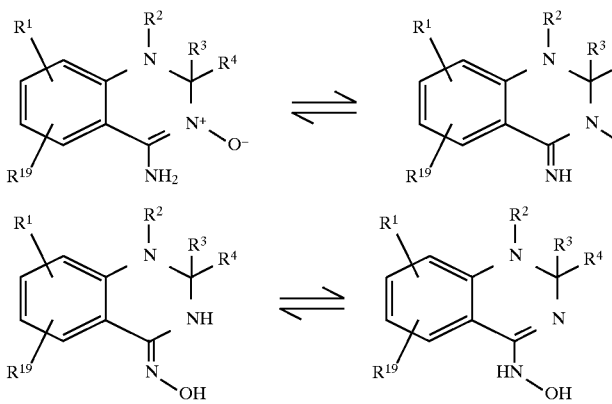

wherein $R^1, R^2, R^3, R^4$ and $R^{19}$ are as defined above, or a protected derivative thereof; or (k) preparation of a compound of formula I in which $R^2$ and $R^4$ both represent hydrogen by reduction of a compound of formula XXIX:

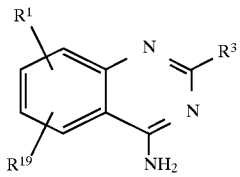

wherein $R^1$, $R^3$ and $R^{19}$ are as defined above, or a protected derivative thereof;

and where desired or necessary converting the resultant compound of formula I, or another salt thereof, to a pharmaceutically acceptable salt thereof, or vice versa.

16. A method of treatment or prophylaxis of diseases or conditions in which inhibition of NOS is beneficial, which comprises administering to a person in need thereof a therapeutically effective amount of a compound of formula (I):

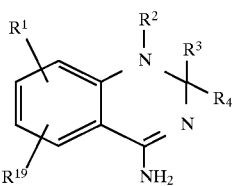

wherein $R^1$ and $R^{19}$ independently represent hydrogen, alkyl C1 to 6, alkoxy C1 to 6, alkylthio C1 to 6, halogen, hydroxyl or amino;

$R^3$ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic ring may be optionally substituted by alkyl C1 to 6, alkoxy C1 to 6, halogen, hydroxyl, alkylthio C1 to 6, cyano, trifluoromethyl, nitro, hydroxymethyl, amino, a group —$(CH_2)_c$.$NHCO_2R^{10}$, a group —$(CH_2)_c$.$NR^5R^6$, or a group —$CO_2R^{11}$, or $R^3$ represents hydrogen or alkyl C1 to 8, which alkyl group may be optionally substituted by amino or a group —$NHCO_2R^{10}$; and $R^4$ represents hydrogen or alkyl C1 to 6;

or $R^3$ and $R^4$ taken together represent a group $(CH_2)_a$.Z.$(CH_2)_b$;

c represents an integer 0 to 2;

a and b independently represent an integer 1 to 3;

Z represents $CH_2$, NH, a group >$N(CH_2)_n YR^{13}$, a group >$NCOX(CH_2)_n YR^{13}$, a group >$NCSX(CH_2)_n YR^{13}$, or a group >$NCNHX(CH_2)_n YR^{13}$;

X represents O, S or a bond;

Y represents O, S, SO, $SO_2$, $NR^9$ or a bond;

n represents an integer 0 to 6;

$R^{13}$ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or $R^{13}$ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trifluoromethoxy, methanesulphonyl, sulphamoyl, —NR$^{14}$R$^{15}$, —COOR$^{16}$ or —CONR$^{7}$R$^{8}$;

or R$^{13}$ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or R$^{13}$ may be as defined save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

R$^2$, R$^5$, R$^6$, R$^{11}$, R$^9$, R$^{14}$, R$^{15}$ and R$^{16}$ independently represent hydrogen or alkyl C1 to 6;

in addition, when Y represents NR$^9$, —NR$^9$R$^{13}$ may together represent a pyrrolidine or piperidine ring;

R$^{10}$ represents alkyl C1 to 6; and

R$^7$ and R$^8$ independently represent hydrogen, alkyl C1 to 6 or phenyl optionally substituted by one or more groups selected from alkyl C1 to 6, halogen, cyano, nitro, hydroxyl, alkoxy C1 to 6, trifluoromethyl and trifluoromethoxy; provided that (a) when R$^3$ and R$^4$ taken together represent a group (CH$_2$)$_a$.Z.(CH$_2$)$_b$, in which Z represents a group >NCOX(CH$_2$)$_n$YR$^{13}$, a group >NCSX(CH$_2$)$_n$YR$^{13}$, or a group >NCNHX(CH$_2$)$_n$YR$^{13}$ in which neither X nor Y represents a bond then n represents an integer 2 to 4; and (b) when R$^3$ and R$^4$ taken together represent a group (CH$_2$)$_a$.Z.(CH$_2$)$_b$, in which Z represents a group >NCOX(CH$_2$)$_n$YCN, a group >NCSX(CH$_2$)$_n$YCN, or a group >NCNHX(CH$_2$)$_n$YCN, then Y represents a bond and either X also represents a bond or X does not represent a bond and n represents an integer 1 to 4;

or a pharmaceutically acceptable salt thereof.

17. A method according to claim 16, in which it is predominantly the inducible isoform of NOS that is inhibited.

18. A pharmaceutical formulation comprising a therapeutically effective amount of a compound of formula (I):

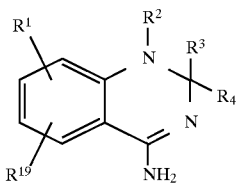

wherein

R$^1$ and R$^{19}$ independently represent hydrogen, alkyl C1 to 6, alkoxy C1 to 6, alkylthio C1 to 6, halogen, hydroxyl or amino;

R$^3$ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic ring may be optionally substituted by alkyl C1 to 6, alkoxy C1 to 6, halogen, hydroxyl, alkylthio C1 to 6, cyano, trifluoromethyl, nitro, hydroxymethyl, amino, a group —(CH$_2$)$_c$.NHCO$_2$R$^{10}$, a group —(CH$_2$)$_c$.NR$^5$R$^6$, or a group —CO$_2$R$^{11}$, or R$^3$ represents hydrogen or alkyl C1 to 8, which alkyl group may be optionally substituted by amino or a group —NHCO$_2$R$^{10}$; and R$^4$ represents hydrogen or alkyl C1 to 6;

or R$^3$ and R$^4$ taken together represent a group (CH$_2$)$_a$.Z.(CH$_2$)$_b$;

c represents an integer 0 to 2;

a and b independently represent an integer 1 to 3;

Z represents CH$_2$, NH, a group >N(CH$_2$)$_n$YR$^{13}$, a group >NCOX(CH$_2$)$_n$YR$^{13}$, a group >NCSX(CH$_2$)$_n$YR$^{13}$, or a group >NCNHX(CH$_2$)$_n$YR$^{13}$;

X represents O, S or a bond;

Y represents O, S, SO, SO$_2$, NR$^9$ or a bond;

n represents an integer 0 to 6;

R$^{13}$ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or R$^{13}$ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trifluoromethoxy, methanesulphonyl, sulphamoyl, —NR$^{14}$R$^{15}$, —COOR$^{16}$ or —CONR$^{7}$R$^{8}$;

or R$^{13}$ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or R$^{13}$ may be as defined save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

R$^2$, R$^5$, R$^6$, R$^{11}$, R$^9$, R$^{14}$, R$^{15}$ and R$^{16}$ independently represent hydrogen or alkyl C1 to 6;

in addition, when Y represents NR$^9$, —NR$^9$R$^{13}$ may together represent a pyrrolidine or piperidine ring;

R$^{10}$ represents alkyl C1 to 6; and

R$^7$ and R$^8$ independently represent hydrogen, alkyl C1 to 6 or phenyl optionally substituted by one or more groups selected from alkyl C1 to 6, halogen, cyano, nitro, hydroxyl, alkoxy C1 to 6, trifluoromethyl and trifluoromethoxy; provided that (a) when R³ and R⁴ taken together represent a group (CH₂)$_a$.Z.(CH₂)$_b$, in which Z represents a group >NCOX(CH₂)$_n$YR¹³, a group >NCSX(CH₂)$_n$YR¹³, or a group >NCNHX(CH₂)$_n$YR¹³ in which neither X nor Y represents a bond then n represents an integer 2 to 4; and (b) when R³ and R⁴ taken together represent a group (CH₂)$_a$.Z.(CH₂)$_b$, in which Z represents a group >NCOX(CH₂)$_n$YCN, a group >NCSX(CH₂)$_n$YCN, or a group >NCNHX(CH₂)$_n$YCN, then Y represents a bond and either X also represents a bond or X does not represent a bond and n represents an integer 1 to 4;

or a pharmaceutically acceptable salt thereof, in admixture with a pharmaceutically acceptable adjuvant, diluent or carrier.

19. A method of relieving pain in a patient, comprising administering to the patient a compound of formula (I):

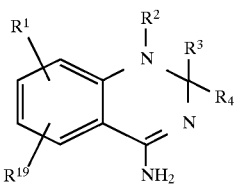

wherein

R¹ and R¹⁹ independently represent hydrogen, alkyl C1 to 6, alkoxy C1 to 6, alkylthio C1 to 6, halogen, hydroxyl or amino;

R³ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic ring may be optionally substituted by alkyl C1 to 6, alkoxy C1 to 6, halogen, hydroxyl, alkylthio C1 to 6, cyano, trifluoromethyl, nitro, hydroxymethyl, amino, a group —(CH₂)$_c$.NHCO₂R¹⁰, a group —(CH₂)$_c$.NR⁵R⁶, or a group —CO₂R¹¹, or R³ represents hydrogen or alkyl C1 to 8, which alkyl group may be optionally substituted by amino or a group —NHCO₂R¹⁰; and R⁴ represents hydrogen or alkyl C1 to 6;

or R³ and R⁴ taken together represent a group (CH₂)$_a$.Z.(CH₂)$_b$;

c represents an integer 0 to 2;

a and b independently represent an integer 1 to 3;

Z represents CH₂, NH, a group >N(CH₂)$_n$YR¹³, a group >NCOX(CH₂)$_n$YR¹³, a group >NCSX(CH₂)$_n$YR¹³, or a group >NCNHX(CH₂)$_n$YR¹³;

X represents O, S or a bond;

Y represents O, S, SO, SO₂, NR⁹ or a bond;

n represents an integer 0 to 6;

R¹³ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or R¹³ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trifluoromethoxy, methanesulphonyl, sulphamoyl, —NR¹⁴R¹⁵, —COOR¹⁶ or —CONR⁷R⁸;

or R¹³ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or R¹³ may be as defined save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

R², R⁵, R⁶, R¹¹, R⁹, R¹⁴, R¹⁵ and R¹⁶ independently represent hydrogen or alkyl C1 to 6;

in addition, when Y represents NR⁹, —NR⁹R¹³ may together represent a pyrrolidine or piperidine ring;

R¹⁰ represents alkyl C1 to 6; and

R⁷ and R⁸ independently represent hydrogen, alkyl C1 to 6 or phenyl optionally substituted by one or more groups selected from alkyl C1 to 6, halogen, cyano, nitro, hydroxyl, alkoxy C1 to 6, trifluoromethyl and trifluoromethoxy; provided that (a) when R³ and R⁴ taken together represent a group (CH₂)$_a$.Z.(CH₂)$_b$, in which Z represents a group >NCOX(CH₂)$_n$YR¹³, a group >NCSX(CH₂)$_n$YR¹³, or a group >NCNHX(CH₂)$_n$YR¹³ in which neither X nor Y represents a bond then n represents an integer 2 to 4; and (b) when R³ and R⁴ taken together represent a group (CH₂)$_a$.Z.(CH₂)$_b$, in which Z represents a group >NCOX(CH₂)$_n$YCN, a group >NCSX(CH₂)$_n$YCN, or a group >NCNHX(CH₂)$_n$YCN, then Y represents a bond and either X also represents a bond or X does not represent a bond and n represents an integer 1 to 4;

or a pharmaceutically acceptable salt thereof.

20. A method of treating an inflammatory disorder in a patient, comprising administering to said patient a compound of formula (I):

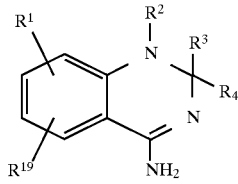

wherein

R¹ and R¹⁹ independently represent hydrogen, alkyl C1 to 6, alkoxy C1 to 6, alkylthio C1 to 6, halogen, hydroxyl or amino;

R³ represents phenyl, a 6-membered heterocyclic aromatic ring containing one or two nitrogen atoms, or a 5-membered heterocyclic aromatic ring containing 1 to 3 heteroatoms selected from O, N and S, which phenyl or heterocyclic aromatic ring may be optionally substituted by alkyl C1 to 6, alkoxy C1 to 6, halogen, hydroxyl, alkylthio C1 to 6, cyano, trifluoromethyl, nitro, hydroxymethyl, amino, a group $-(CH_2)_c-NHCO_2R^{10}$, a group $-(CH_2)_c-NR^5R^6$, or a group $-CO_2R^{11}$, or $R^3$ represents hydrogen or alkyl C1 to 8, which alkyl group may be optionally substituted by amino or a group $-NHCO_2R^{10}$; and $R^4$ represents hydrogen or alkyl C1 to 6;

or $R^3$ and $R^4$ taken together represent a group $(CH_2)_a \cdot Z \cdot (CH_2)_b$;

c represents an integer 0 to 2;

a and b independently represent an integer 1 to 3;

Z represents $CH_2$, NH, a group $>N(CH_2)_nYR^{13}$, a group $>NCOX(CH_2)_n YR^{13}$, a group $>NCSX(CH_2)_nYR^{13}$, or a group $>NCNHX(CH_2)_nYR^{13}$;

X represents O, S or a bond;

Y represents O, S, SO, $SO_2$, $NR^9$ or a bond;

n represents an integer 0 to 6;

$R^{13}$ represents alkyl C1 to 6, alkyl C1 to 6 substituted by one or more halogen atoms, cyano, quinolyl, phenyl, naphthyl, a 6-membered heterocyclic aromatic ring containing one or two nitrogen atoms, a 5-membered heterocyclic aromatic ring containing 1 to 3 heteroatoms selected from O, N and S, or a benzene ring fused with a 5-membered heterocyclic aromatic ring containing 1 to 3 heteroatoms selected from O, N and S;

or $R^{13}$ may be as defined save that when it contains one or more aromatic rings, said rings may be optionally substituted by one or more groups selected from alkyl C1 to 6, halogen, cyano, nitro, hydroxyl, alkoxy C1 to 6, trifluoromethyl, trifluoromethoxy, methanesulphonyl, sulphamoyl, $-NR^{14}R^{15}$, $-COOR^{16}$ or $-CONR^7R^8$;

or $R^{13}$ may represent a phenyl ring, a 6-membered heterocyclic aromatic ring containing one or two nitrogen atoms, or a 5-membered heterocyclic aromatic ring containing 1 to 3 heteroatoms selected from O, N and S substituted by benzyloxy or optionally substituted phenyl, or an optionally substituted 5-membered heterocyclic aromatic ring containing 1 to 3 heteroatoms selected from O, N and S, wherein the optional substituents are alkyl C1 to 6, halogen, cyano, nitro, hydroxyl, alkoxy C1 to 6, trifluoromethyl and trifluoromethoxy;

or $R^{13}$ may be as defined save that when it contains a heterocyclic aromatic ring containing at least one nitrogen atom, said ring may be optionally substituted by one or more oxo groups adjacent to the nitrogen, the ring being attached to the remainder of the molecule through one of the nitrogen atoms or otherwise;

$R^2$, $R^5$, $R^6$, $R^{11}$, $R^9$, $R^{14}$, $R^{15}$ and $R^{16}$ independently represent hydrogen or alkyl C1 to 6;

in addition, when Y represents $NR^9$, $-NR^9R^{13}$ may together represent a pyrrolidine or piperidine ring;

$R^{10}$ represents alkyl C1 to 6; and $R^7$ and $R^8$ independently represent hydrogen, alkyl C1 to 6 or phenyl optionally substituted by one or more groups selected from alkyl C1 to 6, halogen, cyano, nitro, hydroxyl, alkoxy C1 to 6, trifluoromethyl and trifluoromethoxy; provided that (a) when $R^3$ and $R^4$ taken together represent a group $(CH_2)_a \cdot Z \cdot (CH_2)_b$, in which Z represents a group $>NCOX(CH_2)_nYR^{13}$, a group $>NCSX(CH_2)_nYR^{13}$, or a group $>NCNHX(CH_2)_nYR^{13}$ in which neither X nor Y represents a bond then n represents an integer 2 to 4; and (b) when $R^3$ and $R^4$ taken together represent a group $(CH_2)_a \cdot Z \cdot (CH_2)_b$, in which Z represents a group $>NCOX(CH_2)_nYCN$, a group $>NCSX(CH_2)_nYCN$, or a group $>NCNHX(CH_2)_nYCN$, then Y represents a bond and either X also represents a bond or X does not represent a bond and n represents an integer 1 to 4;

or a pharmaceutically acceptable salt thereof.

* * * * *